US012747516B2

(12) United States Patent
Tadross et al.

(10) Patent No.: US 12,747,516 B2
(45) Date of Patent: Sep. 29, 2026

(54) PROTEIN LIBRARY DISPLAY SYSTEMS AND METHODS THEREOF

(71) Applicant: Duke University, Durham, NC (US)

(72) Inventors: Michael Tadross, Durham, NC (US); Victoria Goldenshtein, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 18/875,071

(22) PCT Filed: Jun. 15, 2023

(86) PCT No.: PCT/US2023/025475

§ 371 (c)(1),
(2) Date: Dec. 13, 2024

(87) PCT Pub. No.: WO2023/244760

PCT Pub. Date: Dec. 21, 2023

(65) Prior Publication Data

US 2025/0263690 A1 Aug. 21, 2025

Related U.S. Application Data

(60) Provisional application No. 63/492,180, filed on Mar. 24, 2023, provisional application No. 63/352,458, filed on Jun. 15, 2022.

(51) Int. Cl.
*C40B 40/08* (2006.01)
*C12N 15/10* (2006.01)

(52) U.S. Cl.
CPC .......... *C40B 40/08* (2013.01); *C12N 15/1062* (2013.01); *C12N 15/1086* (2013.01); *C12N 15/1093* (2013.01)

(58) Field of Classification Search
None
See application file for complete search history.

(56) References Cited

U.S. PATENT DOCUMENTS 7,074,557 B2 7/2006 Osbourn et al.
8,569,065 B2 10/2013 Polach et al.
(Continued)

FOREIGN PATENT DOCUMENTS

WO 2021/178926 A1 9/2021

OTHER PUBLICATIONS

International Search Report and Written Opinion for Application No. PCT/US2023/025475 dated Nov. 14, 2023 (13 pages).
(Continued)

*Primary Examiner* — Christian C Boesen
(74) *Attorney, Agent, or Firm* — MICHAEL BEST & FRIEDRICH LLP

(57) ABSTRACT

Disclosed herein are protein-RNA display constructs that couple a protein of interest to its encoding mRNA. An example protein-RNA display construct includes a first nucleotide portion including an RNA that forms hairpin structures; a second nucleotide portion including an mRNA encoding a protein of interest; a first protein portion including a protein having RNA hairpin binding peptides that can specifically bind to the RNA hairpin structures; and a second protein portion including the protein of interest. The protein-RNA display constructs take advantage of binding interactions between RNA hairpin structures and RNA hairpin binding peptides to stably couple the protein of interest to its encoding mRNA. Also disclosed are nucleic acids encoding the protein-RNA display constructs, libraries and kits including the protein-RNA display constructs, and methods (Continued)

of using the protein-RNA display constructs in high-throughput display applications.

10 Claims, 47 Drawing Sheets

Specification includes a Sequence Listing.

(56) References Cited

U.S. PATENT DOCUMENTS

| | | | |
|---|---|---|---|
| 8,916,504 B2 | 12/2014 | Hsieh et al. |
| 9,657,288 B2 | 5/2017 | Winter et al. |
| 2011/0177071 A1 | 7/2011 | Karrer et al. |

OTHER PUBLICATIONS

Invitation to Pay Additional Fees for Application No. PCT/US2023/025475 dated Sep. 5, 2023 (3 pages).
Armbruster et al., "Evolving the lock to fit the key to create a family of G protein-coupled receptors potently activated by an inert ligand," Proc Natl Acad Sci U S A., 2007, 104(12): 5163-5168.
Austin et al., "Designed Arginine-Rich RNA-Binding Peptides with Picomolar Affinity," J Am Chem Soc, 2002, 124(37): 10966-10967.
Baron-Benhamou et al., "Using the lambdaN peptide to tether proteins to RNAs," Methods Mol Biol, 2004, 257: 135-154.
Bhide et al., "Library-based display technologies: where do we stand?," Mol Biosyst, 2016, 12(8): 2342-2358.
Buntz, "50 of 2021's best-selling pharmaceuticals," Drug Discovery and Development, 2022, accessed on May 10, 2022. <https://www.drugdiscoverytrends.com/50-of-2021s-best-selling-pharmaceuticals/>.
Cotten et al., "Selection of proteins with desired properties from natural proteome libraries using mrna display," Nat Protoc, 2011, 6(8): 1163-1182.
Daigle et al., "AN-GFP: An RNA reporter system for live-cell imaging," Nat Methods, 2007, 4(8): 633-636.
Fus-Kujawa et al., "An Overview of Methods and Tools for Transfection of Eukaryotic Cells in vitro," Front Bioeng Biotechnol, 2021, 9: 701031.
Gautier et al., "An Engineered Protein Tag for Multiprotein Labeling in Living Cells," Chem Biol, 2008, 15(2): 128-136.
Gronemeyer et al., "Directed evolution of 06-alkylguanine-DNA alkyltransferase for applications in protein labeling," Protein Eng Des Sel, 2006, 19(7): 309-316.
Huang et al., "Development of Anti-Infectives Using Phage Display: Biological Agents against Bacteria, Viruses, and Parasites," Antimicrob Agents Chemother, 2012, 56(9): 4569-4582.
Kebschull et al., "High-Throughput Mapping of Single-Neuron Projections by Sequencing of Barcode RNA," Neuron, 2016, 91: 975-987.
Kenrick et al., "Bacterial display enables efficient and quantitative peptide affinity maturation," Protein Engineering, Design & Selection, 2010, 23(1): 9-17.
Lipovsek et al., "Erratum to: In-vitro protein evolution by ribosome display and mRNA display," [J. Immunol. Methods. 290 (2004) 51-67], J Immunol Methods, 2004, 294(1-2): 213.
Liu et al., "Construction of ribosome display library based on lipocalin scaffold and screening anticalins with specificity for estradiol," Analyst, 2012, 137(10): 2470-2479.
Los et al., "HaloTag: A Novel Protein Labeling Technology for Cell Imaging and Protein Analysis," ACS Chem Biol, 2008, 3(6): 373-382.
Montiel-Gonzalez et al., "Correction of mutations within the cystic fibrosis transmembrane conductance regulator by site-directed RNA editing," PNAS, 2013, 110(45): 18285-18290.
Oikonomou et al., "In Vitro mRNA display enables large-scale proteomics by next generation sequencing," PNAS, 2020, 117(43): 26710-26718.
Peikon et al., "Using high-throughput barcode sequencing to efficiently map connectomes," Nucleic Acids Res, 2017, 45(12): 1-16.
Pries et al., "Histidine 289 is essential for hydrolysis of the alkyl-enzyme intermediate of haloalkane dehalogenase," J Biol Chem, 1995, 270(18): 10405-10411.
Prokop et al., "Engineering of Protein Tunnels: Keyhole-Lock-Key Model for Catalysis by Enzymes with Buried Active Sites," Protein Engineering Handbook, 2012, vol. 3, Chapter 17, 42 pages.
Shields et al., "Deconstructing behavioral neuropharmacology with cellular specificity," Science, 2017, 356: eaaj2161, 9 pages.
Starke et al., "FXS causing missense mutations disrupt FMRP granule formation, dynamics, and function," PLoS Genet, 2022, 18(2): e1010084.
Tang et al., "Construction of "small-intelligent" focuced mutagenesis libraries using well-designed combinatorial degenerate primers," Biotechniques, 2018, 52(3): 149-158.
Tanner et al., "Genetic identification of nascent peptides that induce ribosome stalling," J Biol Chem, 2009, 284(50): 34809-34818.
Usmani et al., "THPdb: Database of FDA-approved peptide and protein therapeutics," PLoS, 2017, 12(7): e0181748.
Vieu et al., "Dual Role of boxB RNA Motif in the Mechanism of Termination/Antitermination at the Lambda tR1 Terminator Revealed in vivo," Journal of Molecular Biology, 2024, 339: 1077-1087.
Yonehara et al., ""MAPseq"-uencing Long-Range Neuronal Projections," Neuron, 2016, 91(5): 945-947.
Zhang et al., "Mechanisms of ribosome stalling by SecM at multiple elongation steps," Elife, 2015, 4 (Dec. 2015): 1-25.
Katz et al., "An in Vivo Binding Assay for RNA-Binding Proteins Based on Repression of a Reporter Gene," ACS Synth. Biol., 2018, 7(12): 2765-2774.

| | Ribosome Display | Phage Display | mRNA Display | GRIP Display |
|---|---|---|---|---|
| Linkage Stability | - | + | + | + |
| Library Size | + | - | + | + |
| Large Proteins | + | + | - | + |
| Time per Round | days | weeks | weeks | days |
| % yield after purification | 100 | 100 | 1-30 | 100 |

FIG. 1B

| | |
|---|---|
| Red: | Arginine residues on the surface of GFP exposed to $boxB_{Toy}$ |
| Brown: | Location of possible GFP residues truncations |
| Yellow: | Location of Glycine linkers of various lengths |
| Light Green: | Location of the two 1-3 EAAAK loop helices |

SEQUENCE LISTING

Sequence total quantity: 40
SEQ ID NO: 1 moltype = DNA length = 66
FEATURE Location/Qualifiers
source 1..66
mol_type = other DNA
organism = synthetic construct
SEQUENCE: 1
atggacgcac aaacacgacg acgtgagcgt cgcgctgaga aacaagctca atggaaagct 60
gcaaac 66

SEQ ID NO: 2 moltype = AA length = 22
FEATURE Location/Qualifiers
source 1..22
mol_type = protein
organism = synthetic construct

```
SEQUENCE: 2
MDAQTRRRER RAEKQAQWKA AN                                            22

SEQ ID NO: 3            moltype = DNA  length = 66
FEATURE                 Location/Qualifiers
source                  1..66
                        mol_type = other DNA
                        organism = synthetic construct
SEQUENCE: 3
ggtaatgcac gtacacgacg acgtgagcgt cgcgctgaga aacaagctca atggaaagct  60
gcaaac                                                              66

SEQ ID NO: 4            moltype = AA  length = 22
FEATURE                 Location/Qualifiers
source                  1..22
                        mol_type = protein
                        organism = synthetic construct
SEQUENCE: 4
GNARTRRRER RAEKQAQWKA AN                                            22

SEQ ID NO: 5            moltype = DNA  length = 66
FEATURE                 Location/Qualifiers
source                  1..66
                        mol_type = other DNA
                        organism = synthetic construct
SEQUENCE: 5
ggaaatgccc gaacacggcg gcgcgagcgt cgagctgaaa aacaagcaca gtggaaggca  60
gcaaat                                                              66

SEQ ID NO: 6            moltype = AA  length = 22
FEATURE                 Location/Qualifiers
source                  1..22
                        mol_type = protein
                        organism = synthetic construct
SEQUENCE: 6
GNARTRRRER RAEKQAQWKA AN                                            22

SEQ ID NO: 7            moltype = DNA  length = 66
FEATURE                 Location/Qualifiers
source                  1..66
                        mol_type = other DNA
                        organism = synthetic construct
SEQUENCE: 7
ggtaacgcac ggacccgacg acgagaacgc cgggcggaga agcaagctca gtggaaagcg  60
gctaat                                                              66

SEQ ID NO: 8            moltype = AA  length = 22
FEATURE                 Location/Qualifiers
source                  1..22
                        mol_type = protein
                        organism = synthetic construct
SEQUENCE: 8
GNARTRRRER RAEKQAQWKA AN                                            22

SEQ ID NO: 9            moltype = DNA  length = 66
FEATURE                 Location/Qualifiers
source                  1..66
                        mol_type = other DNA
                        organism = synthetic construct
SEQUENCE: 9
ggaaacgctc gtacgcgtcg ccgtgagcga cgtgcagaaa agcaggcgca atggaaagct  60
gccaac                                                              66

SEQ ID NO: 10           moltype = AA  length = 22
FEATURE                 Location/Qualifiers
source                  1..22
                        mol_type = protein
                        organism = synthetic construct
SEQUENCE: 10
GNARTRRRER RAEKQAQWKA AN                                            22

SEQ ID NO: 11           moltype = DNA  length = 66
FEATURE                 Location/Qualifiers
source                  1..66
                        mol_type = other DNA
                        organism = synthetic construct
SEQUENCE: 11
ggcaatgcgc gcactcgccg tcgggaacgg cgcgccgaga aacaggccca atggaaggcc  60
gcgaat                                                              66
```

```
SEQ ID NO: 12          moltype = AA  length = 22
FEATURE                Location/Qualifiers
source                 1..22
                       mol_type = protein
                       organism = synthetic construct
SEQUENCE: 12
GNARTRRRER RAEKQAQWKA AN                                           22

SEQ ID NO: 13          moltype = AA  length = 22
FEATURE                Location/Qualifiers
source                 1..22
                       mol_type = protein
                       organism = synthetic construct
SEQUENCE: 13
GNARTRRRER RAEKQAQWKA AN                                           22

SEQ ID NO: 14          moltype = DNA  length = 104
FEATURE                Location/Qualifiers
source                 1..104
                       mol_type = other DNA
                       organism = synthetic construct
SEQUENCE: 14
ttttggggcc ctgaaaaagg gcccctttt ttgccctgaa aaagggcaaa ttttaaagcc  60
ctgaaaaagg gcttttttc ccgccctgaa aaagggcggg tttt                    104

SEQ ID NO: 15          moltype = DNA  length = 79
FEATURE                Location/Qualifiers
source                 1..79
                       mol_type = other DNA
                       organism = synthetic construct
SEQUENCE: 15
ttttggggcc ctgaaaaagg gcccctttt ttgccctgaa aaagggcaaa ttttaaagcc  60
ctgaaaaagg gctttttt                                                79

SEQ ID NO: 16          moltype = DNA  length = 54
FEATURE                Location/Qualifiers
source                 1..54
                       mol_type = other DNA
                       organism = synthetic construct
SEQUENCE: 16
ttttggggcc ctgaaaaagg gcccctttt ttgccctgaa aaagggcaaa tttt        54

SEQ ID NO: 17          moltype = DNA  length = 29
FEATURE                Location/Qualifiers
source                 1..29
                       mol_type = other DNA
                       organism = synthetic construct
SEQUENCE: 17
ttttggggcc ctgaaaaagg gcccctttt                                    29

SEQ ID NO: 18          moltype = DNA  length = 83
FEATURE                Location/Qualifiers
source                 1..83
                       mol_type = other DNA
                       organism = synthetic construct
SEQUENCE: 18
gccccccggg cccgccctga aaaagggcgg gggggccctg aaaaagggcc ccggggccct  60
gaaaaagggc ccccccgggg ggc                                          83

SEQ ID NO: 19          moltype =   length =
SEQUENCE: 19
000

SEQ ID NO: 20          moltype =   length =
SEQUENCE: 20
000

SEQ ID NO: 21          moltype = DNA  length = 15
FEATURE                Location/Qualifiers
source                 1..15
                       mol_type = other DNA
                       organism = synthetic construct
SEQUENCE: 21
gccctgaaaa agggc                                                   15

SEQ ID NO: 22          moltype = AA  length = 333
FEATURE                Location/Qualifiers
source                 1..333
```

```
                         mol_type = protein
                         organism = synthetic construct
SEQUENCE: 22
MSKGEELFTG VVPILVELDG DVNGHKFSVR GEGEGDATIG KLTLKFICTT GKLPVPWPTL  60
VTTLTYGVQC FSRYPDHMKR HDFFKSAMPE GYVQERTISF KDDGKYKTRA VVKFEGDTLV  120
NRIELKGTDF KEDGNILGHK LEYNFNSHNV YITADKQKNG IKANFTVRHN VEGGGNARTR  180
RRERRAEKQA QWKAANGEAA AKEAAAKEAA AKGDGSVQLA DHYQQNTPIG DGPVLLPDNH  240
YLSTQTVLSK GNARTRRRER RAEKQAQWKA ANGGGEAAAK EAAAKEEAAK GGGGGDHMVL  300
HEYVNAAGIT GGNARTRRRE RRAEKQAQWK AAN                              333

SEQ ID NO: 23            moltype = AA  length = 15
FEATURE                  Location/Qualifiers
source                   1..15
                         mol_type = protein
                         organism = synthetic construct
SEQUENCE: 23
EAAAKEAAAK EAAAK                                                  15

SEQ ID NO: 24            moltype = DNA  length = 66
FEATURE                  Location/Qualifiers
source                   1..66
                         mol_type = other DNA
                         organism = synthetic construct
SEQUENCE: 24
ggaaatgcac gaacacgacg ccgggagcgt cgagctgaaa aacaggctca atggaaagcc  60
gcaaat                                                            66

SEQ ID NO: 25            moltype = DNA  length = 66
FEATURE                  Location/Qualifiers
source                   1..66
                         mol_type = other DNA
                         organism = synthetic construct
SEQUENCE: 25
ggcaacgccc gcacccgtcg tcgagaacga cgggccgaaa agcaagcaca gtggaaagct  60
gcgaac                                                            66

SEQ ID NO: 26            moltype = DNA  length = 66
FEATURE                  Location/Qualifiers
source                   1..66
                         mol_type = other DNA
                         organism = synthetic construct
SEQUENCE: 26
ggtaatgctc gtactcgccg acgtgaacgg cgtgcagaga aacaagccca atggaaggca  60
gctaat                                                            66

SEQ ID NO: 27            moltype = DNA  length = 60
FEATURE                  Location/Qualifiers
source                   1..60
                         mol_type = other DNA
                         organism = synthetic construct
SEQUENCE: 27
gaggctgctg ccaaagaggc agccgcaaag gaagctgctg ctaaggaggc ggctgcaaaa  60

SEQ ID NO: 28            moltype = DNA  length = 60
FEATURE                  Location/Qualifiers
source                   1..60
                         mol_type = other DNA
                         organism = synthetic construct
SEQUENCE: 28
gaagcggcag ctaaggaagc agcggcaaaa gaggccgcag cgaaagaagc agcagccaaa  60

SEQ ID NO: 29            moltype = RNA  length = 83
FEATURE                  Location/Qualifiers
source                   1..83
                         mol_type = other RNA
                         organism = synthetic construct
repeat_region            1..5
SEQUENCE: 29
nnnnnnnnnn nnngccctga aaaagggcnn nnnngccctg aaaaagggcn nnnnngccct  60
gaaaaagggc nnnnnnnnnn nnn                                         83

SEQ ID NO: 30            moltype = RNA  length = 83
FEATURE                  Location/Qualifiers
source                   1..83
                         mol_type = other RNA
                         organism = synthetic construct
SEQUENCE: 30
gccccccggg cccgccctga aaaagggcgg gggggccctg aaaaagggcc ccggggccct  60
gaaaaagggc ccccccgggg ggc                                         83
```

```
SEQ ID NO: 31          moltype = RNA  length = 83
FEATURE                Location/Qualifiers
source                 1..83
                       mol_type = other RNA
                       organism = synthetic construct
SEQUENCE: 31
gcgccccggg cccgccctga aaaagggcgg gtgggccctg aaaaagggcc caggggccct  60
gaaaaagggc ccccccgggg cgc                                          83

SEQ ID NO: 32          moltype = RNA  length = 83
FEATURE                Location/Qualifiers
source                 1..83
                       mol_type = other RNA
                       organism = synthetic construct
SEQUENCE: 32
gcgccccggg cccgccctga aaaagggcgg gggggccctg aaaaagggcc ccggggccct  60
gaaaaagggc ccccccgggg cgc                                          83

SEQ ID NO: 33          moltype = RNA  length = 83
FEATURE                Location/Qualifiers
source                 1..83
                       mol_type = other RNA
                       organism = synthetic construct
SEQUENCE: 33
gccgcccggg cccgccctga aaaagggcgg gggggccctg aaaaagggcc ccggggccct  60
gaaaaagggc ccccccgggc ggc                                          83

SEQ ID NO: 34          moltype = RNA  length = 83
FEATURE                Location/Qualifiers
source                 1..83
                       mol_type = other RNA
                       organism = synthetic construct
SEQUENCE: 34
gcccgccggg cccgccctga aaaagggcgg gggggccctg aaaaagggcc ccggggccct  60
gaaaaagggc cccccggcg ggc                                           83

SEQ ID NO: 35          moltype = RNA  length = 83
FEATURE                Location/Qualifiers
source                 1..83
                       mol_type = other RNA
                       organism = synthetic construct
SEQUENCE: 35
gccccgcggg cccgccctga aaaagggcgg gggggccctg aaaaagggcc ccggggccct  60
gaaaaagggc cccccgcgg ggc                                           83

SEQ ID NO: 36          moltype = RNA  length = 83
FEATURE                Location/Qualifiers
source                 1..83
                       mol_type = other RNA
                       organism = synthetic construct
SEQUENCE: 36
gcccccgggg cccgccctga aaaagggcgg gggggccctg aaaaagggcc ccggggccct  60
gaaaaagggc cccccccggg ggc                                          83

SEQ ID NO: 37          moltype = RNA  length = 83
FEATURE                Location/Qualifiers
source                 1..83
                       mol_type = other RNA
                       organism = synthetic construct
SEQUENCE: 37
gccccccccc ccggccctga aaaagggccg gggggccctg aaaaagggcc ccggggccct  60
gaaaaagggc cccggggggg ggc                                          83

SEQ ID NO: 38          moltype = AA  length = 5
FEATURE                Location/Qualifiers
source                 1..5
                       mol_type = protein
                       organism = synthetic construct
REGION                 1..5
                       note = The entire sequence of amino acids 1-5 can be
                        repeated 1 to 100 times
SEQUENCE: 38
SSGSS                                                              5

SEQ ID NO: 39          moltype = AA  length = 5
FEATURE                Location/Qualifiers
source                 1..5
                       mol_type = protein
```

-continued

```
                        organism = synthetic construct
REGION                  1..5
                        note = The entire sequence of amino acids 1-5 can be
                         repeated 1 to 100 times
SEQUENCE: 39
GGSGG                                                               5

SEQ ID NO: 40           moltype =   length =
SEQUENCE: 40
000
```

PROTEIN LIBRARY DISPLAY SYSTEMS AND METHODS THEREOF

CROSS-REFERENCE TO RELATED APPLICATIONS

This patent application is the U.S. national stage entry, under 35 U.S.C. § 371, of International Application Number PCT/US2023/025475, filed Jun. 15, 2023, which claims priority to U.S. Provisional Patent Application No. 63/352,458 filed on Jun. 15, 2022 and U.S. Provisional Patent Application No. 63/492,180 filed on Mar. 24, 2023, the entire contents of each of which are hereby incorporated by reference.

FEDERALLY SPONSORED RESEARCH

This invention was made with government support under MH117055 awarded by the National Institutes of Health. The government has certain rights in the invention.

REFERENCE TO AN ELECTRONIC SEQUENCE LISTING

The contents of the electronic sequence listing (028193-0004-WO01_Sequence_Listing.xml; Size: 36,864 bytes; and Date of Creation: Jun. 15, 2023) is herein incorporated by reference in its entirety.

TECHNICAL FIELD

This disclosure relates to protein-RNA structures that can be used for high-throughput protein display.

INTRODUCTION

Library display technologies can enable the development of peptides with affinity for a given substrate. However, technical issues have limited application of library display to larger proteins. For example, Phage Display—the most established library-display approach—was applied to the SNAP covalent capture protein. However, this only produced variants with poor capture efficiency. Furthermore, unlike short peptides, covalent-capture proteins should fold into a complex three-dimensional structure for proper function. The energetics of folding can depend on residues distributed throughout the entire protein, while the efficacy of ligand capture can depend on residues that line the active pocket. Full exploration of active-pocket variants can be challenging because the number of combinatorial mutations is enormous, and because mutations that improve active-pocket efficiency may disrupt the global energetics of protein folding.

Over the past three decades, several display systems have been developed, each with a unique set of limitations (FIG. 1A and FIG. 1B). For example, in vivo systems such as Phage Display provide useful genotype/phenotype linkage stability owing to the use of an intact viral particle, but the library size is limited to ~$10^9$ variants because of the need for bacterial transformation. Cell-free in vitro systems can overcome this barrier, offering a hypothetical library size on the order of ~$10^{14}$, but have other shortcomings that have hindered their utility. For example, ribosome display uses the ribosome itself to maintain a markedly unstable linkage. Finally, mRNA display is an in vitro system in which each mRNA is covalently attached to its corresponding protein. But, inefficiencies in the covalent-attachment procedure cause library-size reductions, and the approach can be complicated, time-consuming, and difficult to establish across labs.

SUMMARY

In one aspect, disclosed are nucleic acids comprising, in an upstream to downstream direction: a first portion comprising a nucleotide sequence encoding an RNA including at least 2 RNA hairpin domains, the RNA forming hairpin structures that correspond in number to the RNA hairpin domains, wherein each hairpin structure includes a stem and a loop, and wherein each individual RNA hairpin domain is located in a separate and individual loop; a second portion comprising a nucleotide sequence encoding a protein including at least 2 RNA hairpin binding peptides, wherein each individual RNA hairpin binding peptide is orientated to specifically bind to a separate and individual RNA hairpin domain; and a third portion comprising a nucleotide sequence encoding a protein of interest, wherein the third portion is operably coupled to the first portion and the second portion.

In another aspect, disclosed are nucleic acids comprising, in an upstream to downstream direction: a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop; a second portion comprising a nucleotide sequence encoding a protein including at least 2 lambda bacteriophage anti-terminator protein N domains (λ domain), wherein each individual λ domain is orientated to specifically bind to a separate and individual boxB domain; and a third portion comprising a nucleotide sequence encoding a protein of interest, wherein the third portion is operably coupled to the first portion and the second portion.

In another aspect, disclosed are nucleic acids comprising, in an upstream to downstream direction: a first portion comprising a nucleotide sequence encoding an RNA including 4 boxB domains, the RNA forming hairpin structures that correspond in number to the boxB domains, wherein each hairpin structure includes a stem and a loop, wherein each individual boxB domain is located in a separate and individual loop, and wherein the nucleotide sequence of the first portion includes a nucleotide sequence selected from the group consisting of SEQ ID NO:14, SEQ ID NO:15, SEQ ID NO:16, SEQ ID NO:17, and a combination thereof; a second portion comprising a nucleotide sequence encoding a protein including 4λ domains, wherein each individual λ domain is orientated to specifically bind to a separate and individual boxB domain; and a third portion comprising a nucleotide sequence encoding a protein of interest, wherein the third portion is operably coupled to the first portion and the second portion.

In another aspect, disclosed are nucleic acids comprising, in an upstream to downstream direction: a first portion comprising a nucleotide sequence encoding an RNA including 3 boxB domains, the RNA forming hairpin structures that correspond in number to the boxB domains, wherein each hairpin structure includes a stem and a loop, wherein each individual boxB domain is located in a separate and individual loop, and wherein the nucleotide sequence of the first portion includes a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof; a second portion comprising a nucleotide sequence encoding a protein including a scaffold protein and 3λ domains extending from the scaffold protein, wherein each individual λ domain is orientated to specifically bind to a separate and individual boxB domain; and a third portion comprising a nucleotide sequence encoding a protein of interest, wherein the third portion is operably coupled to the first portion and the second portion.

In another aspect, disclosed are protein-RNA display constructs comprising: a first nucleotide portion comprising an RNA including at least 2 RNA hairpin domains, the RNA forming hairpin structures that correspond in number to the RNA hairpin domains, wherein each hairpin structure includes a stem and a loop, and wherein each individual RNA hairpin domain is located in a separate and individual loop; a second nucleotide portion comprising an mRNA encoding a protein of interest, wherein the second nucleotide portion is coupled to the first nucleotide portion; a first protein portion comprising a protein including at least 2 RNA hairpin binding peptides, wherein each individual RNA hairpin binding peptide is orientated to specifically bind to a separate and individual RNA hairpin domain; and a second protein portion comprising the protein of interest, wherein the second protein portion is coupled to the first protein portion.

In another aspect, disclosed are protein-RNA display constructs comprising: a first nucleotide portion comprising an RNA including at least 2 boxB domains, the RNA forming hairpin structures that correspond in number to the boxB domains, wherein each hairpin structure includes a stem and a loop, and wherein each individual boxB domain is located in a separate and individual loop; a second nucleotide portion comprising an mRNA encoding a protein of interest, wherein the second nucleotide portion is coupled to the first nucleotide portion; a first protein portion comprising a protein including at least 2 lambda bacteriophage anti-terminator protein N domains (λ domain), wherein each individual λ domain is orientated to specifically bind to a separate and individual boxB domain; and a second protein portion comprising the protein of interest, wherein the second protein portion is coupled to the first protein portion.

In another aspect, disclosed are protein-RNA display constructs comprising a first nucleotide portion comprising an RNA including 4 boxB domains, the RNA forming hairpin structures that correspond in number to the boxB domains, wherein each hairpin structure includes a stem and a loop, wherein each individual boxB domain is located in a separate and individual loop, and wherein the RNA includes a nucleotide sequence selected from the group consisting of SEQ ID NO:14, SEQ ID NO:15, SEQ ID NO:16, SEQ ID NO:17, and a combination thereof; a second nucleotide portion comprising an mRNA encoding a protein of interest, wherein the second nucleotide portion is coupled to the first nucleotide portion; a first protein portion comprising a protein including 4λ domains, wherein each individual λ domain is orientated to specifically bind to a separate and individual boxB domain; and a second protein portion comprising the protein of interest, wherein the second protein portion is coupled to the first protein portion.

In another aspect, disclosed are protein-RNA display constructs comprising a first nucleotide portion comprising an RNA including 3 boxB domains, the RNA forming hairpin structures that correspond in number to the boxB domains, wherein each hairpin structure includes a stem and a loop, wherein each individual boxB domain is located in a separate and individual loop, and wherein the RNA includes a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof; a second nucleotide portion comprising an mRNA encoding a protein of interest, wherein the second nucleotide portion is coupled to the first nucleotide portion; a first protein portion comprising a protein including a scaffold protein and 3λ domains extending from the scaffold protein, wherein each individual λ domain is orientated to specifically bind to a separate and individual boxB domain; and a second protein portion comprising the protein of interest, wherein the second protein portion is coupled to the first protein portion.

In another aspect, disclosed are nucleic acids comprising, in an upstream to downstream direction: a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop; a second portion comprising a nucleotide sequence encoding a protein including at least 2 lambda bacteriophage anti-terminator protein N domains (λ domain), wherein each individual λ domain is orientated to specifically bind to a separate and individual boxB domain; and a cloning site for insertion of a nucleotide sequence encoding a protein of interest, the cloning site operably coupled to the first portion and the second portion.

In another aspect, disclosed are libraries of protein-RNA display constructs comprising a plurality of protein-RNA display constructs as disclosed herein.

In another aspect, disclosed are kits comprising a disclosed nucleic acid, protein-RNA display construct, or a combination thereof; and one or more packages, receptacles, labels, or instructions for use.

In another aspect, disclosed are methods of performing high throughput proteomics, the method comprising: (a) expressing one or more of the nucleic acids as disclosed herein, thereby producing a library of protein-RNA display constructs as disclosed herein, wherein the protein of interest is coupled to the mRNA encoding the protein of interest; (b) contacting the library of protein-RNA display constructs with a target molecule; (c) identifying at least one protein of interest that specifically binds to the target molecule; and (d) optionally sequencing the mRNA encoding the at least one protein of interest that specifically binds to the target molecule.

BRIEF DESCRIPTION OF THE DRAWINGS

FIG. 1A-FIG. 1B show an overview of protein display. (FIG. 1A) An important feature of protein display is construction of a large library of protein variants, where each displayed protein (phenotype) is linked to its corresponding mRNA (genotype). During iterative selection (panning), selection pressure is applied to enrich a protein subpopulation based on the affinity to the target molecule. (FIG. 1B) Schematic summary of different protein display technologies.

(FIG. 3A) Experimental design for linkage stability evaluation. (FIG. 3B & FIG. 3C) 4 tandem boxB/λ provides a stable mRNA/protein linkage. (FIG. 3D) Linkage stability evaluation of two different versions of 3 boxB-λ (active HaloTag (HT) to inactive HT were mixed 1 to 9 proportions).

(FIG. 4A) Useful locations for boxB tandems were found via moving the tandems along the plasmid and evaluating the corresponding mRNA/protein linkage fidelity (1:1 active:inactive HT mix) (FIG. 4B) Useful locations for λ tandems were found via evaluation of protein expression and mRNA/protein linkage fidelity at different locations (1:9 HT mix). Improvement of linker composition (FIG. 4C) between λ tandems and linker length (FIG. 4D) was done based on 2boxB-λ tandem construct (1:1 HT mix).

(FIG. 5A) The mRNA/HT-GFP complexes in Ribosome and GRIP Display were isolated on HTL-conjugated beads. The GFP signal on the beads was used to quantify the number of proteins/uL beads. The amount of mRNA material/uL beads was quantified via RT-qPCR. N=3, mean+/−SE; * $p<0.001$; two-tailed paired t-test; (FIG. 5B) The ratio of mRNA/protein was calculated using the data from FIG. 5A. N=3, mean+/−SE;  $p<0.01$. two-tailed paired t-test.

(FIG. 6A) Bacterial colonies expressed folding reporter GFP and HT protein variant (active HT-expressing colonies appear lighter in this image). The plates were imaged via Ix83 and TMR signal was evaluated. N=4 plates for before and N=3 plates for after pan. (FIG. 6B) The TMR signal of the colonies was plotted. N=1176 colonies (before), N=827 colonies (after pan). A significant enrichment for active HT colonies was observed, appearing as pronounced bi-modal distribution. (FIG. 6C) Each plate was evaluated for the % of HaloTag-expressing colonies with various activity levels (Log TMR>3). A 10-fold enrichment of wild type (WT) protein is achieved in a single pan. (FIG. 6D) Each plate was evaluated for the % of WT HaloTag-expressing colonies (Log TMR>5.5, estimated from positive control plates). A 10-fold enrichment of WT protein was achieved in a single pan. N=4, N=3, mean+1 SD;  $p<0.01$ ** $p<0.0001$; two-tailed t-test, equal variances.

(FIG. 7A) Active HT was mixed with its inactive form in 1:100 ratio, resulting in 1% active library. A round of panning was performed using GRIP Display and HTL magnetic beads. The isolated DNA material was transformed into T7 bacteria and plated on isopropyl ß-D-1-thiogalactopyranoside (IPTG) and HTL-fluorescent dye containing plates; (FIG. 7B) The normalized TMR signal of the colonies was plotted. N=2982 colonies (before), N=4040 colonies (after pan). A significant enrichment for active HT colonies is observed, appearing as pronounced bi-modal distribution. (FIG. 7C) The ratio of colonies containing active HT to total colonies was calculated. N=18 plates; mean+/1 SE; ** $p<0.0001$, two-tailed paired t-test. (FIG. 7D) After 1 round of pan, the PCR material of the pseudo-libraries was digested with a restriction enzyme (RE) and the active HTP band was separated from inactive HTP in 1% agarose gel. The intensity of each band was measured via gel image processing in Matlab, and the live:total ratio calculated. The data was normalized for the length of the band. (FIG. 7**E) The pseudo-library size (inversely proportional to the starting activity) was plotted against the enrichment of the library after 1 pan using GRIP. 1 Display. Black line represents maximum possible enrichment for each corresponding library. N=3.

(FIG. 8A) Rounds of panning were performed on 4NNS HTP library using GRIP Display and HTL magnetic beads. The isolated DNA material was transformed into T7 bacteria and plated on IPTG and HTL-fluorescent dye containing plates. The resulting signal was evaluated and compared to the WT HTP signal. The normalized TMR signal of the colonies was plotted. N=10 plates before pan, N=12 plates each pan, N=3 plates for control plates. Percent of colonies after each pan, having TMR signal comparable to positive control. (FIG. 8B) Normalized TMR signal of several sequenced variants, re-plated separately. (FIG. 8C) Dose-response curves were evaluated by incubating the neurons expressing a particular variant with biotinylated HTL for 15 min, followed by washing, fluorescent labeling of biotin and imaging.

(FIG. 9A) The heat map representing the relative abundance of each of the 21 possible residues at each mutated location, based on Amplicon NGS data. This is the unpanned library. The residues of the wild-type HTP are outlined in yellow (FIG. 9B) Four rounds of bio-panning were performed on 6NNS HTP library using GRIP Display and HTL magnetic beads. The NGS of the isolated DNA material is plotted as a heat map. The emergence of several types of novel protein families and their relative abundance. Two of the most prominent variants were modeled in PyMol based on the crystal structure of the wild-type HTP and HTL.

(FIG. 12A) Schematic representation of the GFP as a scaffold and the insertion of λ peptides with various adjacent linkers and helices. (FIG. 12B and FIG. 12C) A 3-D representation of the resulting $\lambda_{CLAW}$ and the color-coded locations of the variations in the CLAW library. (FIG. 12D) The assembly of the GRIP.2 components: $boxB_{Toy}$ and $\lambda_{CLAW}$.

(FIG. 13A) qPCR quantification of the isolated mRNA after panning either 1:1 ratio of active:inactive HTP or 100% active HTP with HTL-beads. The data is pooled from 3 different experiments with triplicates per each experiment. (FIG. 13B) Statistical analysis on data in FIG. 13A. (FIG. 13C) GRIP.1 and GRIP.2 have no statistically significant difference in enrichment. The P value of the two-sided permutation t-test is 0.563. The mean difference between GRIP.2 against GRIP.1 is shown in Cumming estimation plots. The raw data is plotted on the left axes. On the right axes, mean differences are plotted as bootstrap sampling distributions. Each 95% confidence interval is indicated by the ends of the vertical error bars. (FIG. 13D) "Cross talk" evaluation as a function of temperature. 1:9 active:inactive HTP were mixed as proteins or DNA, based on agarose gel assay.

(FIG. 14A) Claw-Toy design maintains 40% of its mRNA after 1 hour wash at 37° C. compared to 4° C. In comparison, 4boxB-λ design loses 90% of its mRNA. (FIG. 14B) Claw-Toy design is resistant to large concentrations of detergents, while 4boxB-λ design loses ¾ of its total mRNA. (FIG. 14C) Both GRIP.1 and GRIP.2 versions are unaffected by high salt concentrations.

(FIG. 15A) GRIP. 1 has the same level of protein expression regardless of the RNA-peptide complex presence. (FIG. 15B) In the presence of CLAW-Toy interaction, the green fluorescent signal was inhibited, indicating a self-inhibition due to RBS occlusion. In absence of Toy, the signal increases with increased time of expression. (FIG. 15C) The self-inhibitory function depends on the presence of CLAW. When it is substituted with another RNA trimer 3boxB, the function decreases.

DETAILED DESCRIPTION

Figure 1A:
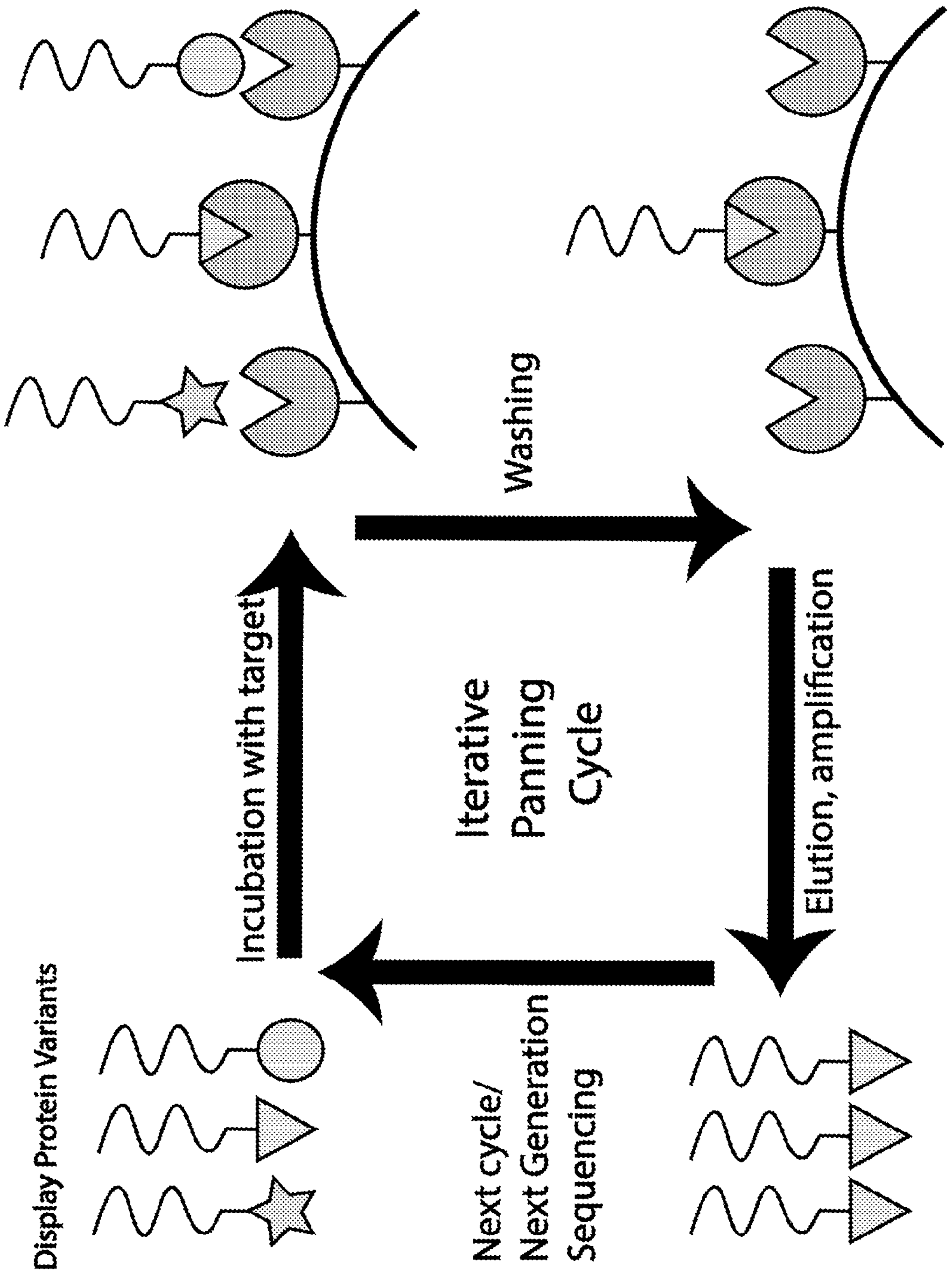

The present disclosure is based, in part, on the discovery of a novel protein display technology termed "GRIP Display" (Gluing RNA to Its Protein). The system and methods provided herein leverage the tight interaction between a λ peptide and boxB RNA hairpin borrowed from viruses. The systems and methods provided herein represent the first use of the λ-boxB system peptide/RNA interaction in a library display context. GRIP Display provided herein is simple and easy to establish in any lab setting and is suitable for the development of numerous compounds, including but not limited to, functional antibodies, short and long peptides, as well as large proteins and enzymes. Furthermore, the systems and methods provided herein eliminate the trade-off between library size, linkage stability, and ease of use.

1. Definitions

Unless otherwise defined, all technical and scientific terms used herein have the same meaning as commonly understood by one of ordinary skill in the art. In case of conflict, the present document, including definitions, will control. The materials, methods, and examples disclosed herein are illustrative only and not intended to be limiting. Methods and materials similar or equivalent to those described herein can be used in practice or testing of the disclosed invention. All publications, patent applications, patents and other references mentioned herein are incorporated by reference in their entirety.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are contemplated, and for the range 1.5-2, the numbers 1.5, 1.6, 1.7, 1.8, 1.9, and 2 are contemplated.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

The term "boxB domain," as used herein, refers to a 15-nucleotide hairpin stem-loop sequence that specifically binds to a lambda bacteriophage anti-terminator protein N domain.

The term "lambda bacteriophage anti-terminator protein N domain," as used herein, refers to a 22 amino acid sequence that specifically binds to a boxB domain.

"Genetic construct" as used herein refers to DNA or RNA molecules that comprise a polynucleotide that encodes a protein, RNA, or combination thereof. The coding sequence includes initiation and termination signals operably linked to regulatory elements including a promoter and optionally a polyadenylation signal capable of directing expression. As used herein, the term "expressible form" refers to gene constructs that contain the necessary regulatory elements operably linked to a coding sequence that encodes a protein such that when present, the coding sequence will be expressed.

As used herein, "encode", "encoded", "encoding" and the like refer to principle that DNA can be transcribed into RNA, which can then optionally be translated into amino acid sequences that can form proteins.

The term "heterologous" as used herein refers to nucleic acids comprising two or more subsequences that are not found in the same relationship to each other in nature. For instance, a nucleic acid that is recombinantly produced typically has two or more sequences from unrelated genes synthetically arranged to make a new functional nucleic acid, for example, a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include a non-native (non-naturally occurring) nucleic acid that has integrated into the chromosome, or a non-native (non-naturally occurring) extrachromosomal nucleic acid. Similarly, a heterologous protein indicates that the protein comprises two or more subsequences that are not found in the same relationship to each other in nature (for example, a "fusion protein," where the two subsequences are encoded by a single nucleic acid sequence).

"Nucleic acid" or "oligonucleotide" or "polynucleotide" as used herein means at least two nucleotides covalently linked together. The depiction of a single strand can also define the sequence of the complementary strand. Thus, a polynucleotide can also encompass the complementary strand of a depicted single strand. Many variants of a polynucleotide may be used for the same purpose as a given polynucleotide. Thus, a polynucleotide also encompasses substantially identical polynucleotides and complements thereof. A single strand provides a probe that may hybridize to a target sequence under stringent hybridization conditions. Thus, a polynucleotide can also encompass a probe that hybridizes under stringent hybridization conditions. Polynucleotides may be single stranded or double stranded or may contain portions of both double stranded and single stranded sequence. The polynucleotide can be nucleic acid, natural or synthetic, DNA, genomic DNA, cDNA, RNA (e.g., mRNA), or a hybrid, where the polynucleotide can contain combinations of deoxyribo- and ribo-nucleotides, and combinations of bases including, for example, uracil, adenine, thymine, cytosine, guanine, inosine, xanthine hypoxanthine, isocytosine, and isoguanine. Polynucleotides can be obtained by chemical synthesis methods or by recombinant methods.

As used interchangeably herein, "operatively coupled" and "operably coupled" in the context of recombinant or engineered polynucleotide molecules (e.g. DNA and RNA) vectors, and the like refers to the regulatory and other sequences useful for expression, stabilization, replication, and the like of the coding and transcribed non-coding sequences of a nucleic acid that are placed in the nucleic acid molecule in the appropriate positions relative to the coding sequence so as to affect expression or other characteristic of the coding sequence or transcribed non-coding sequence. This same term can be applied to the arrangement of coding sequences, non-coding and/or transcription control elements (e.g., promoters, enhancers, and termination elements), and/or selectable markers in an expression vector. "Coupled" can also refer to an indirect attachment (e.g., not a direct fusion) of two or more polynucleotides, two or more polypeptides, or a polynucleotide and a polypeptide to each other via a linking molecule (e.g., such as a linker or a complex as disclosed herein).

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins and receptors. The terms "polypeptide", "protein," and "peptide" are used interchangeably herein. "Primary structure" refers to the amino acid sequence of a particular peptide. "Secondary structure" refers to locally ordered, three dimensional structures within a polypeptide. These structures are commonly known as domains, for example, enzymatic domains, extracellular domains, transmembrane domains, pore domains, and cytoplasmic tail domains. "Domains" are portions of a polypeptide that form a compact unit of the polypeptide and are typically 10 to 350 amino acids long. Exemplary domains include domains with enzymatic activity or binding activity (e.g., boxB domain). Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. In some embodiments, a motif includes 3, 4, 5, 6, or 7 sequential amino acids. λ domain may be comprised of a series of the same type of motif.

"Promoter" as used herein means a synthetic or naturally derived molecule which is capable of conferring, activating or enhancing expression of a nucleic acid. A promoter may comprise one or more specific transcriptional regulatory sequences to further enhance expression and/or to alter the spatial expression and/or temporal expression of the same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to the cell, the tissue or organ in which expression occurs or, with respect to the developmental stage at which expression occurs, or in response to external stimuli such as physiological stresses, pathogens, metal ions, or inducing agents.

The term "small molecule," as used herein, refers to inorganic or organic compounds having a molecular weight of less than 3,000 Daltons.

The term "recombinant" when used with reference to, for example, a cell, nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed, or not expressed at all.

As used herein, the term "specifically binds" is generally meant that a molecule binds to a target molecule when it binds to that target molecule more readily than it would bind to a random, unrelated target.

"Substantially identical" means that a first and second sequence, such as an amino acid sequence or a nucleotide sequence, are at least 60%, 65%, 70%, 75%, 80%, 85%, 90%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, or 1100 amino acids or nucleotides. This can also be referred to as X % sequence identity, where a first and second sequence are at least X % identical over a region of amino acids or nucleotides as listed above. In some embodiments, the region of amino acids or nucleotides is the entire sequence(s).

"Vector" as used herein means a nucleic acid sequence containing an origin of replication. A vector may be a viral vector, bacteriophage, bacterial artificial chromosome, or yeast artificial chromosome. A vector may be a DNA or RNA vector. A vector may be a self-replicating extrachromosomal vector, and preferably, is a DNA plasmid.

2. Protein-RNA Display Constructs

Provided herein are protein-RNA display constructs where the protein-RNA display construct includes a protein of interest and its cognate mRNA sequence (e.g., the mRNA sequence encoding the protein of interest) coupled to each other. The coupling of the protein of interest and its cognate mRNA is accomplished by a non-covalent binding tandem that includes an RNA hairpin domain and an RNA hairpin binding peptide (also referred to as a complex of the RNA hairpin domains and the RNA hairpin binding peptides). Example tandems include, but are not limited to, lambda bacteriophage anti-terminator protein N domain (λ domain) and boxB; variations of the λ domain (e.g., $\lambda_{N22}$) and boxB; P22 and boxB; N-terminal zinc knuckle of RSV (Rous sarcoma virus) with nucleocapsid with hairpin stem-loop from RSV $M_\varphi$ packaging signal; and MS2 coat protein and its AUUA RNA hairpin. By using the avidity of a plurality of binding tandems, the protein-RNA display construct can withstand conditions used in, e.g., panning, as well as can provide high fidelity of the cognate mRNA being coupled to its corresponding protein of interest.

Figure 17:
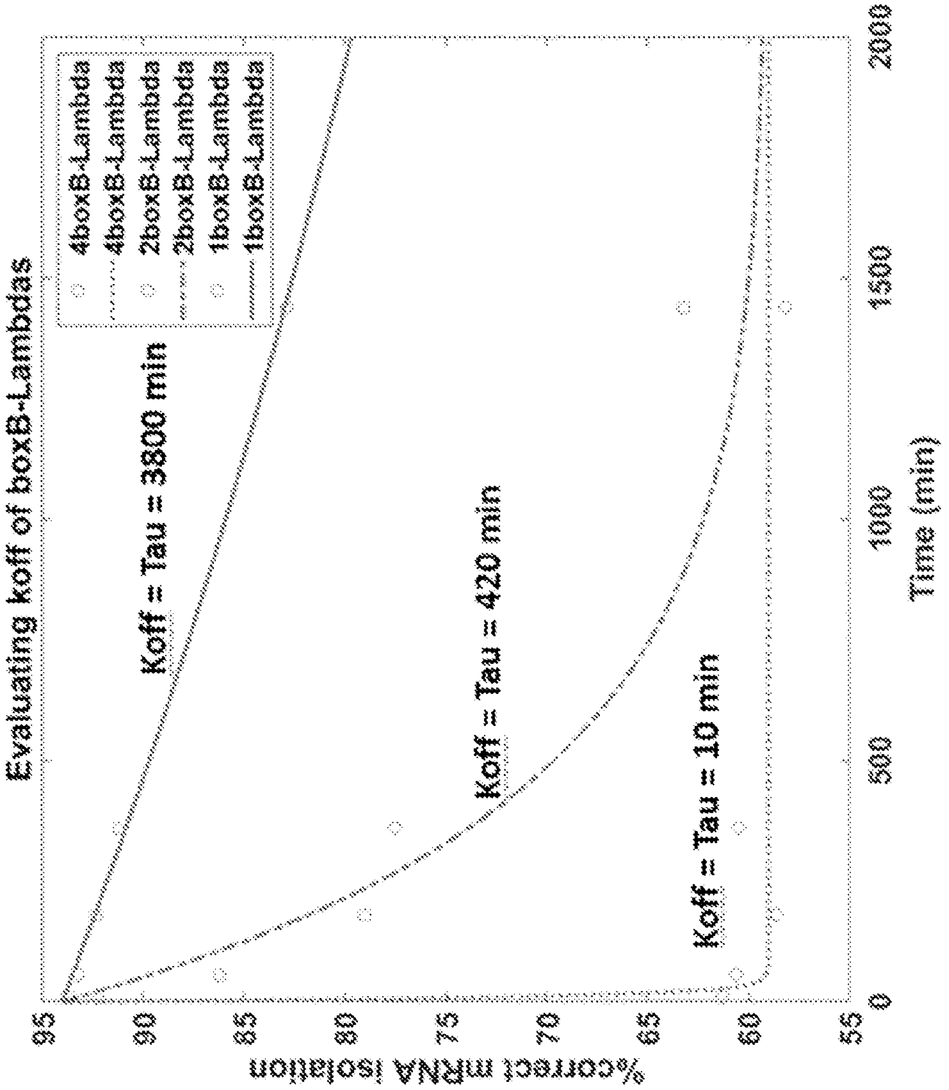
FIG. 17 shows experimental evaluation of $k_{off}$ (time constant) of 4boxb-λ, 2boxB-λ and 1boxB-λ, with the tetrameric construct having over 63 hour of mRNA-peptide stability compared to the 10 min release time of the single RNA-peptide pair.

The specific binding between the RNA hairpin domain and the RNA hairpin binding peptide can result in a stably coupled mRNA sequence and its expressed protein. The stable coupling can be described as the $k_{off}$ of the binding between the plurality of RNA hairpin domains (e.g., at least 2 boxB domains) and the plurality of RNA binding peptides (e.g., at least 2λ domains). For example, the complex formed between a plurality of RNA hairpin domains and RNA hairpin binding peptides can have a $k_{off}$ of greater than 50 minutes, greater than 100 minutes, greater than 200 minutes, greater than 300 minutes, greater than 400 minutes, greater than 500 minutes, greater than 1,000 minutes, greater than 1,500 minutes, greater than 2,000 minutes, greater than 2,500 minutes, greater than 3,000 minutes, greater than 3,500 minutes, or greater than 4,000 minutes. In some embodiments, the complex has a $k_{off}$ of less than 10,000 minutes, less than 8,000 minutes, less than 6,000 minutes, or less than 4,000 minutes. In some embodiments, the complex has a $k_{off}$ of about 50 minutes to about 10,000 minutes, such as about 100 minutes to about 8,000 minutes, about 300 minutes to about 5,000 minutes, or about 400 minutes to about 4,000 minutes. The $k_{off}$ associated with the protein-RNA display construct can be measured as described in the Examples below and shown in FIG. 17.

The disclosed protein-RNA display construct can include at least four different portions. For example, the protein-RNA display construct can include two different nucleotide portions and two different protein portions, such as a first nucleotide portion, a second nucleotide portion, a first protein portion, and a second protein portion. The protein-RNA display construct can further include a reporter construct. Example reporter constructs include, but are not limited to, lacZ (b-galactosidase), xylE (catechol 2,3-dioxygenase), lux (bacterial luciferase), luc (insect luciferase), phoA (alkaline phosphatase), gusA and gurA (beta-glucuronidase), GFP (green fluorescent protein), mCherry, dTomato, EGFP (Enhanced green fluorescent protein), DsRed (*Discosoma* sp. red fluorescent protein), Hygro (hygromycin), bla (beta-lactamase) and other antibiotic resistance markers, and the like. In some embodiments, the reporter construct comprises a fluorescent protein. In some embodiments, the reporter construct is a fluorescent protein.

A. First Nucleotide Portion

The first nucleotide portion can include an RNA that includes a plurality of RNA hairpin domains. The RNA can form hairpin structures that correspond in number to the number of RNA hairpin domains. Each RNA hairpin structure includes a loop and a stem. Each individual RNA hairpin domain can be located in a separate and individual loop of the RNA hairpin structure. The stem can be modified to improve binding between the RNA hairpin domain and the RNA hairpin binding peptide. An example stem modification includes, but is not limited to, an extension. The stem for each loop can be 4 to 30 base pairs, such as 4 to 20 base pairs, 4 to 15 base pairs, or 5 to 8 base pairs.

A number of RNA hairpin domains can be used in the RNA. Example RNA hairpin domains include, but are not limited to, boxB domains, nucleocapsid with hairpin stem-loop from RSV $M_\varphi$ packaging signal, and a MS2 coat protein's corresponding AUUA RNA hairpin. In some embodiments, the RNA hairpin domain includes a boxB domain. In some embodiments, the RNA hairpin domain is a boxB domain.

The RNA can include a varying number of RNA hairpin domains. For example, the RNA can include 2 to 20 RNA hairpin domains, such as 2 to 18 RNA hairpin domains, 2 to 16 RNA hairpin domains, 2 to 14 RNA hairpin domains, 2 to 12 RNA hairpin domains, 2 to 10 RNA hairpin domains, 2 to 8 RNA hairpin domains, 2 to 6 RNA hairpin domains, or 2 to 4 RNA hairpin domains. In some embodiments, the RNA includes at least 2 RNA hairpin domains, at least 4 RNA hairpin domains, at least 6 RNA hairpin domains, at least 8 RNA hairpin domains, at least 10 RNA hairpin domains, or at least 12 RNA hairpin domains. In some embodiments, the RNA includes less than 20 RNA hairpin domains, less than 18 RNA hairpin domains, less than 16 RNA hairpin domains, less than 14 RNA hairpin domains, less than 12 RNA hairpin domains, or less than 10 RNA hairpin domains.

The first nucleotide portion can include a plurality of boxB domains in RNA hairpin structures. For example, the first nucleotide portion can include an RNA including at least 2 boxB domains, the RNA forming hairpin structures that correspond in number to the boxB domains, wherein each hairpin structure includes a stem and a loop, and wherein each individual boxB domain is located in a separate and individual loop.

The first nucleotide portion can include an RNA having a varying number of boxB domains. For example, the RNA can include 2 to 20 boxB domains, such as 2 to 18 boxB domains, 2 to 16 boxB domains, 2 to 14 boxB domains, 2 to 12 boxB domains, 2 to 10 boxB domains, 2 to 8 boxB domains, 2 to 6 boxB domains, or 2 to 4 boxB domains. In some embodiments, the RNA includes at least 2 boxB domains, at least 4 boxB domains, at least 6 boxB domains, at least 8 boxB domains, at least 10 boxB domains, or at least 12 boxB domains. In some embodiments, the RNA includes less than 20 boxB domains, less than 18 boxB domains, less than 16 boxB domains, less than 14 boxB domains, less than 12 boxB domains, or less than 10 boxB domains.

The RNA can include a nucleotide sequence having at least 80%, 85%, 90%, 95%, 99%, or about 100% identity to SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. The RNA can also include a combination of the foregoing nucleotide sequences.

In some embodiments, the RNA includes a nucleotide sequence selected from the group consisting of SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof.

B. Second Nucleotide Portion

The second nucleotide portion can include an mRNA encoding a protein of interest. The mRNA encoding the protein of interest is not limited and can include any mRNA that can be used with the disclosed nucleic acids. The second nucleotide portion can be coupled to the first nucleotide portion. The second nucleotide portion can be directly coupled to the first nucleotide portion or can be coupled to the first nucleotide portion through a linker. The second nucleotide portion can also include an mRNA encoding the first protein portion (e.g., plurality of RNA hairpin binding peptides). Accordingly, the first protein portion and the second protein portion can be a fusion protein.

C. First Protein Portion

The first protein portion can include a protein that includes a plurality of RNA hairpin binding peptides. Each individual RNA hairpin binding peptide can be orientated to specifically bind to a separate and individual RNA hairpin domain. A number of RNA hairpin binding peptides can be included in the protein. Example peptides include, but are not limited to, λ domains, variations of λ domains (e.g., $\lambda_{N22}$), N-terminal zinc knuckle of RSV (Rous sarcoma virus), and MS2 coat proteins. In some embodiments, the RNA hairpin binding peptide includes a λ domain. In some embodiments, the RNA hairpin binding peptide is a λ domain.

The protein can include a varying number of RNA hairpin binding peptides. For example, the protein can include 2 to 20 RNA hairpin binding peptides, such as 2 to 18 RNA hairpin binding peptides, 2 to 16 RNA hairpin binding peptides, 2 to 14 RNA hairpin binding peptides, 2 to 12 RNA hairpin binding peptides, 2 to 10 RNA hairpin binding peptides, 2 to 8 RNA hairpin binding peptides, 2 to 6 RNA hairpin binding peptides, or 2 to 4 RNA hairpin binding peptides. In some embodiments, the protein includes at least 2 RNA hairpin binding peptides, at least 4 RNA hairpin binding peptides, at least 6 RNA hairpin binding peptides, at least 8 RNA hairpin binding peptides, at least 10 RNA hairpin binding peptides, or at least 12 RNA hairpin binding peptides. In some embodiments, the protein includes less than 20 RNA hairpin binding peptides, less than 18 RNA hairpin binding peptides, less than 16 RNA hairpin binding peptides, less than 14 RNA hairpin binding peptides, less than 12 RNA hairpin binding peptides, or less than 10 RNA hairpin binding peptides.

The protein can include a plurality of λ domains. For example, the first protein portion can include a protein including at least 2λ domains, wherein each individual λ domain is orientated to specifically bind to a separate and individual boxB domain.

The first protein portion can include a protein having a varying number of λ domains. For example, the protein can include 2 to 20λ domains, such as 2 to 18λ domains, 2 to 16λ domains, 2 to 14λ domains, 2 to 12λ domains, 2 to 10λ domains, 2 to 8λ domains, 2 to 6λ domains, or 2 to 4λ domains. In some embodiments, the protein includes at least 2λ domains, at least 4λ domains, at least 6λ domains, at least 8λ domains, at least 10λ domains, or at least 12λ domains. In some embodiments, the protein includes less than 20λ domains, less than 18λ domains, less than 16λ domains, less than 14λ domains, less than 12λ domains, or less than 10λ domains. In some embodiments, the protein includes a number of λ domains that correspond in number to the number of boxB domains. For example, in some embodiments, the protein can include 2 to 4λ domains and the RNA can include 2 to 4 boxB domains.

The protein can include a scaffold protein. The scaffold protein can facilitate orientation of the λ domains such that it can easily and specifically bind to its corresponding boxB domain. Example scaffold proteins include, but are not limited to, fluorescent proteins (e.g., GFP), DARPINs, fibronectins, and nanobodies. The scaffold protein can have a varying number of λ domains extending from it, such as any of the numbers described above. In some embodiments, the scaffold protein has 3λ domains extending from it. The scaffold protein can have a plurality of loops (e.g., 2 to 12) and a plurality of beta sheets (e.g., 2 to 12). The scaffold protein may also include 1 to 3 loop helices. The loop helix may include an amino acid sequence of SEQ ID NO:23. In some embodiments, each individual λ domain extends from a separate and individual loop of the scaffold protein.

The scaffold protein can have a varying molecular weight. For example, the scaffold protein can have a molecular weight of about 10 kilodaltons (kDa) to about 40 kDa, such as about 15 kDa to about 35 kDa, about 20 kDa to about 30 kDa, about 10 kDa to about 25 kDa, or about 25 kDa to about 40 kDa. In some embodiments, the scaffold protein has a molecular weight of greater than 10 kDa, greater than 15 kDa, or greater than 20 kDa. In some embodiments, the scaffold protein has a molecular weight of less than 40 kDa, less than 35 kDa, or less than 30 kDa.

The protein can include linkers between λ domains. For example, in embodiments where the protein includes 3λ domains, the protein can include two linkers (e.g., λ domain-linker-λ domain-linker-λ domain). The linker can be any suitable linker used in the art for protein chemistry. Example linker sequences include, but are not limited to, $SSGSS_n$ (SEQ ID NO:38), $GGSGG_n$ (SEQ ID NO:39), and $(G)_n$ (SEQ ID NO:40), wherein n is 1 to 100, such as 1 to 50, 1 to 20, 1 to 10, 1 to 8, or 1 to 5. In some embodiments, the linker is $GGSGG_n$ SEQ ID NO:39.

The linker can include a varying number of amino acids. For example, the linker can include 1 amino acid to 100 amino acids, such as 2 amino acids to 75 amino acids, 5 amino acids to 50 amino acids, 50 amino acids to 100 amino acids, 1 amino acid to 50 amino acids, or 2 amino acids to 30 amino acids. In some embodiments, the linker includes greater than 1 amino acid, greater than 10 amino acids, greater than 20 amino acids, or greater than 50 amino acids. In some embodiments, the linker includes less than 100 amino acids, less than 75 amino acids, less than 50 amino acids, or less than 25 amino acids.

The protein can include an amino acid sequence having at least 80%, 85%, 90%, 95%, 99%, or about 100% identity to SEQ ID NO:2, SEQ ID NO:4, SEQ ID NO:6, SEQ ID NO:8, SEQ ID NO:10, SEQ ID NO:12, SEQ ID NO:13, or SEQ ID NO:22. The protein can also include a combination of the foregoing amino acid sequences.

In some embodiments, the protein includes an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:13, SEQ ID NO:22, and a combination thereof.

D. Second Protein Portion

The second protein portion can include the protein of interest. The protein of interest can be generally any protein that can be expressed via the nucleic acids disclosed herein. Example proteins of interest include, but are not limited to, antibodies, nanobodies, receptors, enzymes, large molecular weight proteins (e.g., ≥10 kDa), and small molecular weight proteins (e.g., ≤10 kDa). In some embodiments, the protein of interest comprises one or more deletions, insertions, or substitutions compared to its wild type protein. The second protein portion can be coupled to the first protein portion. The second protein portion can be directly coupled to the first protein portion or can be coupled to the first protein portion through a linker as described herein. In some embodiments, the second protein portion is coupled to the first protein portion through a linker.

E. Example Protein-RNA Display Constructs

In some embodiments, the protein-RNA display construct includes a first nucleotide portion comprising an RNA including 4 boxB domains, the RNA forming hairpin structures that correspond in number to the boxB domains, wherein each hairpin structure includes a stem and a loop, wherein each individual boxB domain is located in a separate and individual loop, and wherein the RNA includes a nucleotide sequence selected from the group consisting of SEQ ID NO:14, SEQ ID NO:15, SEQ ID NO:16, SEQ ID NO:17, and a combination thereof; a second nucleotide portion comprising an mRNA encoding a protein of interest, wherein the second nucleotide portion is coupled to the first nucleotide portion; a first protein portion comprising a protein including 4λ domains, wherein each individual λ domain is orientated to specifically bind to a separate and individual boxB domain; and a second protein portion comprising the protein of interest, wherein the second protein portion is coupled to the first protein portion. The protein of the first protein portion, of the foregoing embodiment, can include an amino acid sequence selected from the group consisting of SEQ ID NO:2, SEQ ID NO:4, SEQ ID NO:6, SEQ ID NO:8, SEQ ID NO:10, SEQ ID NO:12, and a combination thereof.

In some embodiments, the protein-RNA display construct includes a first nucleotide portion comprising an RNA including 3 boxB domains, the RNA forming hairpin structures that correspond in number to the boxB domains, wherein each hairpin structure includes a stem and a loop, wherein each individual boxB domain is located in a separate and individual loop, and wherein the RNA includes a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof; a second nucleotide portion comprising an mRNA encoding a protein of interest, wherein the second nucleotide portion is coupled to the first nucleotide portion; a first protein portion comprising a protein including a scaffold protein and 3λ domains extending from the scaffold protein, wherein each individual λ domain is orientated to specifically bind to a separate and individual boxB domain; and a second protein portion comprising the protein of interest, wherein the second protein portion is coupled to the first protein portion. The protein of the first protein portion, of the foregoing embodiment, can include an amino acid sequence of SEQ ID NO:13, SEQ ID NO:22, or a combination thereof.

3. Nucleic Acids

Provided herein are nucleic acids that can encode the disclosed protein-RNA display constructs, where the protein-RNA display construct has a protein of interest and its cognate mRNA sequence coupled to each other. The nucleic acid can have at least three portions. The three portions can include a first portion encoding an RNA sequence that can form hairpin structures, a second portion encoding a protein having domains that can bind to the RNA hairpin structures, and a third portion that encodes a protein of interest.

The different portions can be arranged in a number of different ways. For example, the different portions can be in an upstream to downstream direction as follows: the first portion, the second portion, and the third portion. In some embodiments, the second portion and the third portion are switched where the third portion is between the first portion and the second portion, thereby being upstream from the second portion. In embodiments including a reporter construct, said construct can be positioned upstream or downstream from the second portion.

A. First Portion

The first portion can include a nucleotide sequence encoding an RNA that includes a plurality of RNA hairpin domains. The RNA can form hairpin structures that correspond in number to the number of RNA hairpin domains. Each RNA hairpin structure can include a loop and a stem. Each individual RNA hairpin domain can be located in a separate and individual loop of the RNA structure. The stem can be modified to improve binding between the RNA hairpin domain and the RNA hairpin binding peptide. An example stem modification includes, but is not limited to, an extension. The stem for each loop can be 4 to 30 base pairs, such as 4 to 20 base pairs, 4 to 15 base pairs, or 5 to 8 base pairs.

A number of RNA hairpin domains can be used in the RNA encoded by the nucleotide sequence of the first portion. Example RNA hairpin domains include, but are not limited to, boxB domains, nucleocapsid with hairpin stem-loop from RSV $M_{\varphi}$ packaging signal, and a MS2 coat protein's corresponding AUUA RNA hairpin. In some embodiments, the RNA hairpin domain includes a boxB domain. In some embodiments, the RNA hairpin domain is a boxB domain.

The nucleotide sequence of the first portion can encode an RNA including a varying number of RNA hairpin domains. For example, the nucleotide sequence can encode an RNA including 2 to 20 RNA hairpin domains, such as 2 to 18 RNA hairpin domains, 2 to 16 RNA hairpin domains, 2 to 14 RNA hairpin domains, 2 to 12 RNA hairpin domains, 2 to 10 RNA hairpin domains, 2 to 8 RNA hairpin domains, 2 to 6 RNA hairpin domains, or 2 to 4 RNA hairpin domains. In some embodiments, the nucleotide sequence encodes an RNA including at least 2 RNA hairpin domains, at least 4 RNA hairpin domains, at least 6 RNA hairpin domains, at least 8 RNA hairpin domains, at least 10 RNA hairpin domains, or at least 12 RNA hairpin domains. In some embodiments, the nucleotide sequence encodes an RNA including less than 20 RNA hairpin domains, less than 18 RNA hairpin domains, less than 16 RNA hairpin domains, less than 14 RNA hairpin domains, less than 12 RNA hairpin domains, or less than 10 RNA hairpin domains.

The first portion can include a nucleotide sequence encoding a plurality of boxB domains in RNA hairpin structures. For example, the first portion can include a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop.

The first portion can include a nucleotide sequence encoding an RNA including a varying number of boxB domains. For example, the nucleotide sequence can encode an RNA including 2 to 20 boxB domains, such as 2 to 18 boxB domains, 2 to 16 boxB domains, 2 to 14 boxB domains, 2 to 12 boxB domains, 2 to 10 boxB domains, 2 to 8 boxB domains, 2 to 6 boxB domains, or 2 to 4 boxB domains. In some embodiments, the nucleotide sequence encodes an RNA including at least 2 boxB domains, at least 4 boxB domains, at least 6 boxB domains, at least 8 boxB domains, at least 10 boxB domains, or at least 12 boxB domains. In some embodiments, the nucleotide sequence encodes an RNA including less than 20 boxB domains, less than 18 boxB domains, less than 16 boxB domains, less than 14 boxB domains, less than 12 boxB domains, or less than 10 boxB domains.

As discussed elsewhere, the RNA hairpin domains specifically bind to the RNA hairpin binding peptides. It has been found for improved specific binding, the nucleotide sequence encoding the RNA including the RNA hairpin domains should be in a certain proximity to the nucleotide sequence encoding the protein including the RNA hairpin binding peptides. For example, the nucleotide sequence of the first portion can be positioned 1 nucleotide to 100 nucleotides upstream from the nucleotide sequence of the second portion, such as 1 nucleotide to 80 nucleotides, 5 nucleotides to 90 nucleotides, 10 nucleotides to 50 nucleotides, 2 nucleotides to 50 nucleotides, 40 nucleotides to 100 nucleotides, or 20 nucleotides to 50 nucleotides upstream from the nucleotide sequence of the second portion.

In embodiments that include a nucleotide sequence encoding a ribosome binding site (RBS), the nucleotide sequence of the first portion can be positioned 1 nucleotide to 60 nucleotides upstream from the nucleotide sequence encoding the RBS, such as 1 nucleotide to 50 nucleotides, 5 nucleotides to 45 nucleotides, 10 nucleotides to 50 nucleotides, or 20 nucleotides to 60 nucleotides upstream from the nucleotide sequence encoding the RBS.

The nucleotide sequence of the first portion can include a nucleotide sequence having at least 80%, 85%, 90%, 95%, 99%, or about 100% identity to SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37. The nucleotide sequence of the first portion can also include a combination of the foregoing nucleotide sequences.

In some embodiments, the nucleotide sequence of the first portion includes a nucleotide sequence selected from the group consisting of SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof.

In some embodiments, the first portion is the nucleotide sequence encoding the RNA having a plurality of RNA hairpin domains (e.g., at least 2 boxB domains).

B. Second Portion

The second portion can include a nucleotide sequence encoding a protein that includes a plurality of RNA hairpin binding peptides. Each individual RNA hairpin binding peptide can be orientated to specifically bind to a separate RNA hairpin domain. A number of RNA hairpin binding peptides can be included in the protein encoded by the nucleotide sequence of the second portion. Example peptides include, but are not limited to, λ domains, variations of λ domains (e.g., $\lambda_{N22}$), N-terminal zinc knuckle of RSV (Rous sarcoma virus), and MS2 coat proteins. In some embodiments, the RNA hairpin binding peptide includes a λ domain. In some embodiments, the RNA hairpin binding peptide is a λ domain.

The second portion can include a nucleotide sequence encoding a protein including a varying number of RNA hairpin binding peptides. For example, the nucleotide sequence can encode a protein including 2 to 20 RNA hairpin binding peptides, such as 2 to 18 RNA hairpin binding peptides, 2 to 16 RNA hairpin binding peptides, 2 to 14 RNA hairpin binding peptides, 2 to 12 RNA hairpin binding peptides, 2 to 10 RNA hairpin binding peptides, 2 to 8 RNA hairpin binding peptides, 2 to 6 RNA hairpin binding peptides, or 2 to 4 RNA hairpin binding peptides. In some embodiments, the nucleotide sequence encodes a protein including at least 2 RNA hairpin binding peptides, at least 4 RNA hairpin binding peptides, at least 6 RNA hairpin binding peptides, at least 8 RNA hairpin binding peptides, at least 10 RNA hairpin binding peptides, or at least 12 RNA hairpin binding peptides. In some embodiments, the nucleotide sequence encodes a protein including less than 20 RNA hairpin binding peptides, less than 18 RNA hairpin binding peptides, less than 16 RNA hairpin binding peptides, less than 14 RNA hairpin binding peptides, less than 12 RNA hairpin binding peptides, or less than 10 RNA hairpin binding peptides.

The second portion can include a nucleotide sequence encoding a protein including a plurality of λ domains. For example, the first protein portion can include a protein including at least 2λ domains, wherein each individual λ domain is orientated to specifically bind to a separate and individual boxB domain. The second portion can also include a nucleotide sequence encoding a scaffold protein. Further description of the scaffold protein can be found above.

The second portion can include a nucleotide sequence encoding a protein including a varying number of λ domains. For example, the nucleotide sequence can encode a protein including 2 to 20λ domains, such as 2 to 18λ domains, 2 to 16λ domains, 2 to 14λ domains, 2 to 12λ domains, 2 to 10λ domains, 2 to 8λ domains, 2 to 6λ domains, or 2 to 4λ domains. In some embodiments, the nucleotide sequence encodes a protein including at least 2λ domains, at least 4λ domains, at least 6λ domains, at least 8λ domains, at least 10λ domains, or at least 12λ domains. In some embodiments, the nucleotide sequence encodes a protein including less than 20λ domains, less than 18λ domains, less than 16λ domains, less than 14λ domains, less than 12λ domains, or less than 10λ domains. In some embodiments, the nucleotide sequence of the second portion encodes a protein including a number of λ domains that correspond in number to the number of boxB domains of the RNA encoded by the nucleotide sequence of the first portion. For example, in some embodiments, the protein can include 2 to 4λ domains and the RNA can include 2 to 4 boxB domains.

The nucleotide sequence of the second portion can also encode a protein including linkers. For example, the protein can include linkers between λ domains. For example, in embodiments where the protein includes 3λ domains, the protein can include two linkers (e.g., λ domain-linker-λ domain-linker-λ domain). The linker can be any suitable linker used in the art for protein chemistry. Example linkers are discussed in more detail above with respect to the first protein portion. Furthermore, the nucleic acid can include a nucleotide sequence encoding a linker (as described herein) between the second portion and the third portion.

The nucleotide sequence of the second portion can have a varying number of nucleotides. For example, the nucleotide sequence of the second portion can include 30 nucleotides to 3,000 nucleotides, such as 35 nucleotides to 2,500 nucleotides, 100 nucleotides to 3,000 nucleotides, 500 nucleotides to 3,000 nucleotides, 30 nucleotides to 1,500 nucleotides, or 50 nucleotides to 2,000 nucleotides. In some embodiments, the nucleotide sequence of the second portion includes greater than 30 nucleotides, greater than 35 nucleotides, greater than 50 nucleotides, or greater than 1,000 nucleotides. In some embodiments, the nucleotide sequence of the second portion includes less than 3,000 nucleotide, less than 2,500 nucleotides, less than 2,000 nucleotides, or less than 1,500 nucleotides.

The nucleotide sequence of the second portion can include a nucleotide sequence having at least 80%, 85%, 90%, 95%, 99%, or about 100% identity to SEQ ID NO:1, SEQ ID NO:3, SEQ ID NO:5, SEQ ID NO:7, SEQ ID NO:9, SEQ ID NO:11, SEQ ID NO:24, SEQ ID NO:25, SEQ ID NO:26, SEQ ID NO:27, or SEQ ID NO:28. The nucleotide sequence of the second portion can also include a combination of the foregoing nucleotide sequences.

In some embodiments, the nucleotide sequence of the second portion includes a nucleotide sequence selected from the group consisting of SEQ ID NO:1, SEQ ID NO:3, SEQ ID NO:5, SEQ ID NO:7, SEQ ID NO:9, SEQ ID NO:11, SEQ ID NO:24, SEQ ID NO:25, SEQ ID NO:26, SEQ ID NO:27, SEQ ID NO:28, and a combination thereof.

In some embodiments, the second portion is the nucleotide sequence encoding the protein having a plurality of RNA hairpin binding domains (e.g., at least 2λ domains).

C. Third Portion

The third portion can include a nucleotide sequence encoding a protein of interest. The protein of interest is not limited and can be any protein that can be expressed, e.g., using recombinant technology. The nucleotide sequence of the third portion can have a varying number of nucleotides. For example, the nucleotide sequence of the third portion can include 1 nucleotide to 10,000 nucleotides, such as 10 nucleotides to 10,000 nucleotides, 100 nucleotides to 5,000 nucleotides, 1 nucleotide to 8,000 nucleotides, 1,000 nucleotides to 10,000 nucleotides, or 2,000 nucleotides to 6,000 nucleotides. In some embodiments, the nucleotide sequence of the third portion includes greater than 1 nucleotide, greater than 100 nucleotides, greater than 1,000 nucleotides, or greater than 5,000 nucleotides. In some embodiments, the nucleotide sequence of the third portion includes less than 10,000 nucleotides, less than 7,000 nucleotides, less than 5,000 nucleotides, or less than 3,000 nucleotides.

The third portion can be operably coupled to the first portion and the second portion.

D. Other Sequences

The nucleic acid can include other sequences in addition to those of the first portion, the second portion, and the third portion. For example, the nucleic acid can include a nucleotide sequence encoding a ribosome binding site. The ribosome binding site can be between the first portion and the second portion. The nucleic acid can also include a nucleotide sequence encoding a reporter construct. Further description of reporter constructs can be found above for the protein-RNA display construct. In some embodiments, the reporter construct includes a fluorescent protein. In some embodiments, the reporter construct is a fluorescent protein.

E. Example Nucleic Acids

In some embodiments, the nucleic acid includes, in an upstream to downstream direction: a first portion comprising a nucleotide sequence encoding an RNA including 4 boxB domains, the RNA forming hairpin structures that correspond in number to the boxB domains, wherein each hairpin structure includes a stem and a loop, wherein each individual boxB domain is located in a separate and individual loop, and wherein the nucleotide sequence of the first portion includes a nucleotide sequence selected from the group consisting of SEQ ID NO:14, SEQ ID NO:15, SEQ ID NO:16, SEQ ID NO:17, and a combination thereof; a second portion comprising a nucleotide sequence encoding a protein including 4λ domains, wherein each individual λ domain is orientated to specifically bind to a separate and individual boxB domain; and a third portion comprising a nucleotide sequence encoding a protein of interest, wherein the third portion is operably coupled to the first portion and the second portion. The nucleotide sequence of the second portion, of the foregoing embodiment, may include a nucleotide sequence selected from the group consisting of SEQ ID NO:1, SEQ ID NO:3, SEQ ID NO:5, SEQ ID NO:7, SEQ ID NO:9, SEQ ID NO:11, and a combination thereof.

In some embodiments, the nucleic acid includes, in an upstream to downstream direction: a first portion comprising a nucleotide sequence encoding an RNA including 3 boxB domains, the RNA forming hairpin structures that correspond in number to the boxB domains, wherein each hairpin structure includes a stem and a loop, wherein each individual boxB domain is located in a separate and individual loop, and wherein the nucleotide sequence of the first portion includes a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof; a second portion comprising a nucleotide sequence encoding a protein including a scaffold protein and 3λ domains extending from the scaffold protein, wherein each individual λ domain is orientated to specifically bind to a separate and individual boxB domain; and a third portion comprising a nucleotide sequence encoding a protein of interest, wherein the third portion is operably coupled to the first portion and the second portion. The nucleotide sequence of the second portion, of the foregoing embodiment, may include a nucleotide sequence selected from the group consisting of SEQ ID NO:24, SEQ ID NO:25, SEQ ID NO:26, SEQ ID NO:27, SEQ ID NO:28, and a combination thereof.

F. Genetic Constructs

The nucleic acid may be a genetic construct, such as a vector or plasmid. The vector may be an expression vector or system to produce protein by routine techniques and readily available starting materials including Sambrook et al., Molecular Cloning and Laboratory Manual, Second Ed., Cold Spring Harbor (1989), which is incorporated fully by reference herein in its entirety. The construct may be recombinant. The genetic construct may include regulatory elements for gene expression of the coding sequences of the nucleic acid. The regulatory elements may be a promoter, an enhancer, an initiation codon also referred to as a start codon, a stop codon, or a polyadenylation signal.

The genetic construct may include an initiation codon, which may be upstream of the nucleotide sequence of the first portion, and a stop codon, which may be downstream of the protein of interest coding sequence. The initiation and termination codons may be in frame with the nucleotide sequences of the first portion, the second portion, and the third portion. The vector may also include a promoter that is operably linked to the nucleotide sequence of the first portion. The promoter may be a constitutive promoter, an inducible promoter, a repressible promoter, or a regulatable promoter. The promoter may be a ubiquitous promoter. The promoter may be a tissue-specific promoter. The tissue specific promoter may be a neuronal subtype-specific promoter. The tissue specific promoter may be a cardiomyocyte-specific promoter. The nucleic acid may be under the light-inducible or chemically inducible control to enable the dynamic control of expression of the genetically encoded protein-RNA display construct in space and time. The promoter operably linked to the genetically encoded protein-RNA display construct may be any promoter known in the art. Examples of promoters include, but are not limited to, T7, glial fibrillary acidic protein (GFAP), Tet-On, Tet-Off, simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, a Rous sarcoma virus (RSV) promoter, a CMV early enhancer/chicken β actin (sCAG) promoter, a human cytomegalovirus (hCMV) promoter, a mouse phosphoglycerate kinase (mPGK) promoter, and a human synapsin (hSYN) promoter.

The genetic construct may also include a polyadenylation signal, which may be downstream of the nucleotide sequence of the third portion. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal.

Coding sequences in the genetic construct may be optimized for stability and high levels of expression.

The genetic construct may also include an enhancer upstream, within the coding region of, downstream of, or thousands of nucleotides away from the nucleotide sequence of the first portion. The enhancer may be necessary for DNA expression. The enhancer may be any enhancer commonly used in the art. Examples of enhancers include, but are not limited to, human actin, human myosin, human hemoglobin, human muscle creatine, or a viral enhancer such as one from CMV, HA, RSV, and EBV. The genetic construct may also comprise a mammalian origin of replication in order to maintain the vector extrachromosomally and produce multiple copies of the vector in a cell. The genetic construct may also comprise a regulatory sequence, which may be well suited for gene expression in a mammalian or human cell into which the vector is administered.

The genetic construct may be useful for transfecting cells with the nucleic acid, where the transformed host cell may be cultured and maintained under conditions wherein expression of the protein-RNA display construct takes place. The genetic construct may be transformed or transduced into a cell. The genetic construct may be formulated into any suitable type of delivery vehicle including, for example, a viral vector, lentiviral expression, electroporation, and lipid-mediated transfection for delivery into a cell. The genetic construct may be part of the genetic material in attenuated live microorganisms or recombinant microbial vectors which live in cells. The genetic construct may be present in the cell as a functioning extrachromosomal molecule.

In some embodiments, the nucleic acid is a vector. In some embodiments, the nucleic acid is a plasmid.

In some embodiments, the nucleic acid comprises, in an upstream to downstream direction: a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop; a second portion comprising a nucleotide sequence encoding a protein including at least 2λ domains, wherein each individual λ domain is orientated to specifically bind to a separate and individual boxB domain; and a cloning site for insertion of a nucleotide sequence encoding a protein of interest, the cloning site operably coupled to the first portion and the second portion.

4. Libraries

Also provided herein are libraries of the disclosed protein-RNA display constructs. The library can include at least two proteins of interest. The library can include different proteins of interest. In some embodiments, each protein of interest in the library is different. In addition, the library can include control proteins, such as a wild type protein where varying proteins of interest are modified wild type proteins.

In some embodiments, the library includes at least $1\times10^4$ different proteins of interest, at least $1\times10^6$ different proteins of interest, at least $1\times10^8$ different proteins of interest, at least $1\times10^{10}$ different proteins of interest, at least $1\times10^{12}$ different proteins of interest, or at least $1\times10^{14}$ different proteins of interest. In some embodiments, the library includes less than $1\times10^{20}$ different proteins of interest, less than $1\times10^{18}$ different proteins of interest, or less than $1\times10^{16}$ different proteins of interest. In some embodiments, the library includes about 2 different proteins of interest to about $1\times10^{20}$ different proteins of interest, such as about 10 different proteins of interest to about $1\times10^{20}$ different proteins of interest, about 100 different proteins of interest to about $1\times10^{20}$ different proteins of interest, or about $1\times10^{10}$ different proteins of interest to about $1\times10^{16}$ different proteins of interest.

The library can be made by expressing one or more of the disclosed nucleic acids that encode one or more of the protein-RNA display constructs as described in the methods. The description of the protein-RNA display constructs above can be applied to the libraries as disclosed herein.

5. Kits

Also provided herein are kits, which may be used to carry out the disclosed methods. The kits may include one or more of the nucleic acids and/or protein-RNA display constructs as described above. Accordingly, the description of the nucleic acids and protein-RNA display constructs can be applied to the kits as disclosed herein.

The kits also may include instructions for using the components included in the kits. Instructions included in the kits may be affixed to packaging material or may be included as a package insert. While the instructions are typically written on printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

In some embodiments, the kit includes a nucleic acid as disclosed herein; and one or more packages, receptacles, labels, or instructions for use. The nucleic acid may have a nucleotide sequence encoding a protein of interest or may have a cloning site for insertion of a nucleotide sequence encoding a protein of interest.

6. Methods

Further disclosed herein are methods of performing high throughput proteomics through, e.g., panning a library of protein-RNA display constructs. The method can include expressing one or more of the nucleic acids as disclosed herein. By expressing one or more disclosed nucleic acids, a plurality of protein-RNA display constructs can be produced (e.g., a library of protein-RNA display constructs). Expression of the nucleic acid can be done in vitro or in vivo. In some embodiments, the nucleic acid is expressed in vitro. Expression of the nucleic acid in vitro can be done by transfecting a cell in culture with the nucleic acid. Methods of cellular transfection are well known in the art such as the methods describe by Fus-Kujawa et al., *Front. Bioeng. Biotechnol.,* 9; 2021. The cell may be propagated, and the protein-RNA display constructs may be produced by and extracted from the propagated cells. Expression of the nucleic acid in vivo can be done by administering the nucleic acid to a subject, a tissue within a subject, a cell within a subject, or a combination thereof. The nucleic acid may be administered to a subject by methods known in the art, such as direct administration of a naked nucleic acid, electroporation of the nucleic acid into a tissue, and transformation of the nucleic acid into the subject, for example, if the subject is a bacterium.

The description of the nucleic acids and protein-RNA display constructs, and libraries thereof, above can be applied to the disclosed methods. In some embodiments, the library comprises at least $1\times10^{12}$ different proteins of interest.

The method can include contacting the library of protein-RNA display constructs with a target molecule. As used herein, a "target molecule" is a molecule that is being assessed against the library of protein-RNA display constructs, where one is looking at specific interactions between a protein of interest and the target molecule (e.g., specific binding). Example target molecules include, but are not limited to, a protein, an oligonucleotide, a small molecule, a carbohydrate, a lipid, and combinations thereof. In some embodiments, the target molecule is a protein, an oligonucleotide, or a small molecule. In some embodiments, the target molecule is a protein or an oligonucleotide. In some embodiments, the target molecule is a protein.

The method can further include identifying at least one protein of interest (e.g., of a protein-RNA display construct) that specifically binds to the target molecule. In some embodiments, the method includes identifying a plurality of proteins of interest, each protein being different from each other, that specifically bind to the target molecule.

The method can then include optionally sequencing the mRNA encoding the at least one protein of interest that specifically binds to the target. This can be done by methods known within the art, such as, but not limited to, Illumina sequencing and Sanger sequencing.

The method can also include an enriching step. For example, the method can include applying selection pressure by iteratively selecting protein-RNA display constructs that bind specifically to the target molecule. Accordingly, the method can further include removing at least one protein of interest that specifically binds to the target molecule. In some embodiments, the method includes removing a plurality of proteins of interest, each protein being different from each other, that specifically bind to the target molecule. This can provide an enriched library of protein-RNA display constructs.

To further enrich the library, the steps of contacting the enriched library with the target molecule, another target molecule, or a combination thereof, identifying at least one protein of interest that specifically binds to the target molecule(s), and removing the at least one protein of interest can be repeated a number of times (e.g., 2 times to 1,000 times), where the number of times can depend on the library and the target molecule being assessed. Furthermore, prior to repeating the aforementioned steps, the at least one protein of interest that specifically binds to the target molecule can be amplified, e.g., amplifying the nucleic acid expressing the protein of interest.

The disclosed invention has multiple aspects, illustrated by the following non-limiting examples.

7. EXAMPLES

Example 1

GRIP Display: A Novel Peptide Library Display System

GRIP Technology Design

Figure 2:
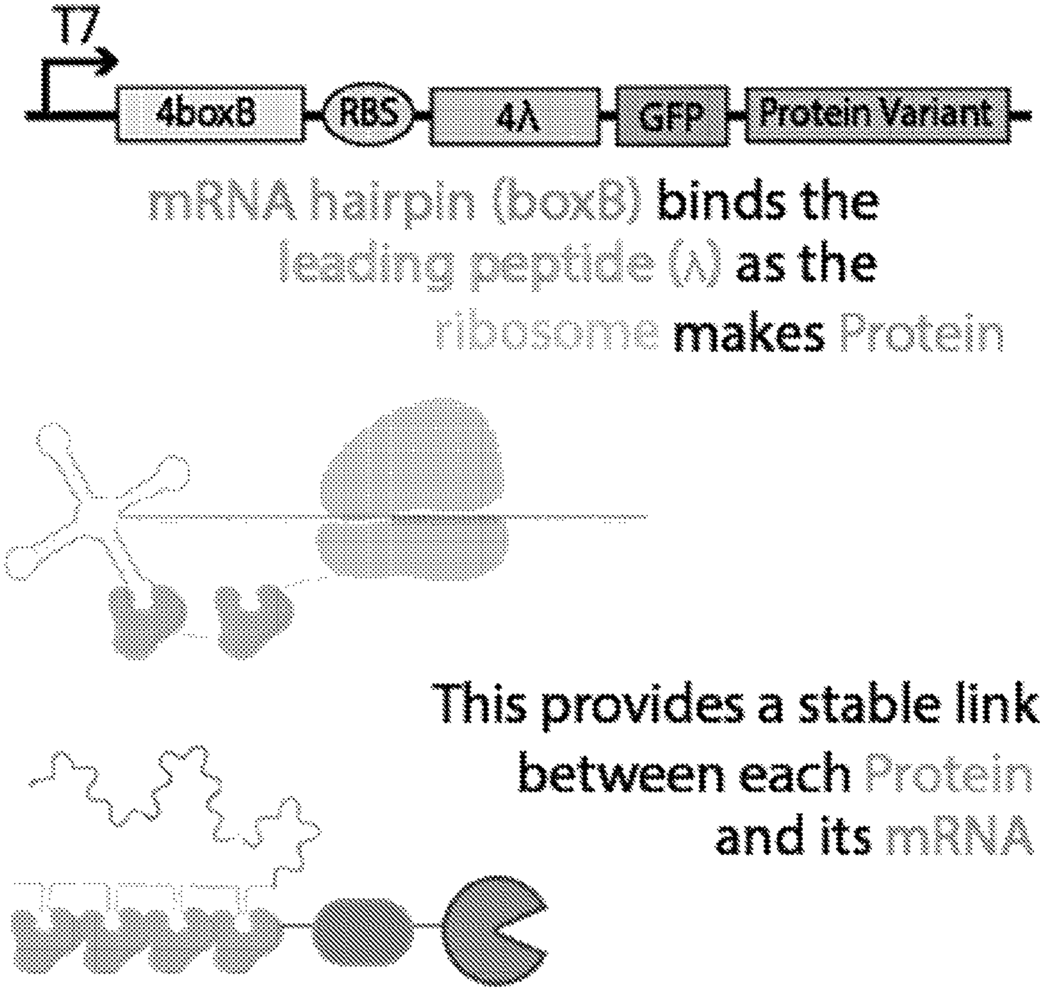
FIG. 2 shows a schematic of an example nucleic acid and an example protein-RNA display construct.

GRIP Display (Gluing RNA to Its Protein) (FIG. 2) represents a novel library-display system capable of generating large ($10^{14}$-member) libraries, while offering the protein-mRNA linkage stability needed for stringent selection. It leverages a high-affinity interaction between a 22 amino-acid λ peptide motif and 15-nt BoxB RNA hairpin sequence borrowed from a virus. There is precedent that the λ/boxB interaction has utility in several applications, including biochemical assays, live-cell imaging, and efforts to map neural connectivity through mRNA barcoding. However, peptide/hairpin interactions have not been used in library display. In comparison to prior deployments of the λ/boxB interaction, library display poses unique challenges in that each mRNA molecule must be glued it its own corresponding protein; this requires linkage fidelity where each individual mRNA is bound to its own protein, with no crosstalk or swapping with other mRNA/protein pairs in solution. Moreover, linkage stability that lasts for long periods of time (e.g., hours) under a wide range of environmental conditions necessary for stringent selection and/or washing is useful.

Considerations for GRIP.1 Design

To address these challenges, two design principles were utilized: (1) With regard to linkage stability, avidity was used to increase the stability of the λ/boxB interaction: N tandem repeats of the boxB hairpin, with a corresponding N tandem λ peptides, is hypothesized, without being bound by a particular theory, to produce a strong λN/boxBN interaction, given the low likelihood that all interactions dissociate at any instant. (2) With regard to linkage fidelity, the $boxB_N$ and $\lambda_N$ motifs were positioned such that nascent $\lambda_N$ peptides (during ribosome-mediated translation) will be held in close proximity to the $boxB_N$ corresponding to its own mRNA. This maximizes the likelihood that each protein binds to the correct mRNA.

Improving Linker Stability

The binding pocket improvement of a functional protein had proven to be a difficult task for the existing technologies. Therefore, efforts were focused on one such system to make sure that GRIP Display is able to improve the activity of large proteins and enzymes. However, the application of the GRIP Display technology is not limited to large proteins only, but instead includes the ability to functionally improve any type of bio-molecule, including antibodies and short or long peptides.

Figure 3A:
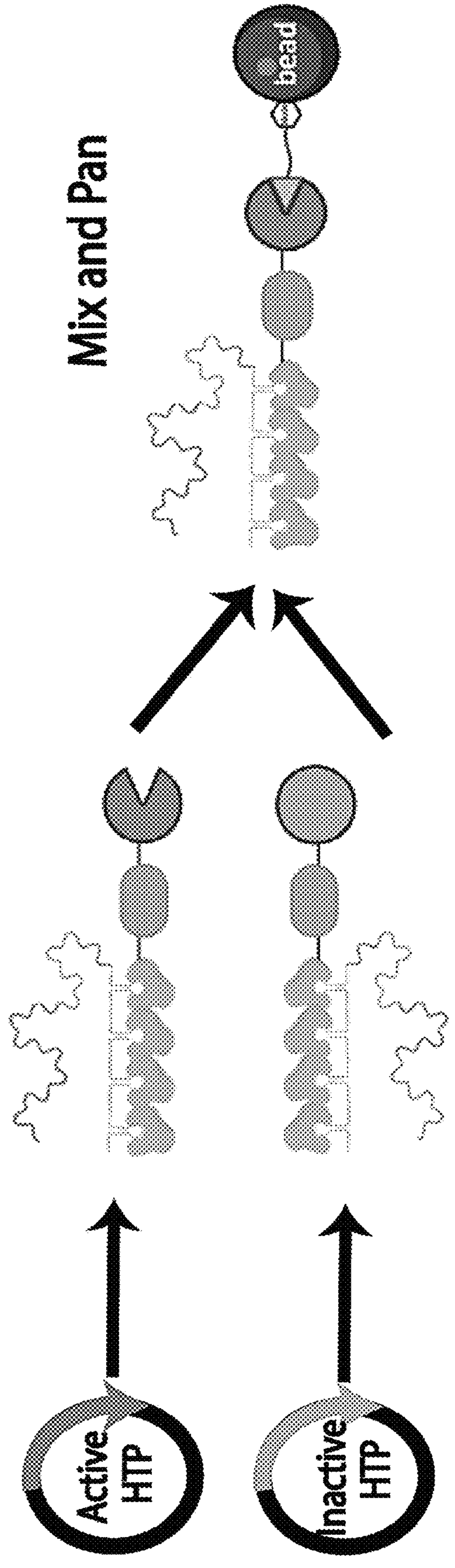
FIG. 3A-FIG. 3D show characterization of linker stability.
Figure 3B:
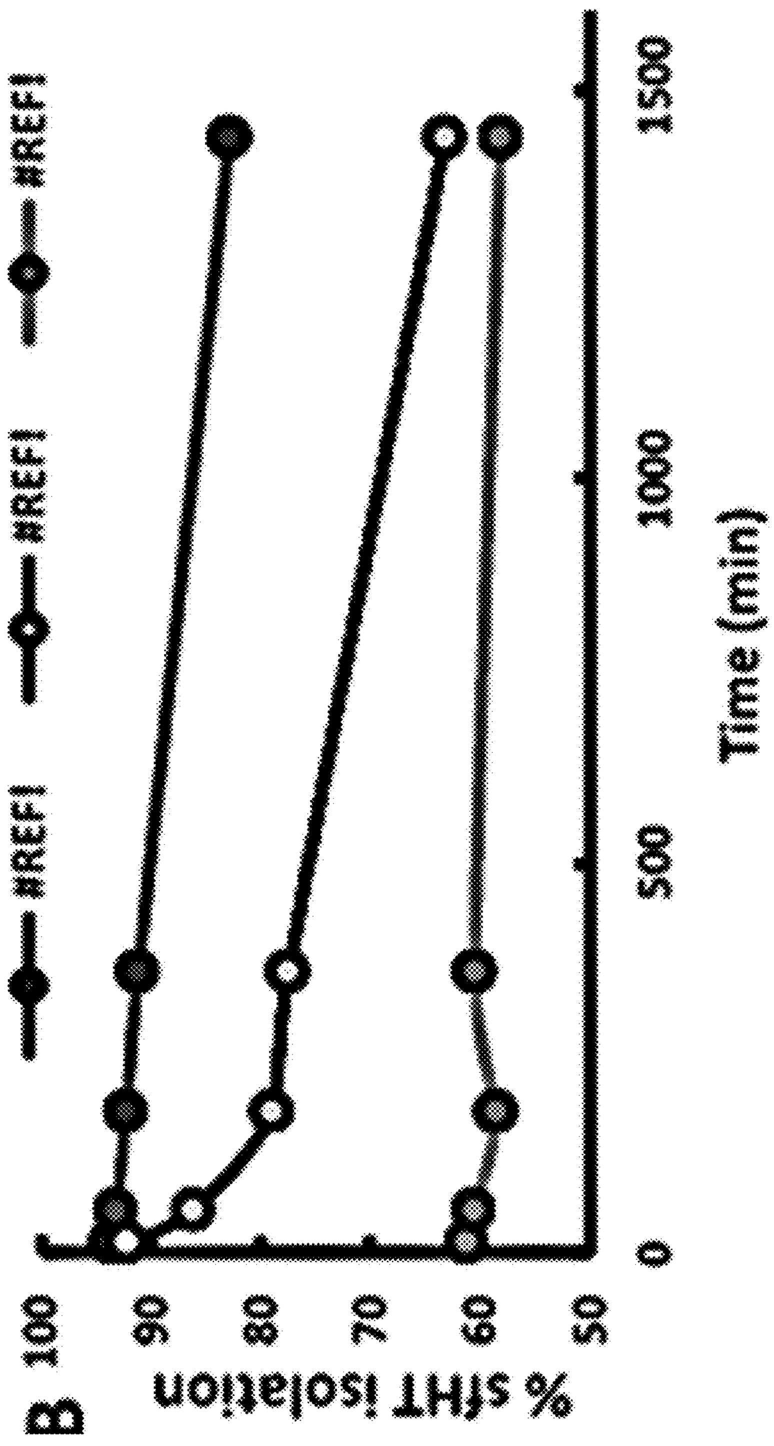
Figure 3C:
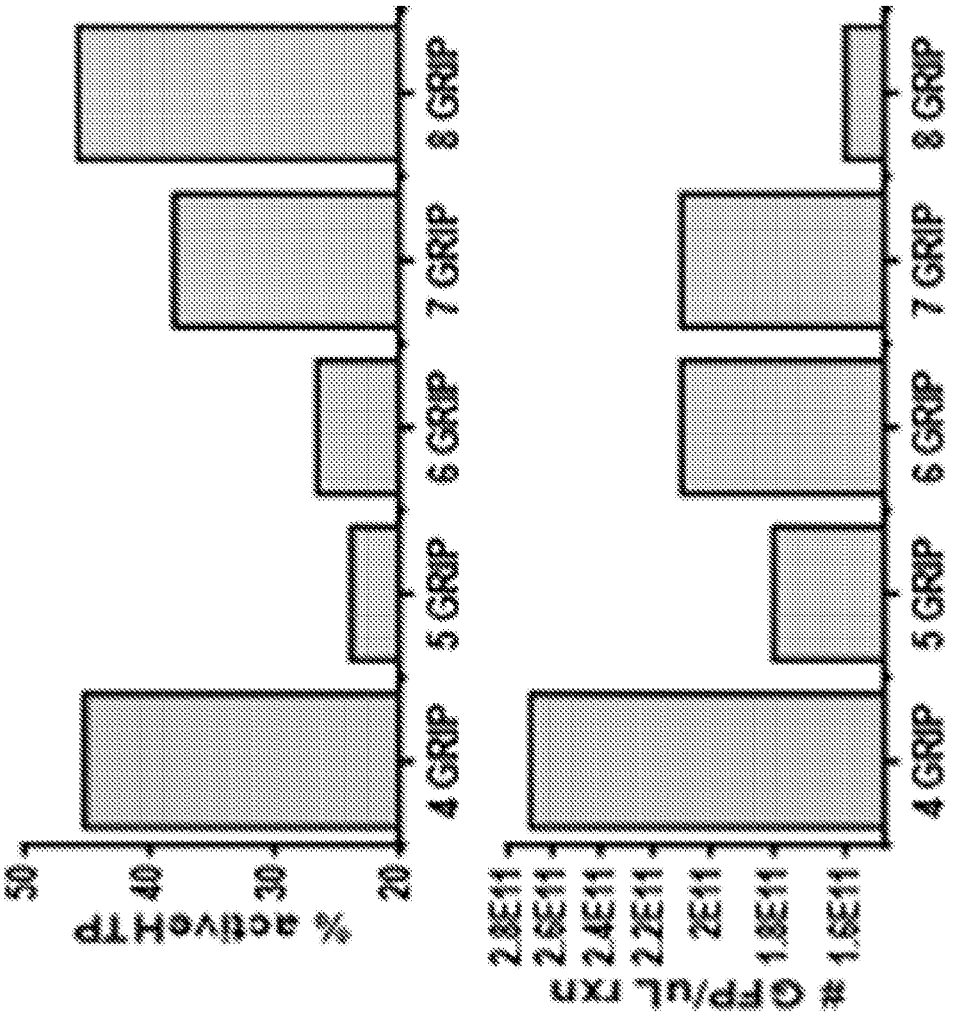

In order to design and evaluate GRIP Display, advantage was taken of a covalent capture reaction between HaloTag protein (HTP) and its ligand (HTL). The ligand was labeled with biotin and used streptavidin magnetic beads to pull down captured proteins. To start, 1 through 4 tandem λ/boxB were taken and in vitro expression to GRIP was used to display two variants of HaloTag protein: active that can efficiently and irreversibly bind its ligand, and its inactive version, where the binding pocket was altered to halt the reaction (FIG. 3A). Both plasmids contain GFP for protein expression evaluation and normalization. The two protein versions were expressed separately and then mixed at equal proportions for various time points prior to pull down with the beads. This experimental design allowed for the distinguishing between non-specific binding to the surface of the beads (estimated 0-3% from extrapolation to 0 min mix time) and the genetic cross-talk, where the rate of mRNA exchange can be evaluated as a function of time by comparing active/inactive mRNA isolation (FIG. 3B). Moreover, the same assay provides an insight into the linkage fidelity as well. Based on this assay, 4 tandem λ/boxB patterns provided the highest genotype/phenotype linkage stability with only 10% of total mRNA swap within 24 hr timeframe. The same data was fitted into an exponential function (FIG. 17) in order to estimate the time constant of the release between each examined λ/boxB patterns. The estimated $k_{off}$ for the 4boxB/λ was over 63 hours compared to the 10 minutes for a single boxB/A bond. Next, the number of tandems was increased. However, it provided little benefit with respect to active HT enrichment, while decreasing the efficiency of PCR steps due to repetitive DNA motifs as well as decreasing in vitro protein production (FIG. 3C).

Figure 3D:
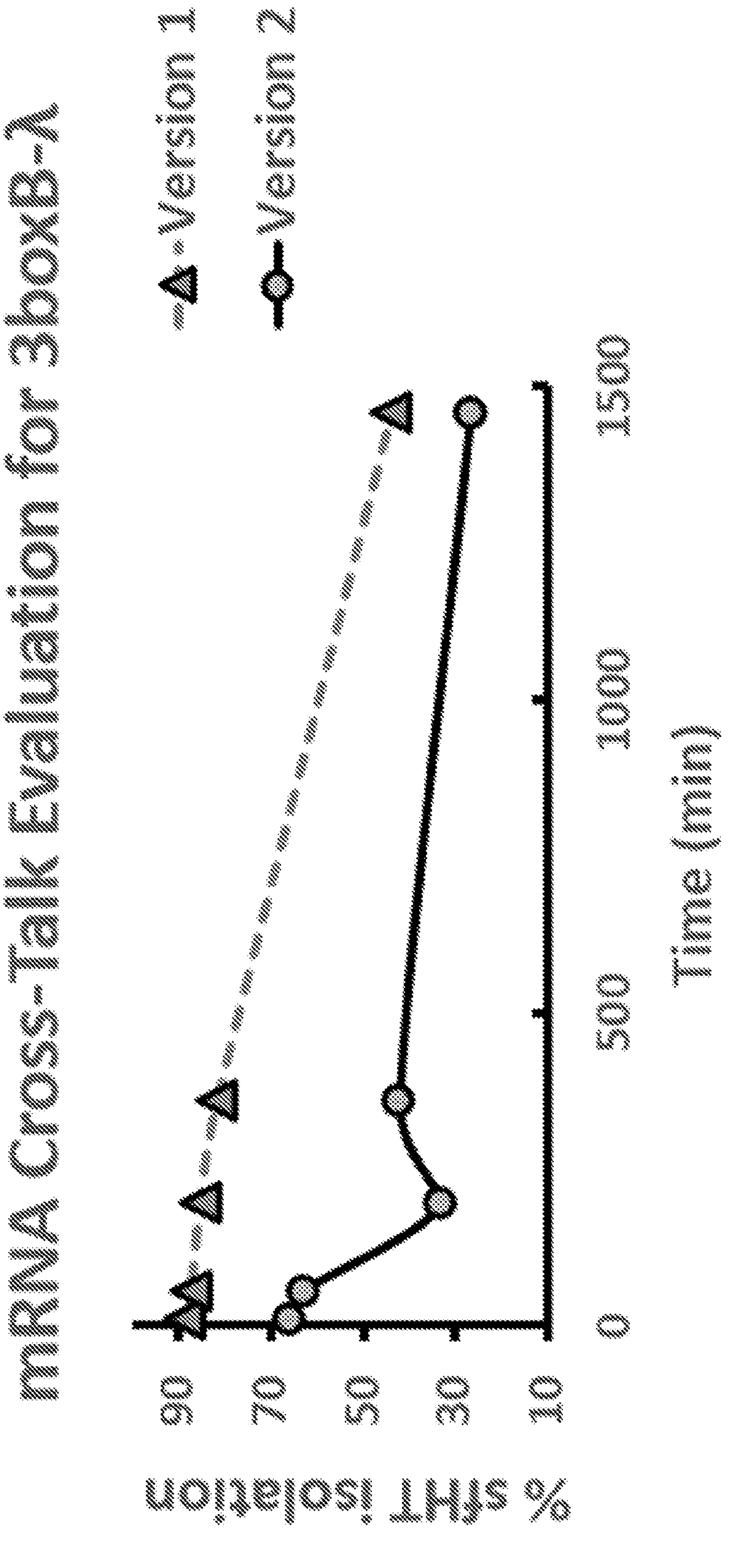

It's worth to note that base-pair improvement of all repetitive regions in DNA sequences (both boxB and λ) was done to increase PCR efficiency and minimize off-target PCR product formation. Moreover, unique stem extensions in boxB regions were introduced to favor local stem-loop formation of the hairpins over the long-range collapsed folding that was observed in boxB designs in prior use. Such modifications are not trivial: not only that all boxB loops should fold in energetically preferred manner, but it should also provide a stable boxB-λ formation. In fact, some stem extension variants worked better than others in the context of a library display. (FIG. 3D) shows the difference in the mRNA-protein linkage stability of 3boxB construct with two different variations of the loop extensions, where the first version holds on to its genetic material better compared to the second version.

Improving Linkage Fidelity

Figure 4A:
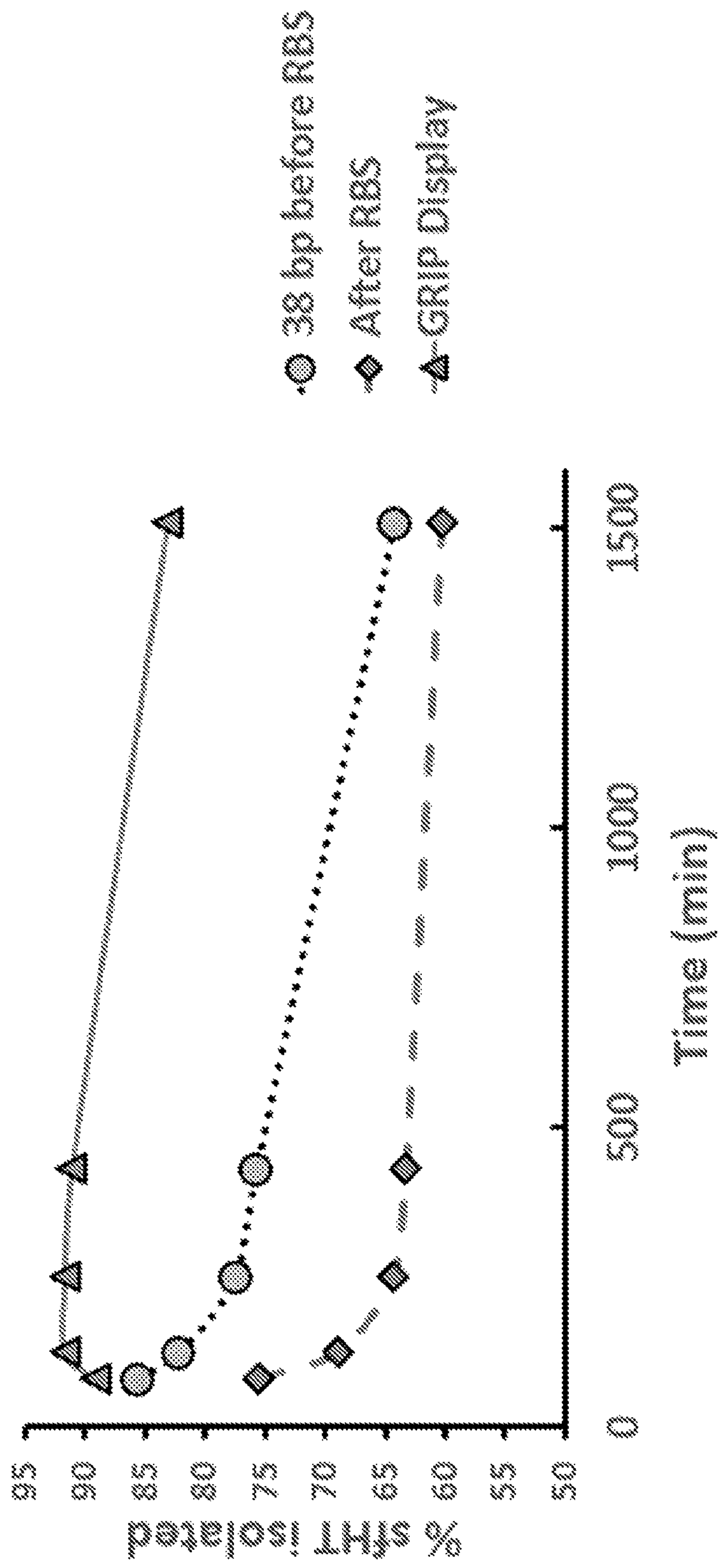
FIG. 4A-FIG. 4D show characterization of linkage fidelity.
Figure 4B:
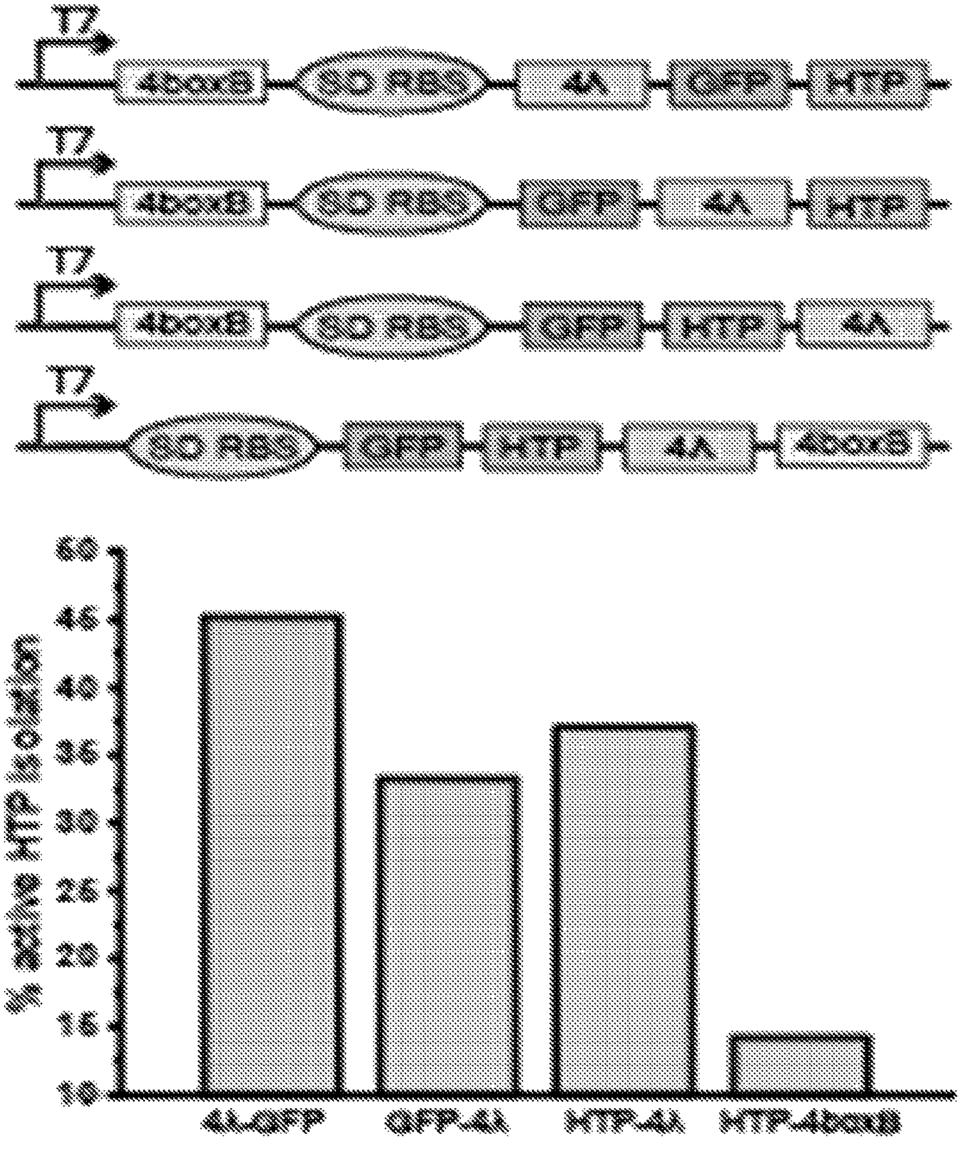

In the context of library display, where billions of protein variants are simultaneously displayed, it is important that GRIP display connects each mRNA to its own protein rather than a random protein in the reaction mix. To maximize the likelihood of correct complex formation, plasmid locations of boxB and λ tandems were explored with respect to each other to identify the best position. Different positions of 4boxB were explored within the DNA construct and quickly established that the fidelity (measured via % live HT isolation as described herein) is dependent on the location of 4boxB relative to λs (FIG. 4A and FIG. 4B).

Figure 4C:
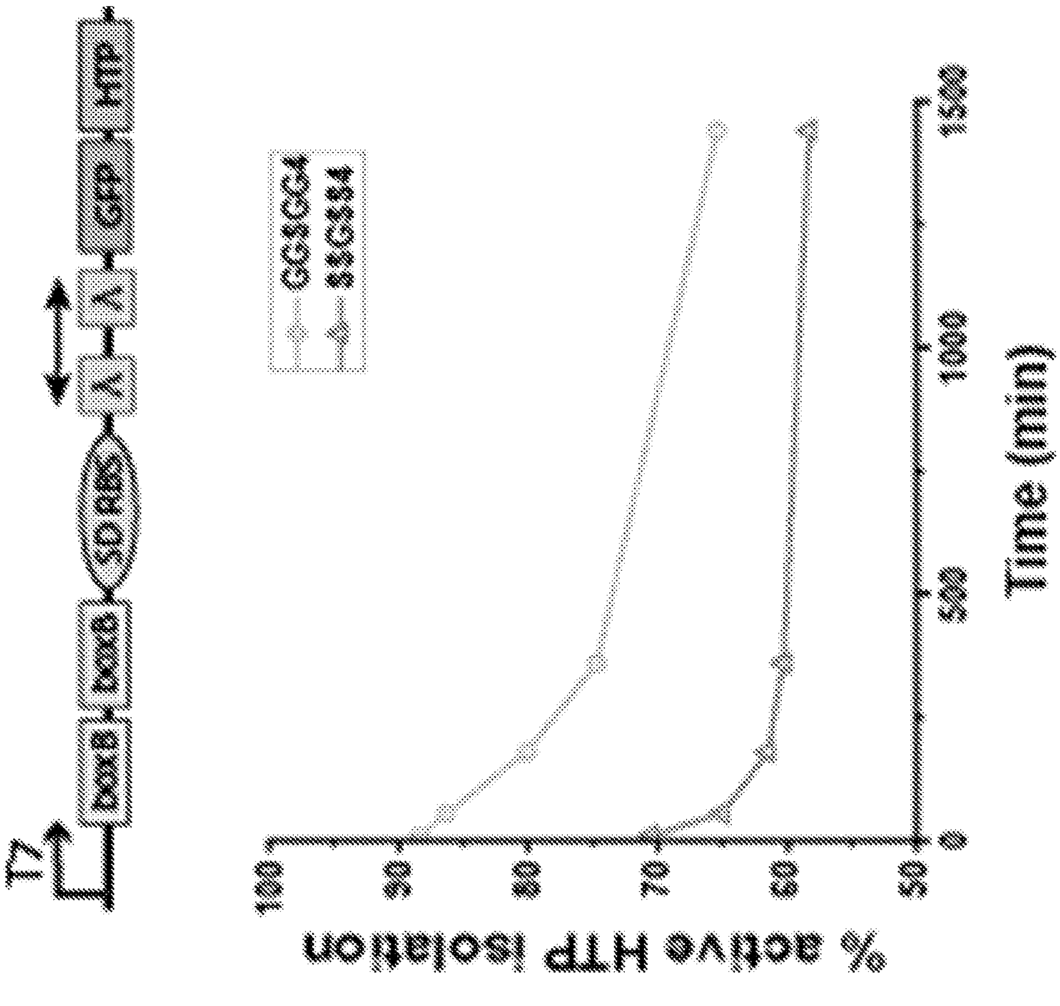
Figure 4D:
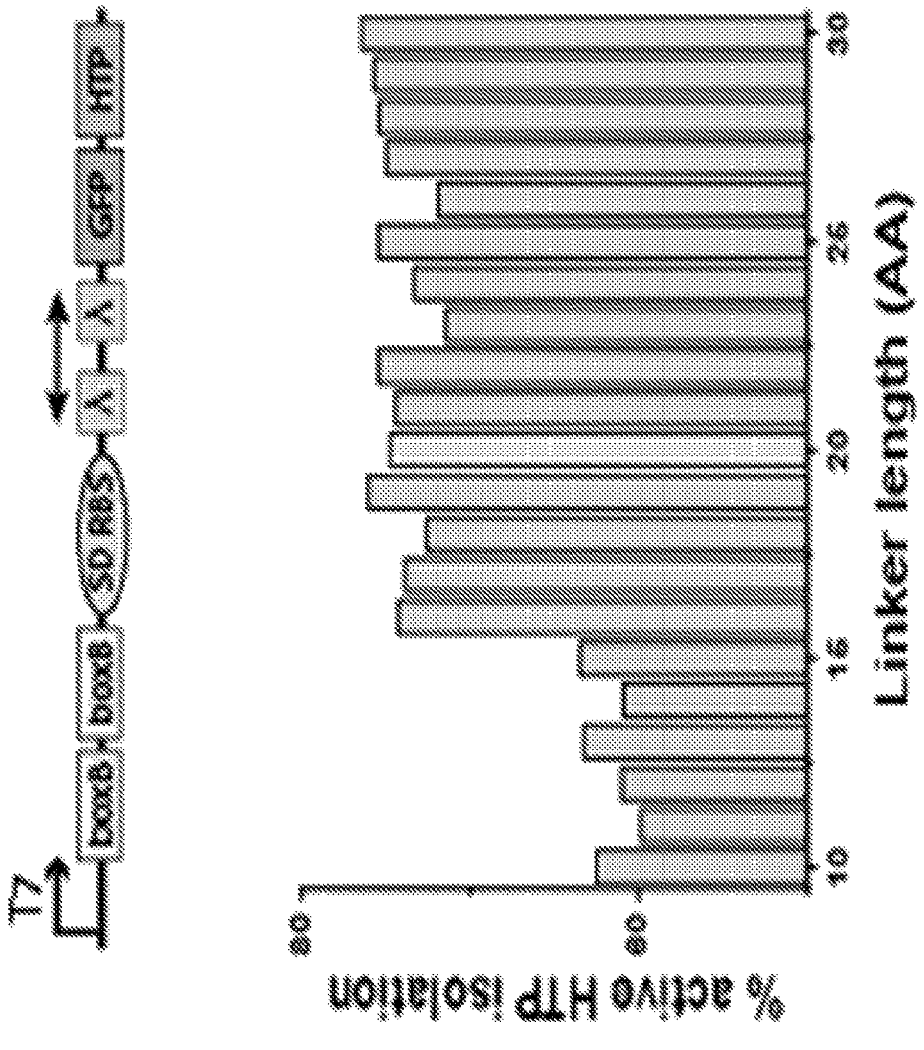

Different linker compositions between λ tandems were also explored as different linker length (FIG. 4C and FIG. 4D). The version of 2boxB-λ construct was used to examine the effect of the linker modification on the fidelity of the system. It was found that longer and more flexible linkers worked better in the context of the protein display application.

GRIP vs Ribosome Display Linkage Stability

Figure 5A:
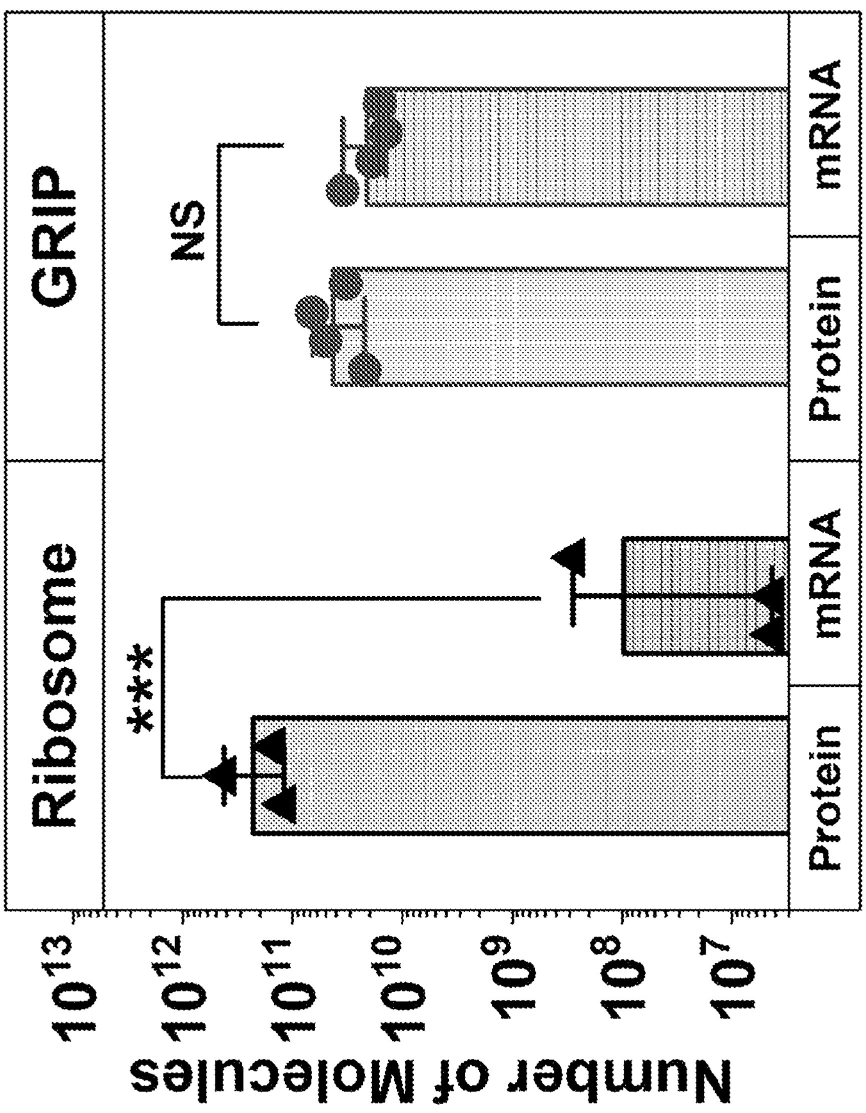
FIG. 5A-FIG. 5B show a comparison of ribosome display v. Gluing RNA to Its Protein (GRIP) display.
Figure 5B:
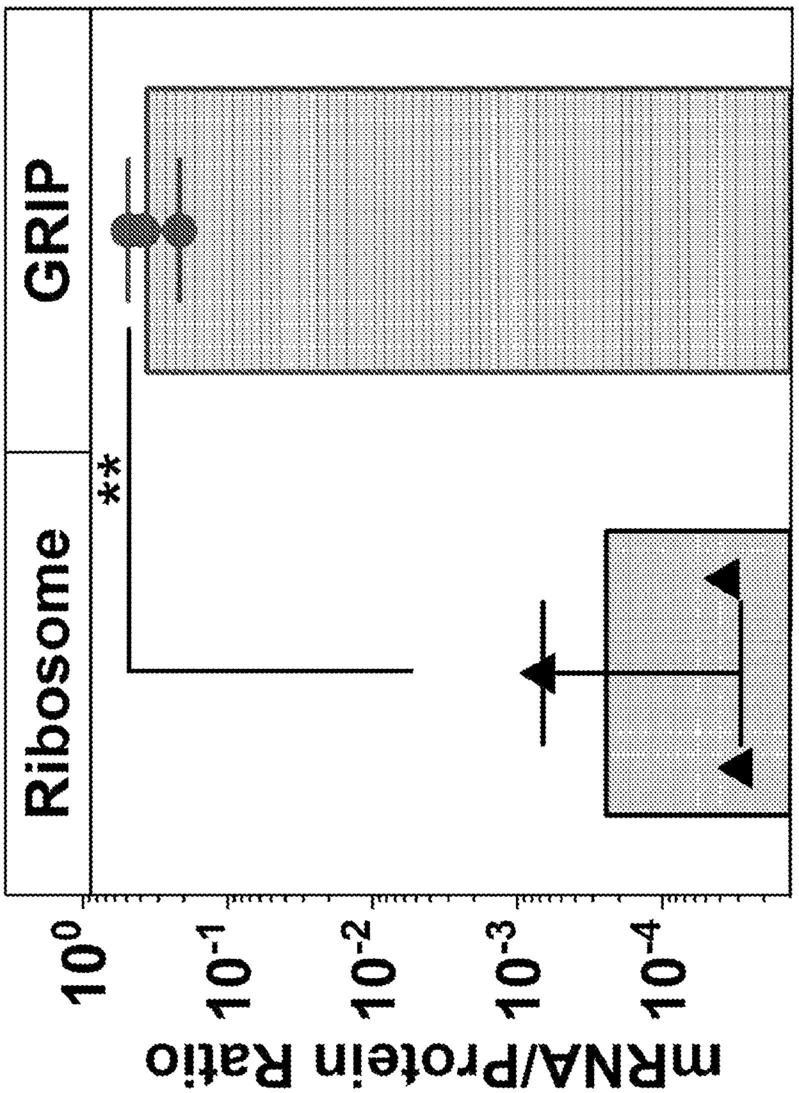

To evaluate the GRIP system as provided herein, active HT protein tagged with GFP was expressed in the 4 GRIP plasmid and quantified protein expression using fluorescent tag. Advantage was then taken of the HT-HTL covalent reaction to isolate the mRNA/protein complexes via HTL-conjugated magnetic beads. The same panning step was performed for HT using Ribosome Display system, where a special stalling mRNA sequence was used to trap the ribosome with mRNA during translation. The amount of the GFP molecules of the beads was then quantified and measured the corresponding number of mRNA molecules via RT-qPCR (FIG. 5A and FIG. 5B). The RT-qPCR data indicates that GRIP Display retains over 10,000 times more genetic material compared to the Ribosome display. Given that linkage stability is proportional to the ratio of RNA to protein, this indicates that GRIP has ~10,000-fold better linkage stability than Ribosome display.

Enrichment of Active Variants in a Small Protein Library

In order to evaluate the performance of GRIP Display in the context of a protein library, a small focused HaloTag protein pool of 20 variants with unknown affinity towards HTL was created. The library was assembled via standard PCR technique by mutating D106 # site using degenerative NNS codon. Since D106 is involved in covalent HT-HTL bond formation, it is expected to have both active (wt) and inactive forms of HT among the variants, 3% of stop codons, and the rest—of unknown partial activity. By performing a single round of panning against HTL, the enrichment of the active WT HaloTag as well as the partially active variants is expected. The library was expressed in vitro using plasmid with GRIP Display components and incubated the resulting protein-mRNA complexes with the HTL-conjugated magnetic beads. The isolated genetic material was cloned into the T7 plasmid for subsequent bacterial transformation. The resulting bacteria was plated on IPTG and HTL-TMR containing agar plates and the evaluated for TMR signal, where the magnitude of the TMR signal per colony is directly proportional to the activity of the HT variant, expressed in that colony.

Figure 6A:
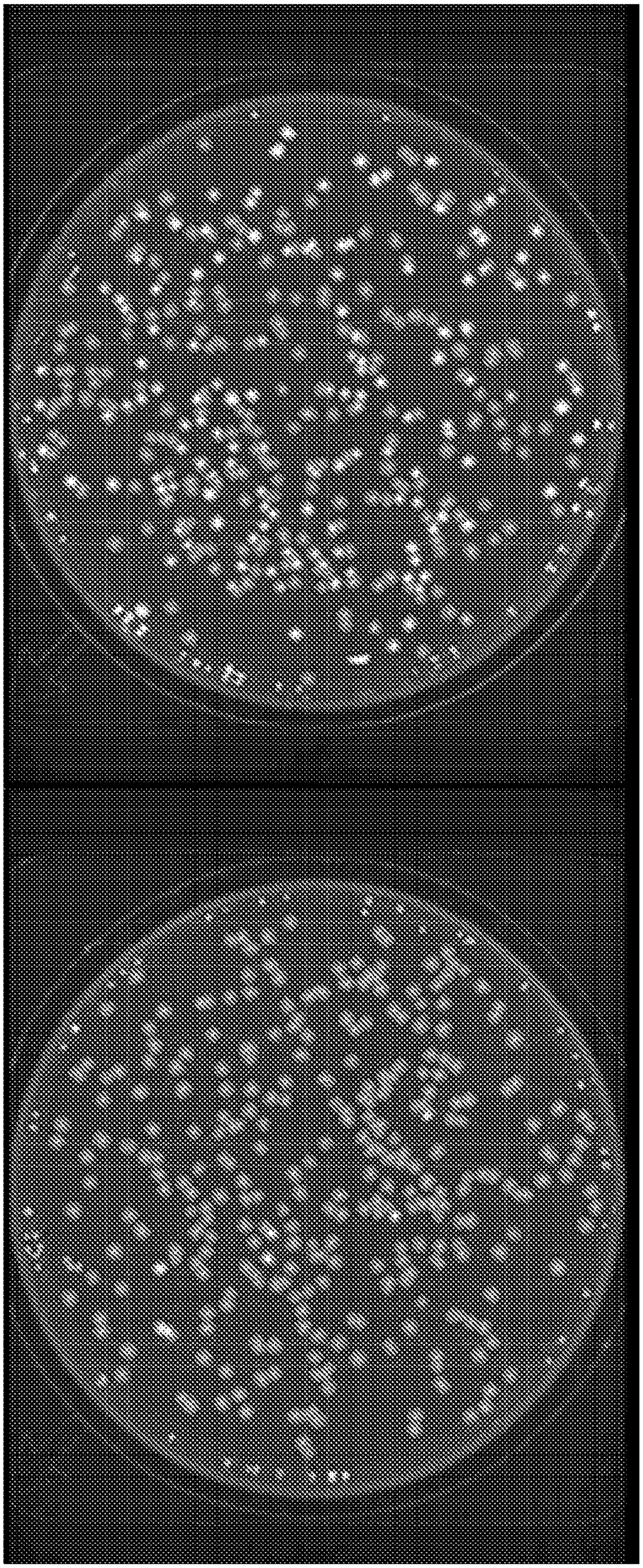
FIG. 6A-FIG. 6D show an example enrichment of active variant proteins.
Figure 6B:
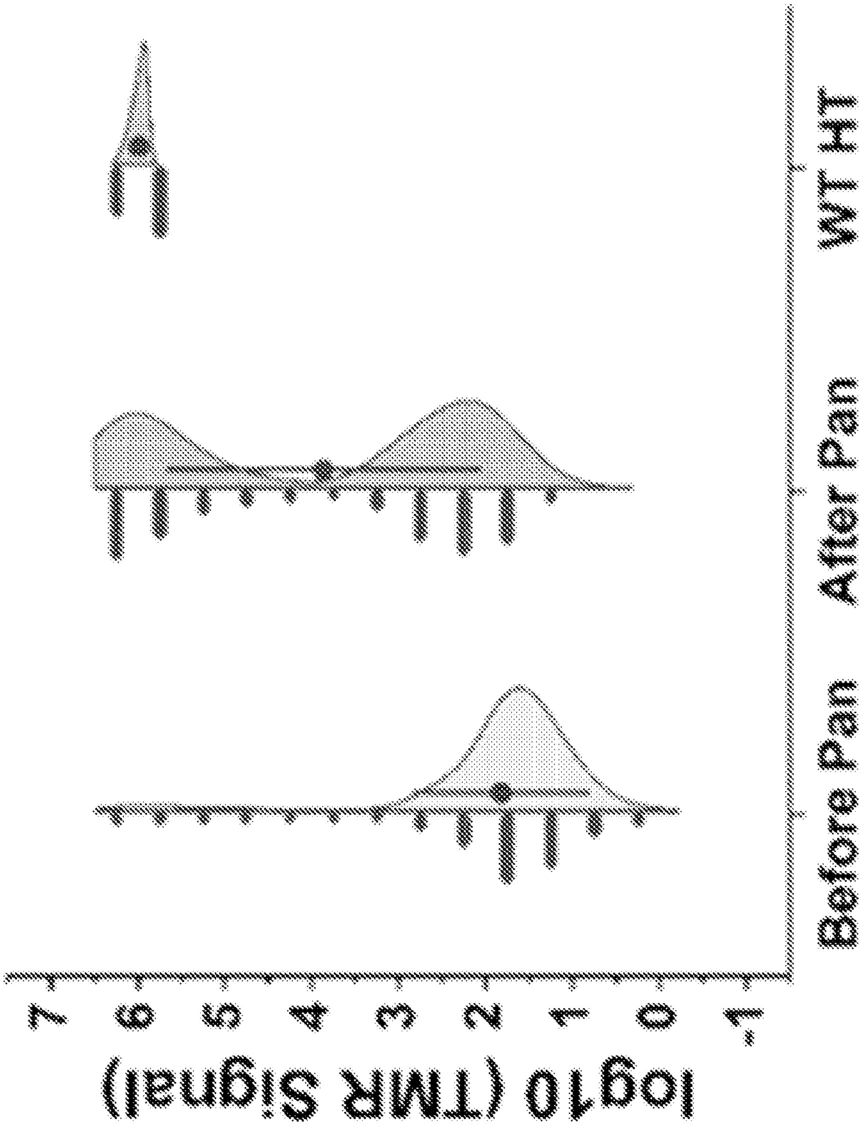
Figure 6C:
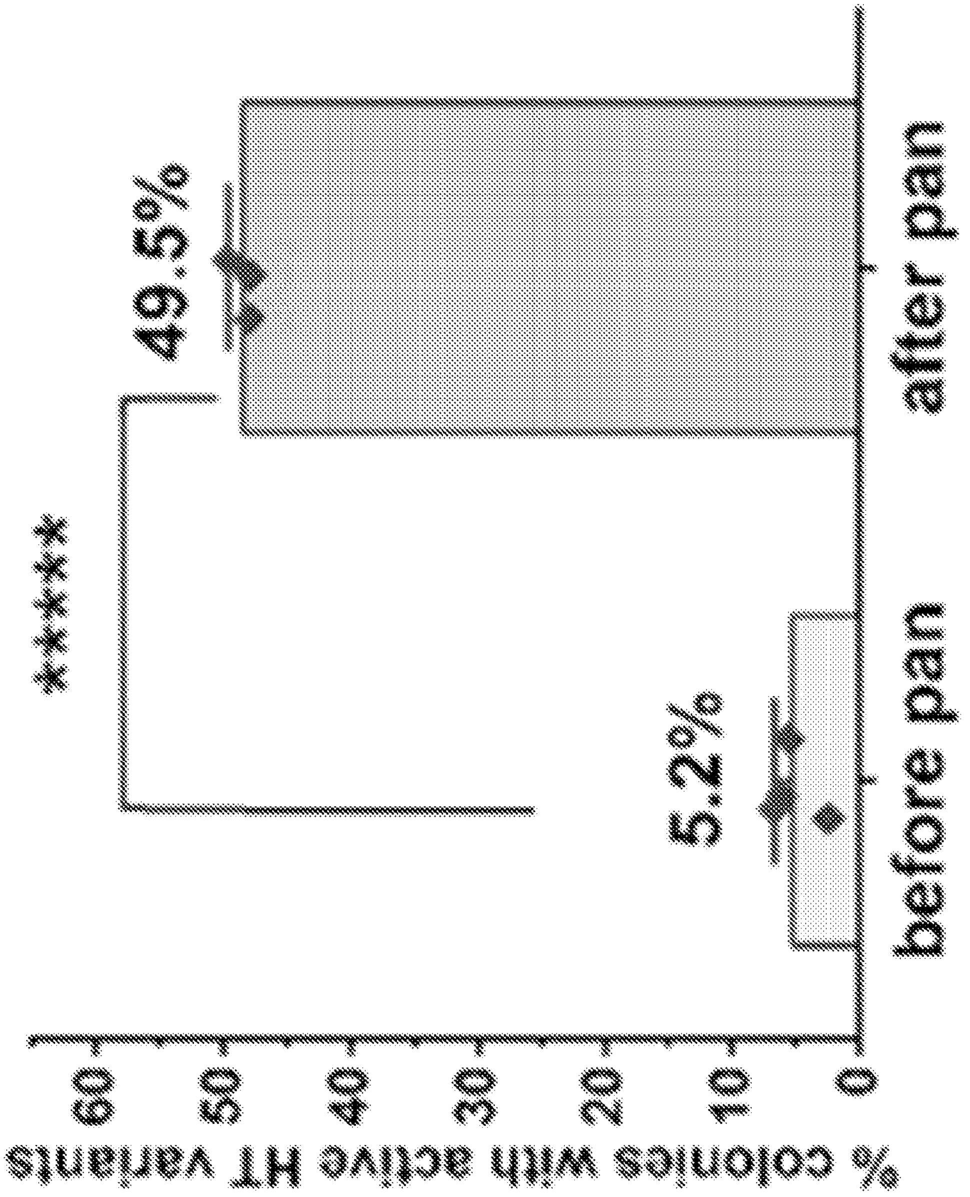
Figure 6D:
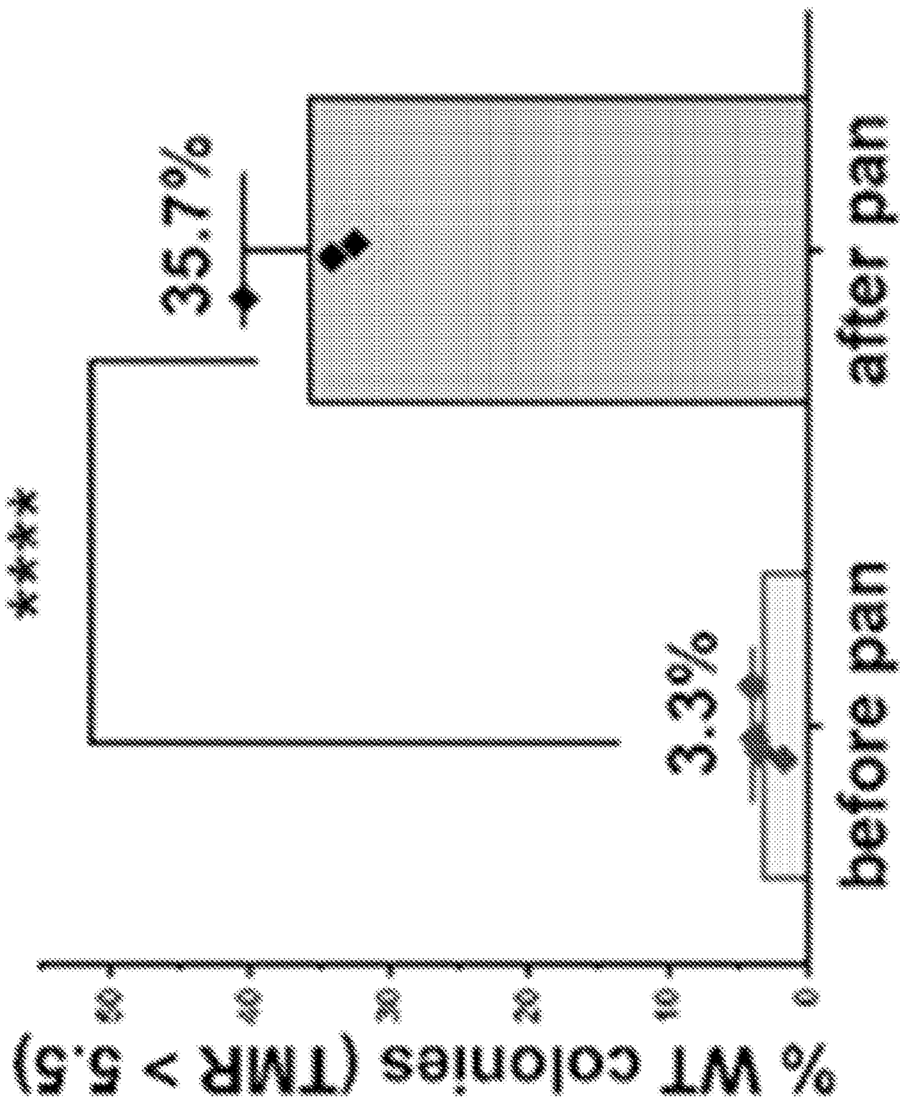

A single round of panning provided a successful enrichment of WT HaloTag protein (FIG. 6A, FIG. 6B, and FIG. 6C). The original library was estimated to have 3.25% of WT HT, based on the redundancy of NNS codon1. The observed percent of colonies with WT-associated TMR signal (FIG. 6D) in the original protein library was 3.3%, which confirmed the proper library assembly. After just one round of panning, a pronounced bi-modal TMR signal distribution was observed, indicating the increase in high TMR-signal colonies (FIG. 6B). The total enrichment of HT protein variants having variable HTL affinity ($Log_{(TMR)>3}$) reached 50% of total, corresponding to 210-fold change from the original library. Most of the enrichment was attributed to the D106D variant (WT), which increased its abundance from 3.3% to 35.7% (FIG. 6D). Moreover, the activity-enriched library also contained a larger representation of partially active variants, increasing from 2% to 13%, which corresponded to 6.5-fold enrichment. Several pronounced TMR signal distributions were noticed within the partially active colonies and it was hypothesized, without being bound by a particular theory, that each peak corresponded to a specific variant. A subset of colonies was sequenced, revealing the highly correlated relationship between the TMR signal and the sequence of the variant. None of the variants in the 20-member protein pool had better HTL affinity than the WT HT. This experiment further substantiated the ability of GRIP Display technology to isolate both highly active proteins as well as ones with moderate to low activity.

Enrichment of Pseudo-Libraries with Known Starting Activity

In the library of $10^{14}$ members, only a small fraction of proteins will have improved ligand capture properties. Each panning round must be stringent enough to isolate and enrich this small fraction. Several experiments were performed to evaluate the enrichment capability of GRIP. 1 Display in the context of large protein libraries with different levels of active members.

To do so, the DNA encoding the wild type HT protein and its inactive version (where the active site was mutated such that activity of the protein was lost) were mixed at different proportions, creating pseudo-libraries with known initial activity levels. The initial activity levels ranged from 0.1% to 100%. It was confirmed the actual activity levels using method described in the previous section via bacterial transformation and plating. For example, the experimentally derived percent of colonies with WT-associated TMR signal (FIG. 7C) for the 1% theoretical activity protein library was 1.2%.

Figure 7A:
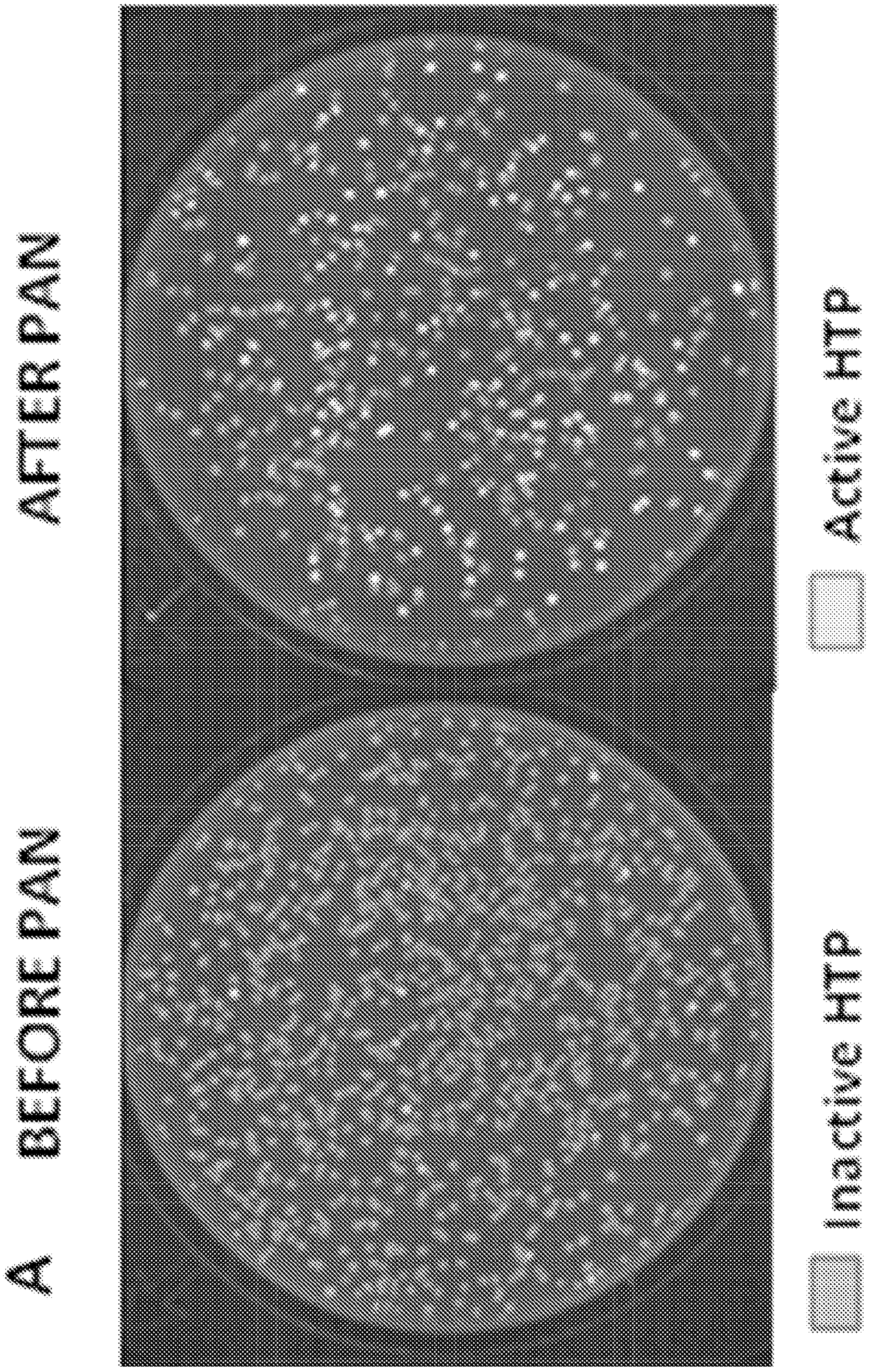
FIG. 7A-FIG. 7E show enrichment of pseudo-libraries with known starting activity.
Figure 7B:
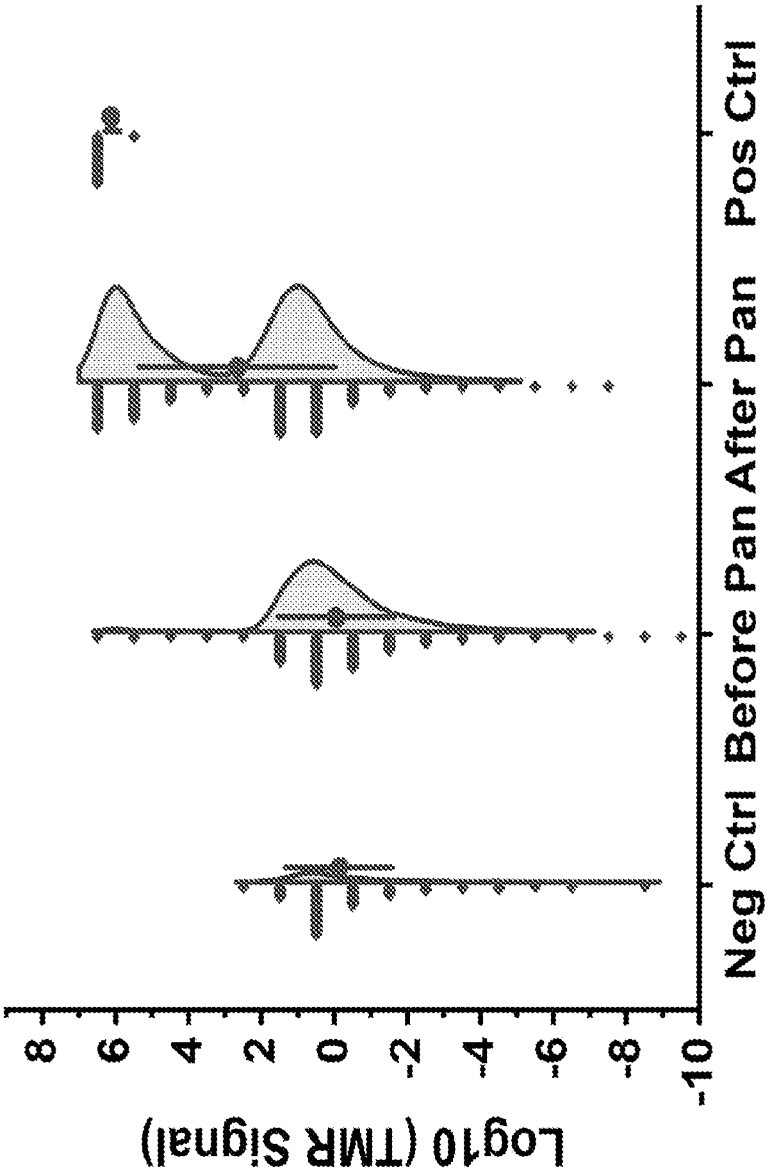
Figure 7C:
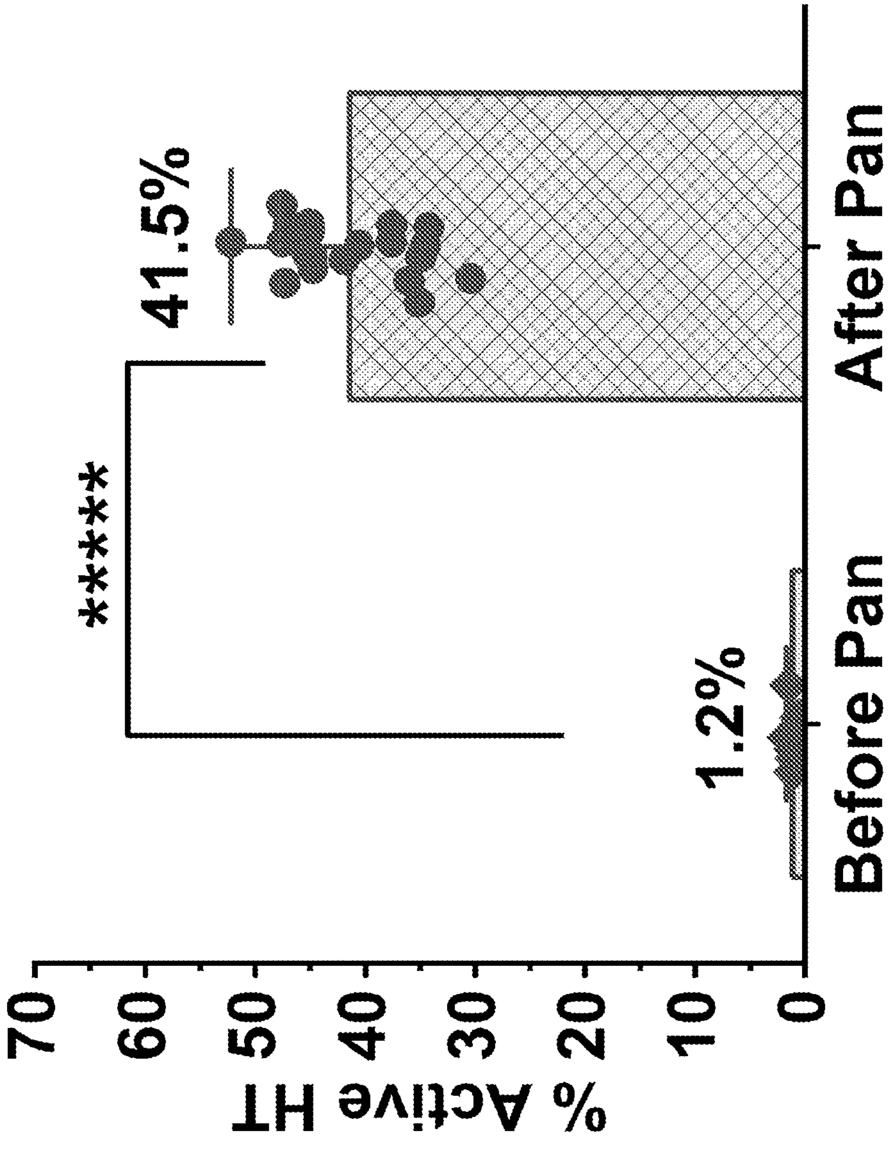
Figure 7D:
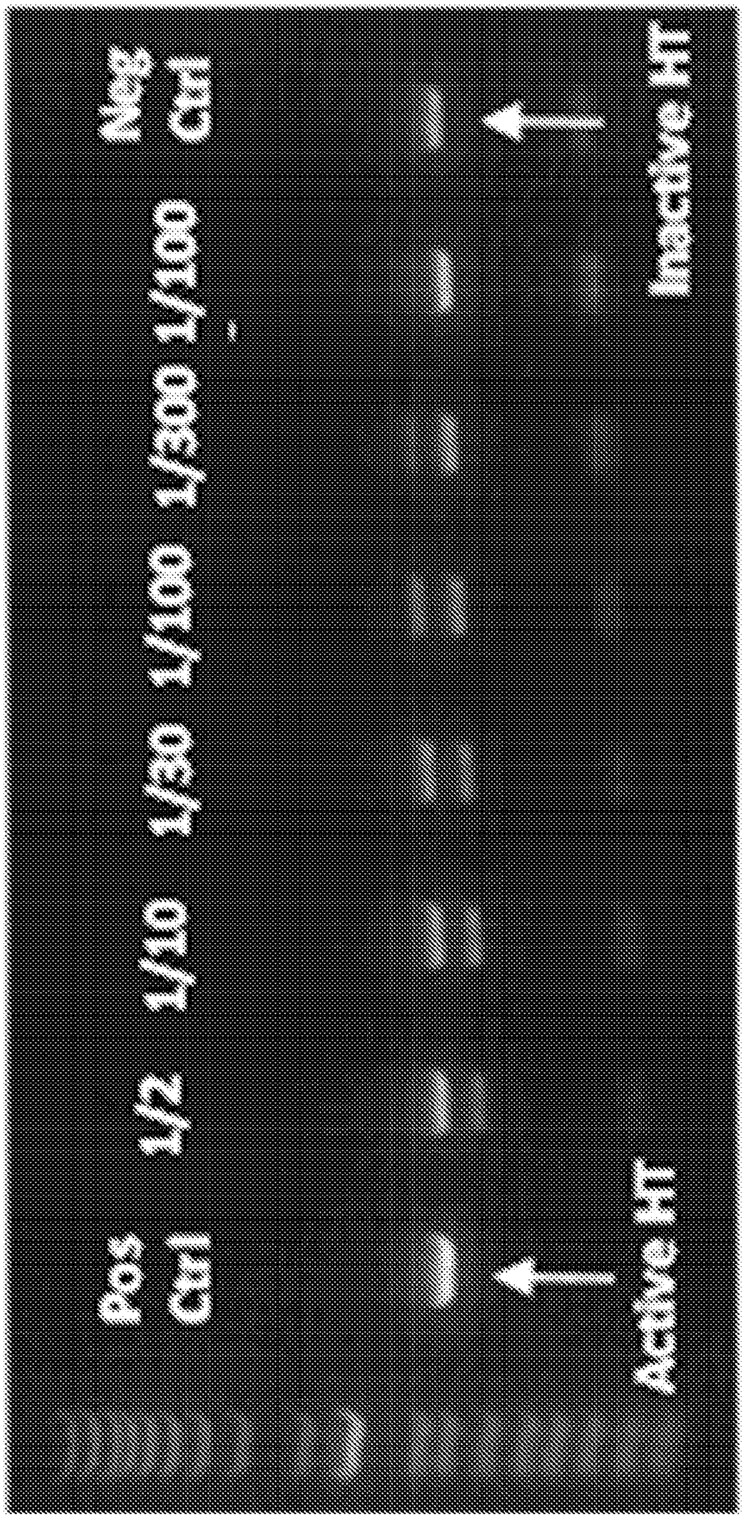

Since the inactive form of HTP has a unique restriction enzyme site, the genetic material corresponding to either active or inactive HTP can be easily distinguished on the agarose gel after digestion with the restriction enzyme (FIG. 7D). This allows even faster experimental design with highly correlative results to the colony plating assay.

Figure 7E:
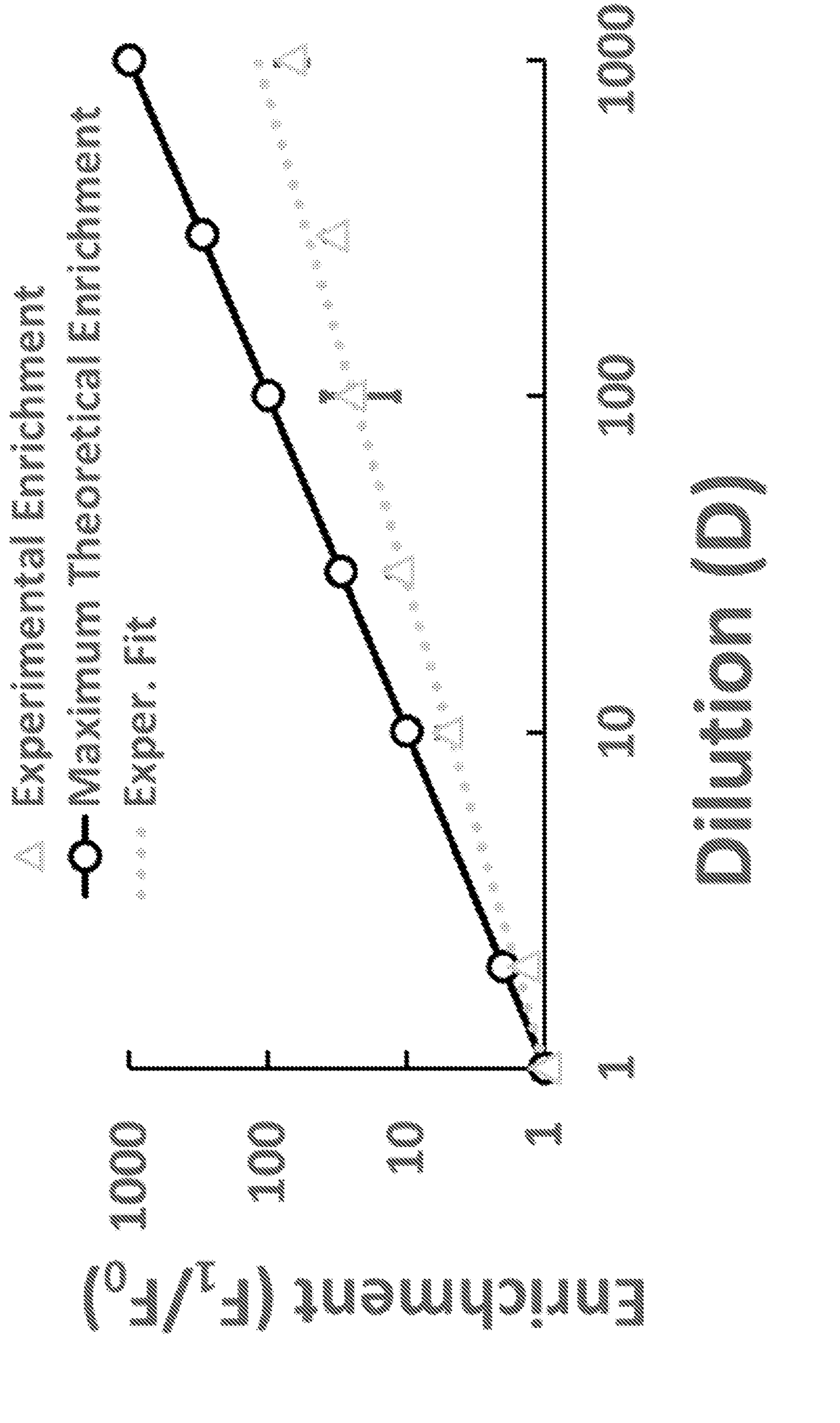

The mix was expressed in vitro, and one round of biopanning was performed and active and inactive HT protein fractions of the recovered genetic material determined. GRIP.1 Display was able to isolate and enrich the active form of HTP from large and mostly inactive protein libraries with a single round of selection (FIG. 7A-FIG. 7E). After just one round of panning, a pronounced bi-modal TMR signal distribution was observed (FIG. 7B), indicating the enrichment for active HTP-containing colonies. For the starting library of 1% activity, the activity enrichment reached 41.5 folds (FIG. 7B and FIG. 7C). In a library with starting activity of 0.1% (1:1000 active:inactive HT proteins), a single round of panning produced ~120-fold enrichment in active HTP fraction (FIG. 7E).

Enrichment of Large NNS-Type Libraries with Unknown Protein Activity Levels Using GRIP Display.

Figure 8A:
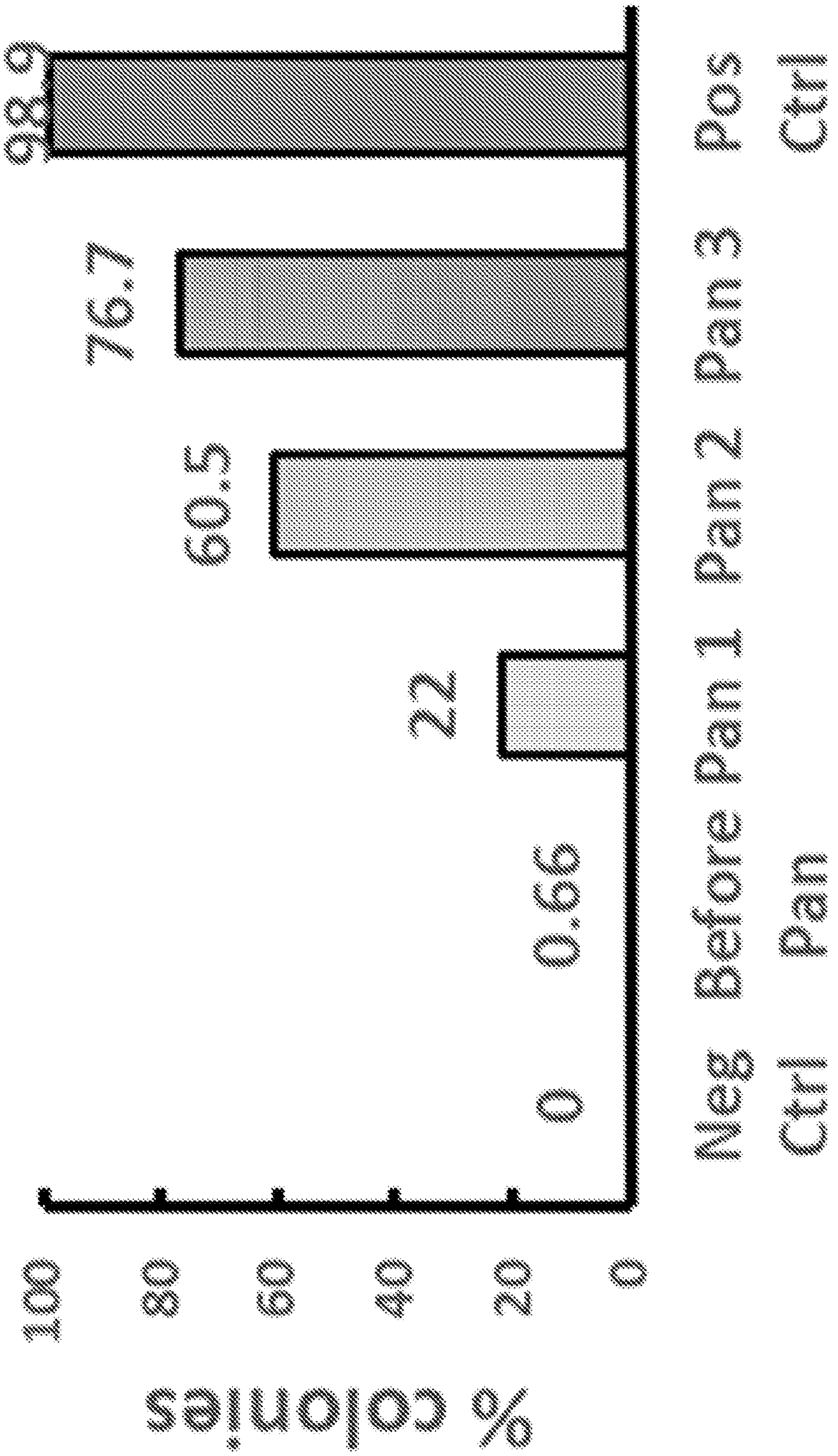
FIG. 8A-FIG. 8C show enrichment of large NNS-type libraries with unknown protein activity.

4-NNS HTP library (106 unique DNA variations): To isolate functional protein variants from much larger libraries, a saturated mutagenesis of 4 HaloTag residues (WFAF) was performed, lining the tunnel near its binding site. The introduced NNS variations resulted in a library pool of $10^6$ unique DNA variants with various affinities towards HT ligand. Several rounds of pans were then performed. After each round, the recovered genetic material was transformed into T7 bacteria and plated on IPTG and HTL-fluorescent dye containing plates to evaluate the activity level of the isolated protein pool. The activity of HTP variants, expressed in the colonies, was evaluated based on the dye signal. The original library had a wide distribution of proteins with different levels of activity. 0.66% of all imaged colonies had TMR signal comparable with WT HT protein. After a single round of panning, a substantial increase in colonies with higher TMR signal was observed, with 22% of the total variants having HTL affinity comparable to WT. In total, three rounds of panning were performed, each time successfully increasing the overall activity of the isolated protein pool. By the third pan, all non-active protein variants were effectively eliminated from the pool, while over 75% of the entire protein variants were now exhibiting HTL affinity comparable to WT HaloTag (FIG. 8A).

Figure 8B:
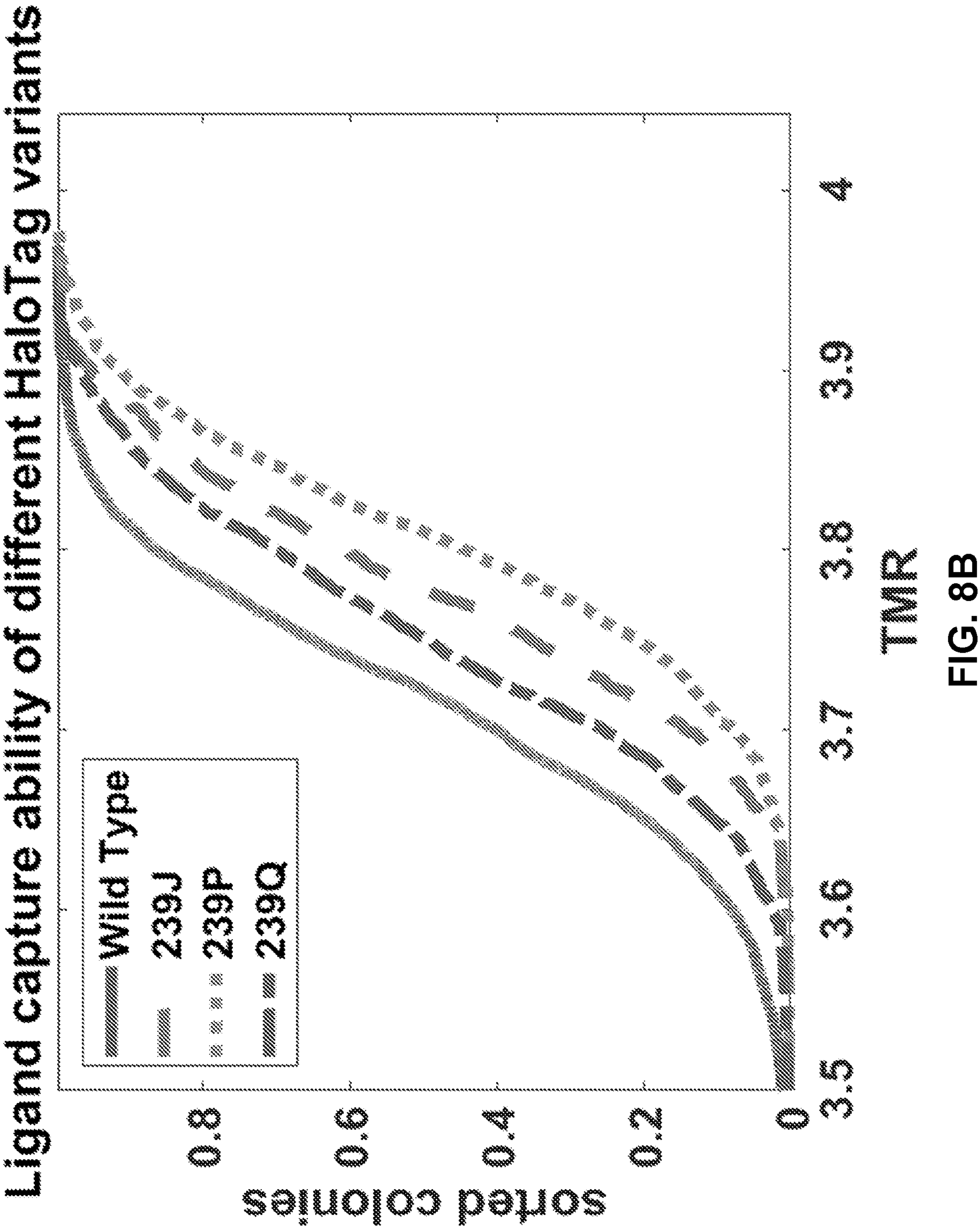

Ninety-five (95) of the brightest colonies were then selected for Sanger sequencing. The majority of the sequences (75%) were identical to the WT HTP, 12% of the sequences contained a single point mutation outside of the mutated region and 3% belonged to a unique sequence FIAF, where two novel mutations were introduced to the binding pocket. Several variants were re-plated separately and the corresponding TMR signal evaluated. The plate assay revealed that all of the HT variants had TMR signal higher than WT HTP (FIG. 8B). For example, 79.5% colonies expressing 239P HTP variant had $\log_{10}$TMR signal larger than 3.75 when plated on HTL-TMR containing agar plates, as opposed to only 35% WT colonies had such high TMR signal.

Figure 8C:
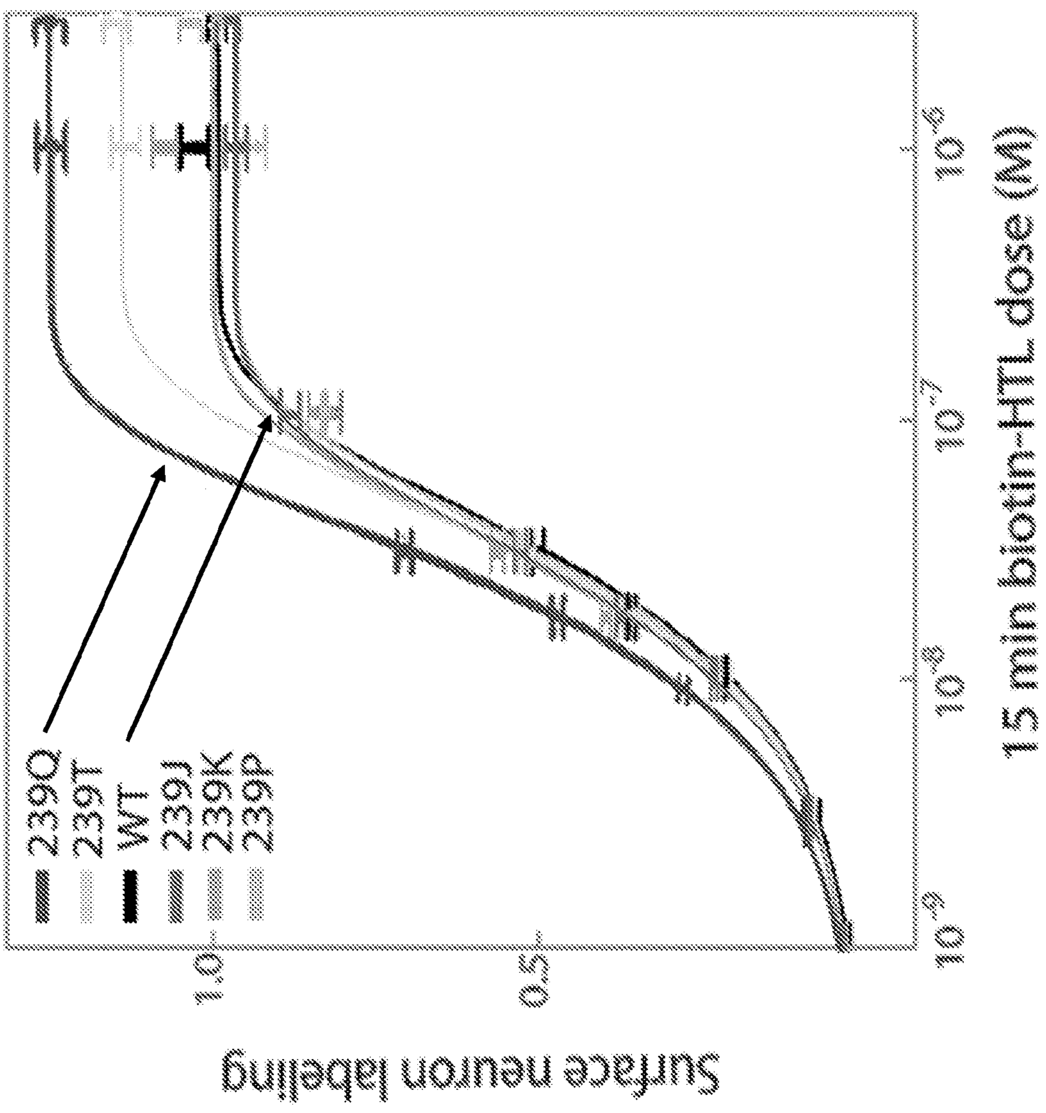

Next, the HTL capture kinetics of the promising variants were characterized in cultured neurons. The HTL affinity of all variants having a single point mutation outside of the targeted binding pocket, did not significantly differ from the WT HTP. One of the variants had a slightly improved neuronal surface trafficking, evident from the higher saturating signal on the graph (FIG. 8C). The FIAF variant that had two novel mutations in the binding pocket, had a slightly improved capture kinetics as well as better surface expression levels compared to the WT HTP.

Overall, GRIP Display was able to enrich a large and mostly inactive protein library of $10^6$ unique DNA sequences for its active members in under three rounds of pans. In this particular set of introduced mutations, the active protein variant was the WT protein itself, with several other variants having similar or slightly improved HTL affinity. Moreover, GRIP Display technology allows to quickly assess whether a particular set of mutations can lead to the discovery of novel variants. Alternatively, it will return a WT variant as the most active member, allowing to make informed decisions with respect to the amino acids that may or may not be important to focus for further optimization process.

6-NNS HTP library (109 unique DNA variants): The 4-NNS library yielded only minor improvement in the kinetics of covalent capture between HTP and its ligand. Expanding the sequence exploration space by increasing the number of saturating mutagenesis residues in the binding pocket of the protein should result in higher chances of isolating a protein variant with significantly improved kinetics. Here, a 6-NNS library was created, where 6 residues were mutated to contain all 21 possible amino acids. As such, this library contains 108 unique DNA sequences corresponding to roughly 86 million unique protein variants.

Figure 9A:
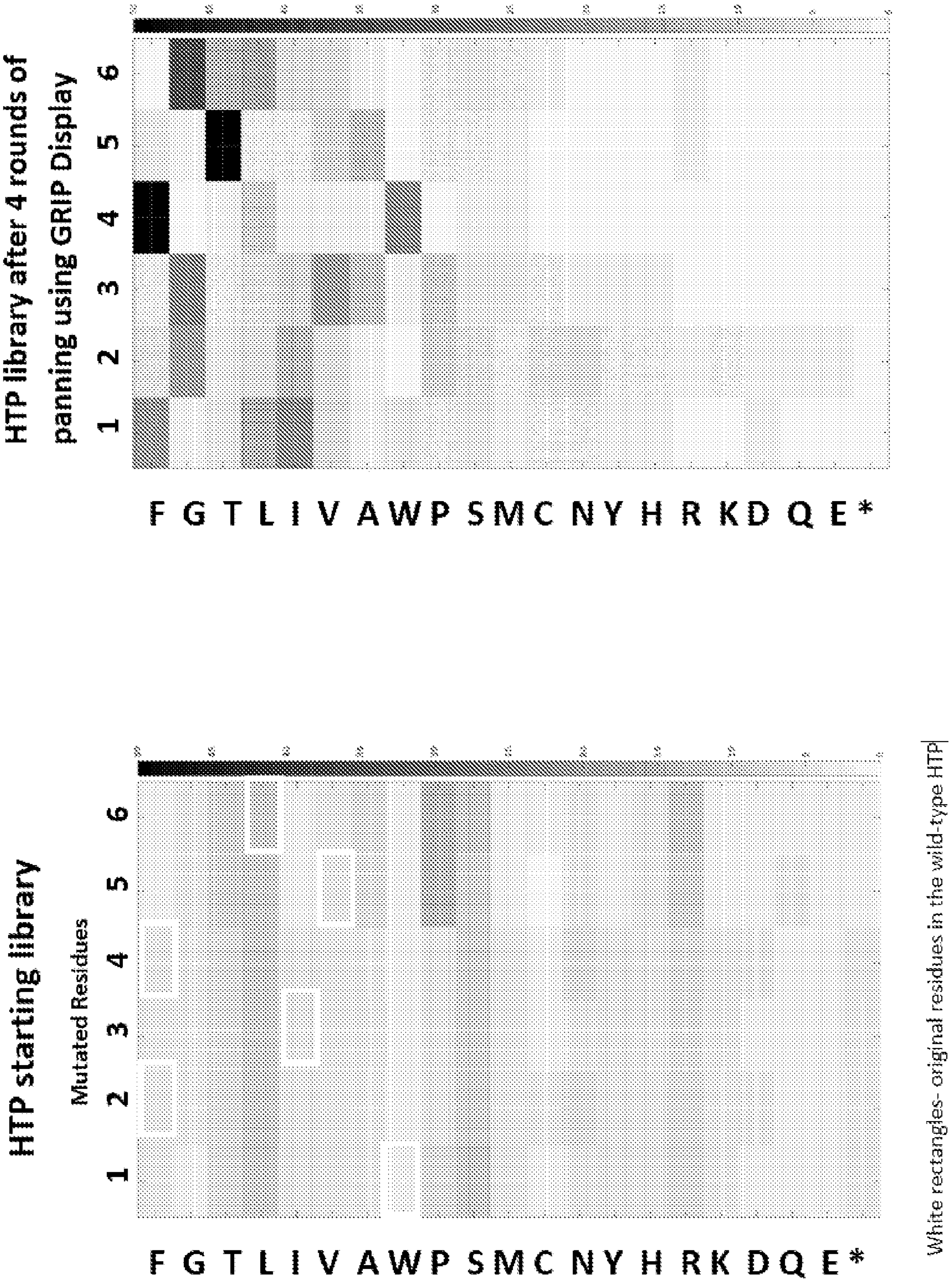
FIG. 9A-FIG. 9B show an example experimental design.

To properly evaluate the quality of the resulting library and make sure it is uniformly mutated without overexpression of any particular residues, an Amplicon Next Generation Sequencing was performed on the library on the mutated region. The NGS revealed the distribution of the mutations to be uniform, indicated by predominantly blue color of the mutation rate heat map (FIG. 9A) Most importantly, there was no overrepresentation of the WT HTP sequence.

Figure 9B:
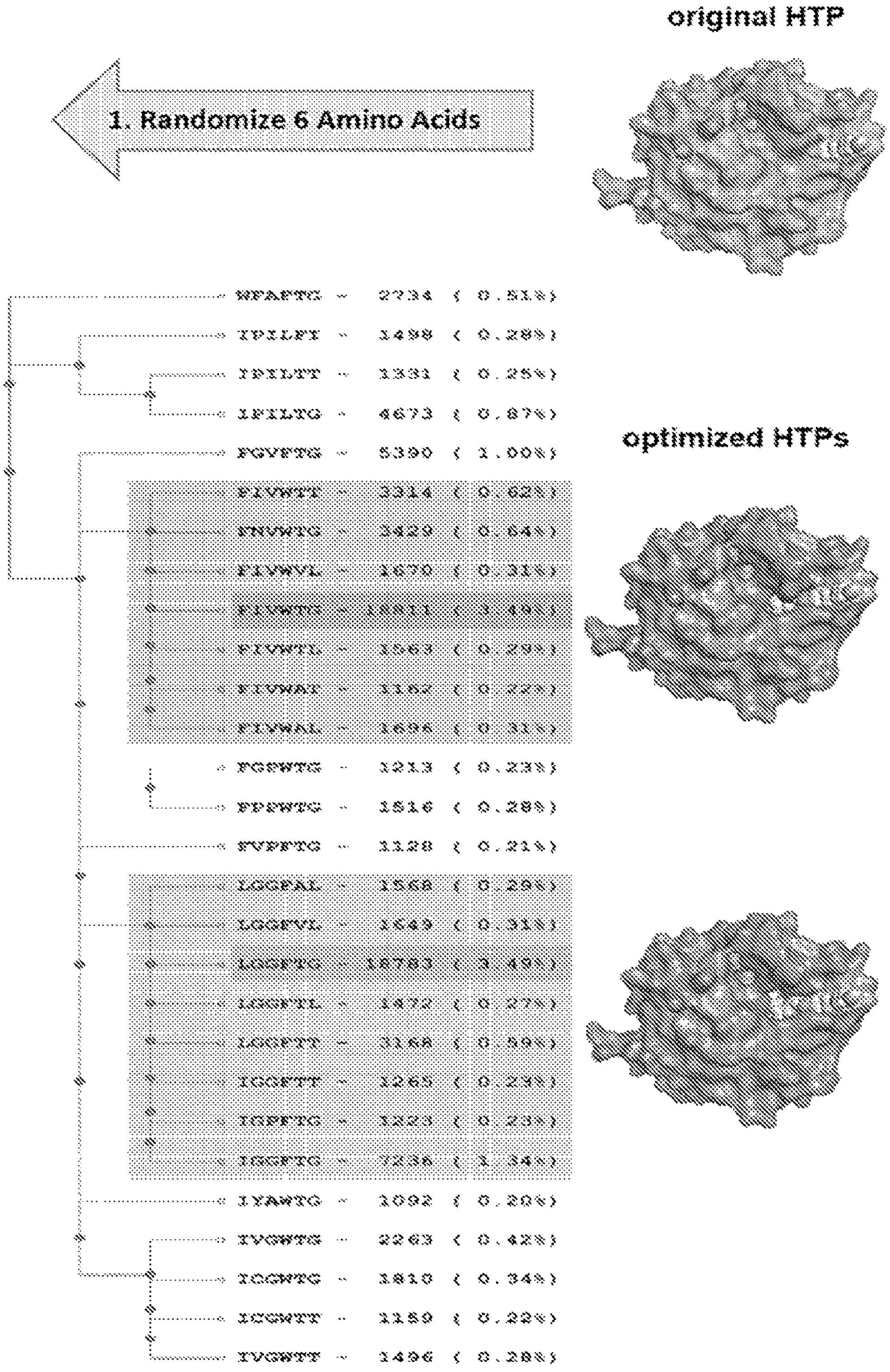

The 6-NNS library was subjected to four rounds of bio-panning against the HaloTag Ligand as previously described, and the isolated genetic material sent for Amplicon NGS. The resulting sequencing revealed the enrichment of several residues at specific mutated locations, annotated 1 through 6 (FIG. 9B). For example:

Position 1 revealed three most favorable residues—Phenylalanine (F), Leucine (L) and Isoleucine (I)—that are different from the original Tryptophan (W). All three mutations are very conservative with the original residue, but the trend here is the substitution of the bulky aromatic ring side chain group (indole) with a smaller group, opening up the pocket for easier access of the ligand.

Position 2 predominantly favors Glycine (G) with Isoleucine coming second. Yet again, the overall trend here is to exchange the bulkier aromatic ring of Phenylalanine (F) with smaller side group.

Position 3 introduces Glycine (G) and Valine (V) in place of Alanine (A), both of which are conservative changes.

The original residue Phenylalanine (F) in position 4 is preserved. The appearance of a less predominant Tryptophan (W) was observed here, which indicates that an aromatic ring structure is important and is preferable at this specific location, possibly creating a pi-staking interactions with the ligand.

Threonine (T) is predominantly favored at position 5, as opposed to the original residue Valine (V). This substitution is very conservative, adding a polar —OH group to the pocket, which might help in creating additional interaction between HTL and the pocket lining.

Finally, the most abundant residue at position 6 is Glycine (G) followed by the original Leucine (L), making the pocket wider by this conservative substitution with less bulky residue.

Two distinct trends are observed: the tendency to widen the binding pocked with simultaneous introduction of several additional interaction points. The widening of the pocket most probably affects the $k_{on}$ of the system by making the tunnel easier to access, while the introduction of an extra possible interaction between the pocket wall and the ligand probably has a stabilizing effect on the ligand inside the pocket, which directly affects the $K_{off}$ of the system. As a result, longer time spent inside the pocket allows the ligand a better opportunity to create the covalent bond. Together, it is logical that these mutations are working towards the overall optimization of the HTP-HTL kinetics.

Next, the actual combinations of mutations collectively present in the most abundant strands were evaluated. The NGS data was grouped according to the top most abundant sequences, where all six mutation positions were looked at simultaneously. The emergence of several different families of variants were observed, with slight variations within each family. The two leading families, based on the overall abundance, had the first four positions as FIVW (8.25% of total reads or 82.5K reads per million) and LGGF (8.09% or 80.9K rpm). The most frequently observed residues in the last two positions were TG (33.9% or 339K rpm). Considering all six positions together, FIVWTG and LGGFTG had 3.49% of total abundance each, making them the most frequently appearing sequences in the library (FIG. 9B). A PyMol model of the resulting proteins was constructed using the crystal structure of the wild type HTL as a template. The resulting models show that the opening of the pocket got significantly larger (FIG. 9B), as shown by the analysis of the overall observed trends.

Finally, partially mutated pocket WFAFTG, where the two last positions changed from VL to TG, had a 5K rpm abundance, compared to the 2.8K rpm of the original wild type sequence WFAFVL. In fact, the abundance of the wild type sequence decreased from biopan 3 to biopan 4 by over 50%, indicating that it is no longer the best variant in this large protein pool. Work is being done to complete a full characterization of the binding kinetics of the prominent HTP variants both in vitro via SPR and in vivo on cultured neurons.

Interestingly, all six positions received a novel mutation in the FIVWTG sequence compared to the wild type HTP (WFAFVL), and 5 out of 6 positions got mutated in the LGGFTG variant. Considering the plethora of possible variations in the 6-NNS library, it would be nearly impossible to deduce these particular combinations as the top winners solely from computational modeling of the binding pocket. This, combined with the fact that it took less than a month to receive the sequences of the most promising leads, is a strong indication that GRIP Display technology represents an unrivaled alternative to both the existing display technologies as well as to the alternative methods of computational modeling. The systems and methods provided herein are also able to show the suitability of GRIP Display for the development of functional large proteins and enzymes as they are the most challenging biological systems to improve as well as prove to be potent in evolution of functional antibodies, short and long peptides, and the like as well.

Example 2

GRIP.2 Design and Characterization

The goal of this Example was to improve avidity by designing rigid 3D-constrained versions of tandem BoxB and tandem λ epitopes. Unlike beads on a string, rigid 3D-constrained designs can improve avidity through the principle of entropy minimization. The result is an interlocking structure analogous to a dovetail junction. Here, the development of GRIP.2 was achieved via design of two elements:

Rationally design an mRNA sequence that folds reliably into a rigid 3D conformation, thus orienting BoxB haipin epiotpes with minimal flexibility.

Rational design of a complementary protein, including a well-folded protein scaffold that orients the positions of λ peptides into a rigid 3D conformation, designed to complement the mRNA designed above.

The stable mRNA structure was denoted "ToyBox" and the corresponding protein "CLAW" given their physical appearance. The resulting technology achieves three fundamental benefits:

A "single read" design, where the binding of CLAW protein to the ToyBox on its mRNA prevents the mRNA from being translated more than once, ensuring a 1:1 stoichiometery of mRNA:protein.

Compatibility to harsher washing conditions (owing to enhanced linkage stability).

Substantially improved biopanning yields (owing to linkage stability and 1:1 stoichiometry).

Rational Design and 3-D Folding Predictions of $boxB_{Toy}$

Figure 10:
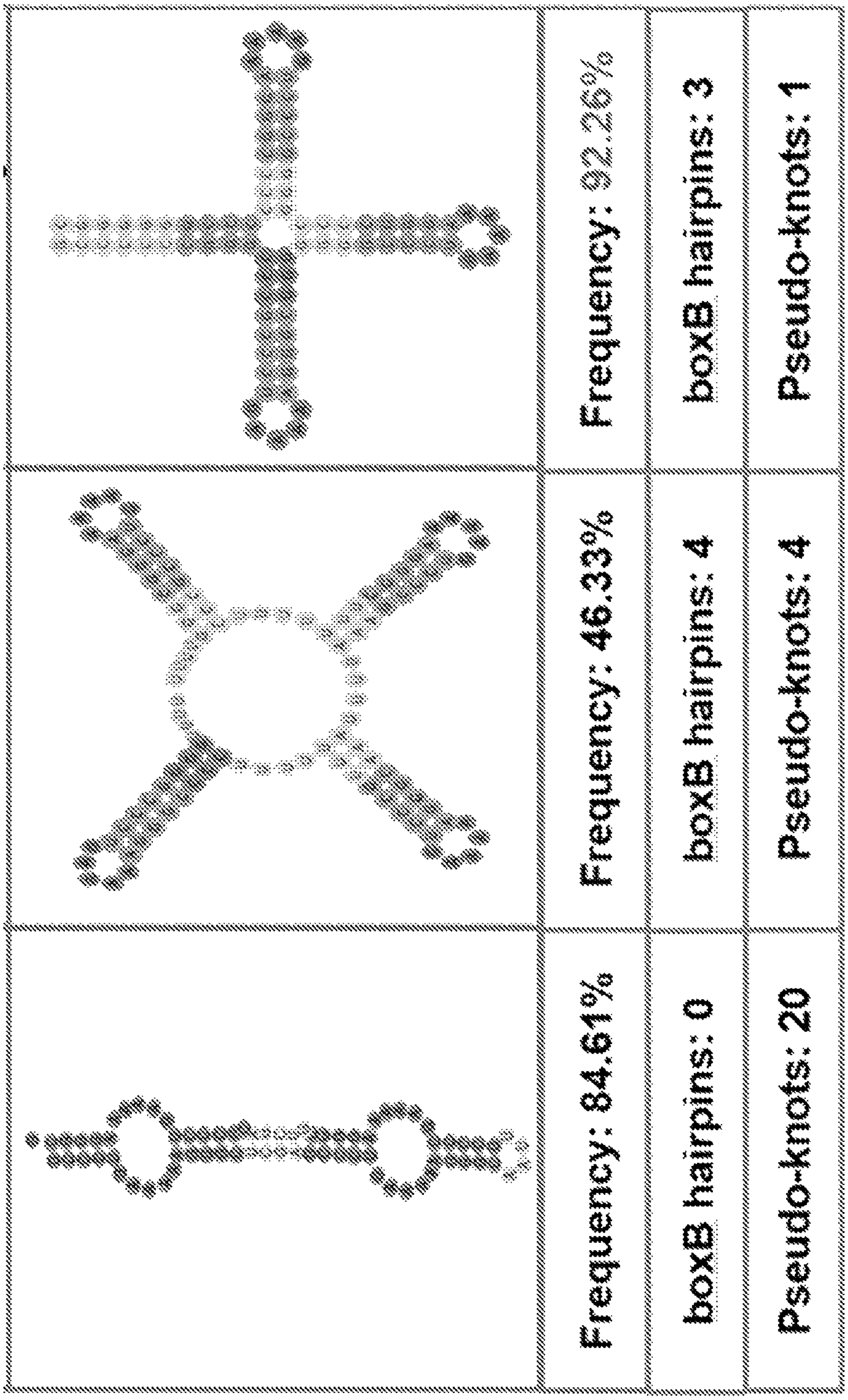
FIG. 10 shows comparative rational design of varying presentation of boxB domains via 3-D structure, abundance frequency, hairpin structures, and pseudo-knots.
Figure 18:
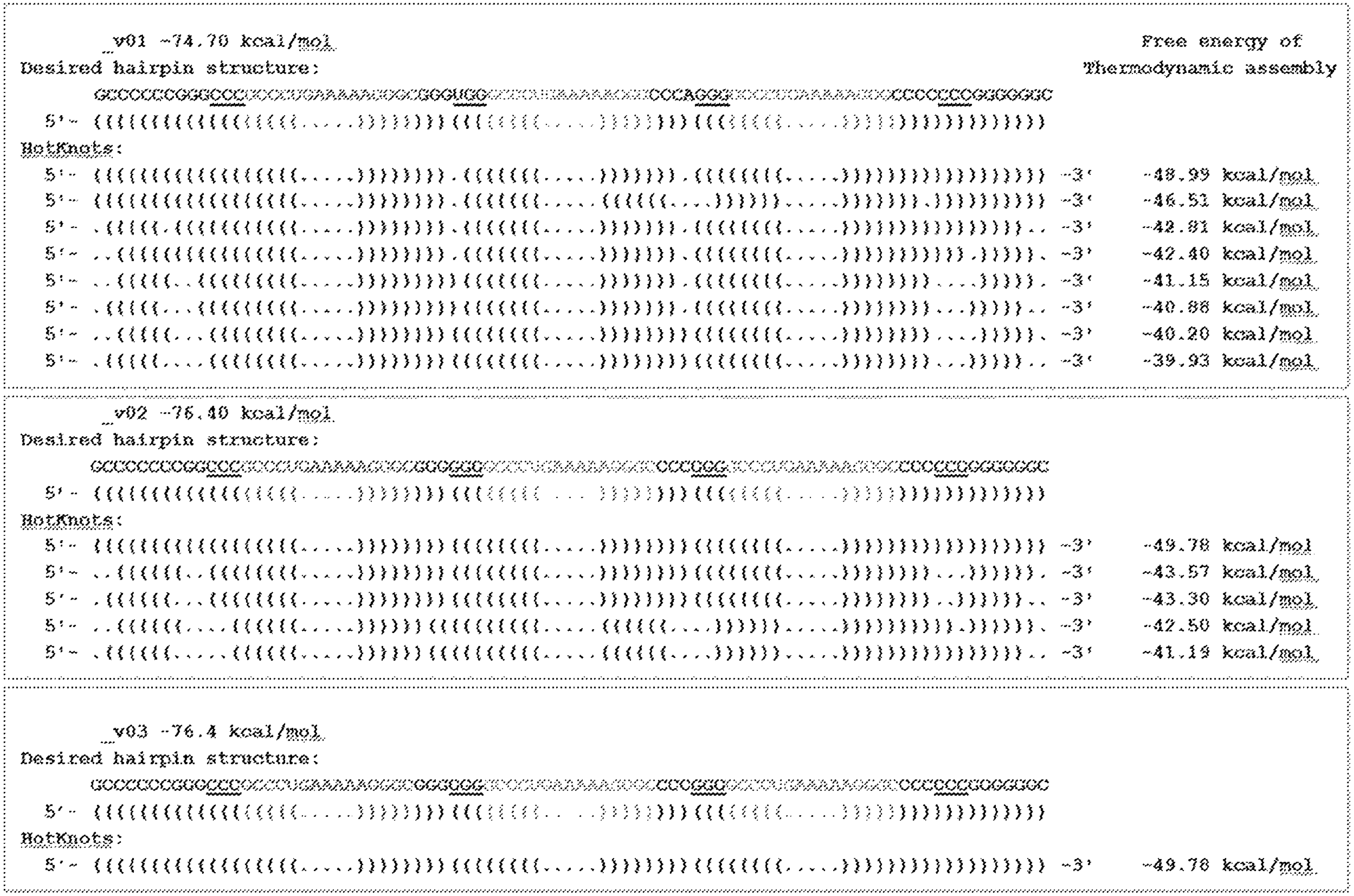
FIG. 18 shows RNA sequences and their corresponding predicted folding in the dot-bracket format. The last sequence has a single alternative conformation.

As described in the design of GRIP.1, the introduction of unique stem extensions in boxB regions resulted in local stem-loop formation of the hairpins, as opposed to the long-range collapsed folding that was observed in previous boxB designs (FIG. 18). However, upon closer examination of the complexity of RNA folding, it became clear that the presence of multiple pseudo-knots might affect the overall stability of the RNA-peptide interaction. For example, the 4boxB structure (in GRIP.1) is predicted to exhibit 4 alternative folding patterns, predicted to represent 54% of the overall structure frequency (FIG. 10). In other words, over half of the time the 4boxB mRNA strand likely does not fold into the desired tetramer of hairpins. Therefore, efforts must be concentrated on minimizing the occurrence of the pseudo-knots.

RNAfold were used to predict the most stable RNA folding structure based on provided sequence, and hotknots to outline the dot-bracket format of the pseudo-knots associated with the structure. Hotknots web tool used Dirks& Pierce as their predictive model. Finally, Rosetta and RNA-composer were utilized to create the 3D structural models based on the obtained secondary structure. Several structures were considered, however, most of them had multiple alternative hotknots. Nevertheless, using all the tools above, a unique RNA sequence that resulted in a structurally stable boxB trimer with a single hotknot was found. The key intuition that led to the highest stability was to eliminate flexible linkers and to circularize the design with an additional interaction between the start and end of the sequence. The resulting structure contained a trimer of BoxB elements and is predicted to fold into the desired conformation 92.3% of the time (FIG. 10).

Figure 11A:
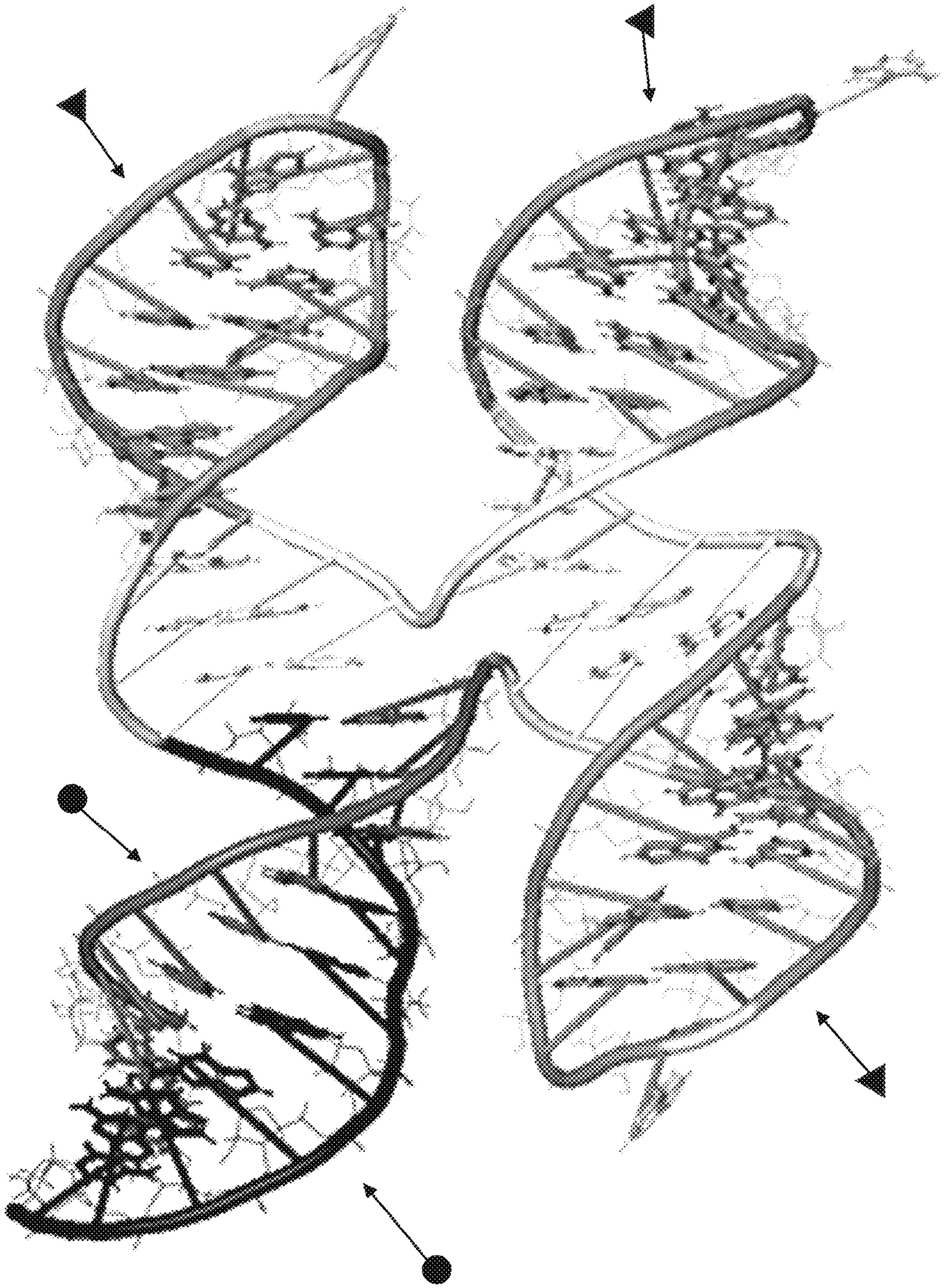
FIG. 11A-FIG. 11B show 3-D folding prediction of two conformations for the Toy boxB trimer. The RNA hairpins are denoted with a "▲". The starting and ending portions of the overall RNA are found in folds denoted as "●".
Figure 11B:
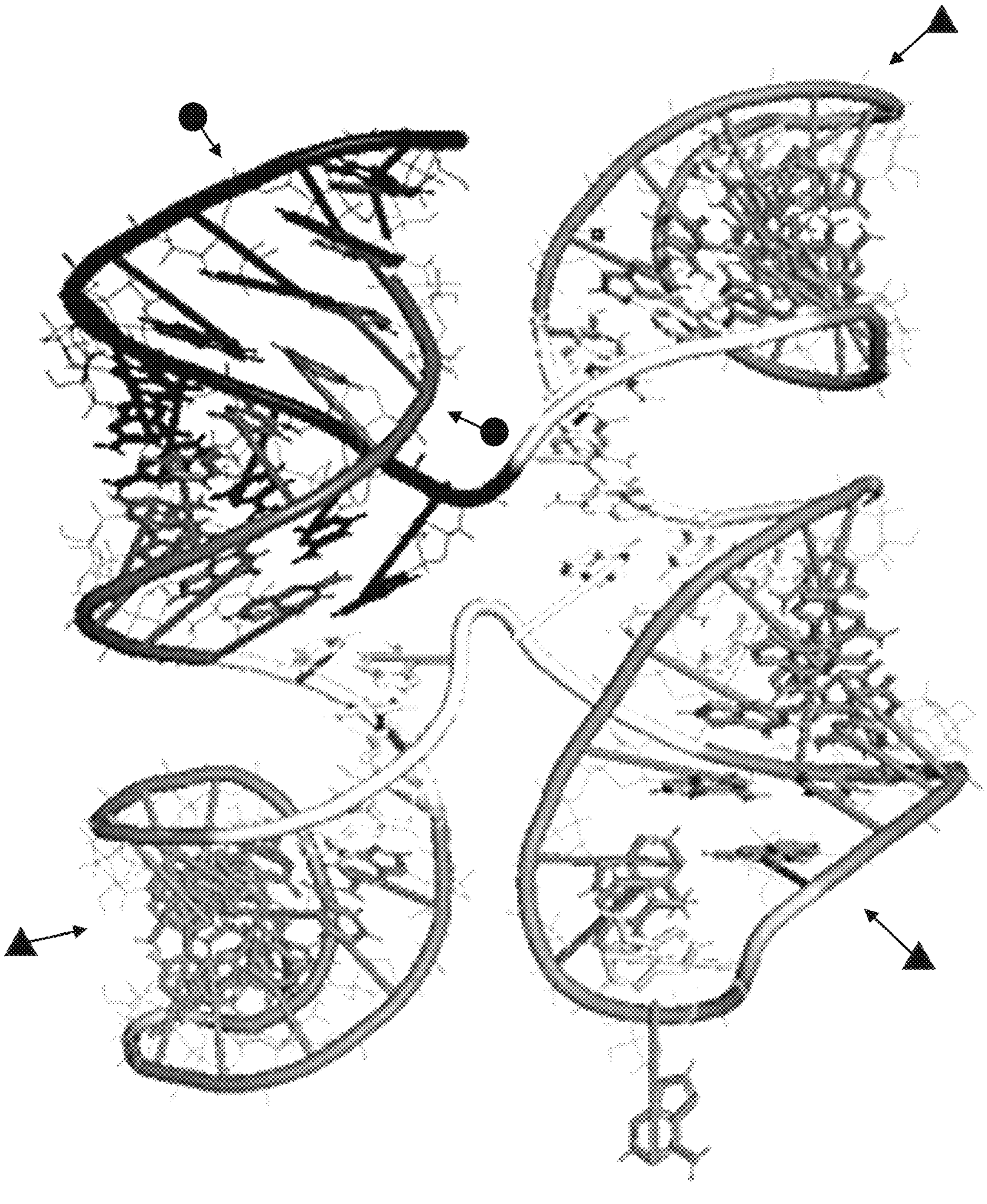

The dot-bracket indicates that the primary and the alternative conformation of the $boxB_{Toy}$ trimer are the same, meaning that 3 hairpins are being formed of the same length and composition. The 3-D model of both the primary and the hotknot structures revealed that the 3 hairpins are oriented in slightly different spatial directions and have a nearly planar conformation (FIG. 11A & FIG. 11B). Moreover, the 5 bases in each hairpin that directly participate in the interaction with λ peptide, are oriented differently as well. Where in conformation 1 the base marked in pink color is oriented outwards, while in conformation 2 it changes position closer to the inner part of the loop, while another base is now pointing outwards.

$\lambda_{CLAW}$ Design and Assembly

Figure 12A:
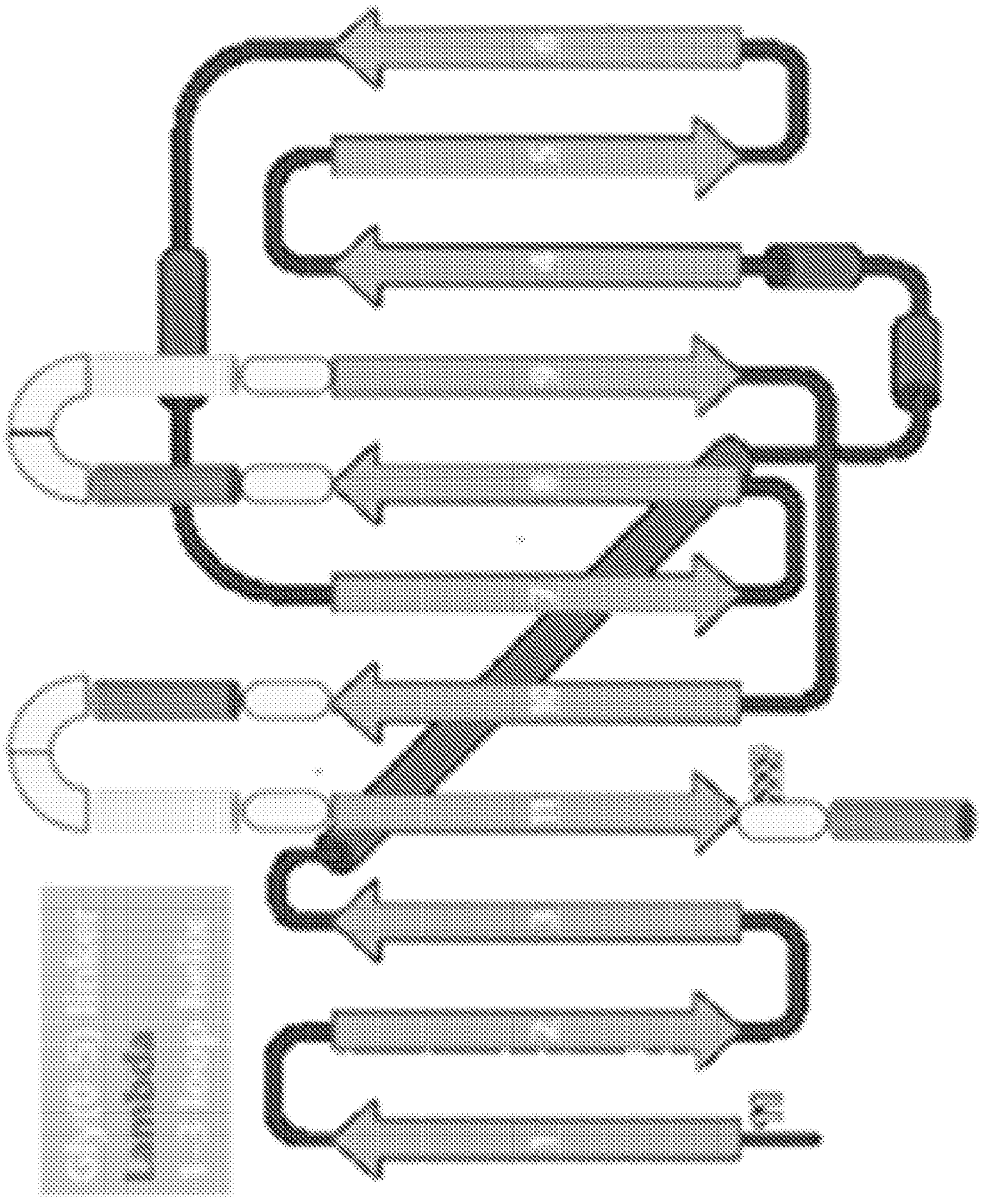
FIG. 12A-FIG. 12D show an overview of CLAW variants.
Figure 12B:
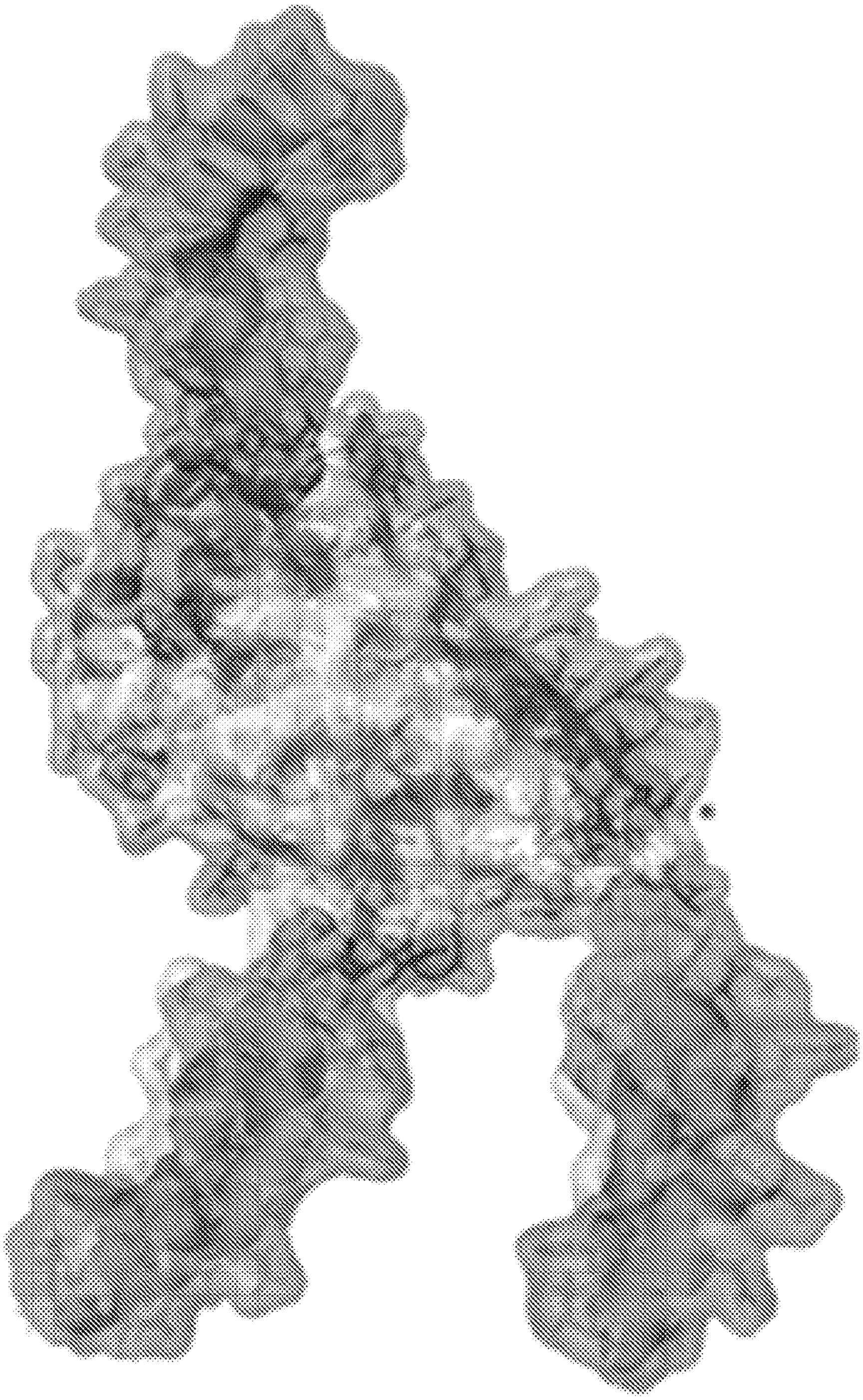
Figure 12C:
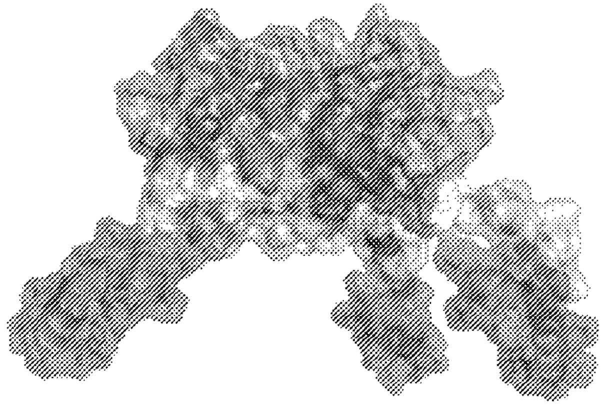
Figure 12D:
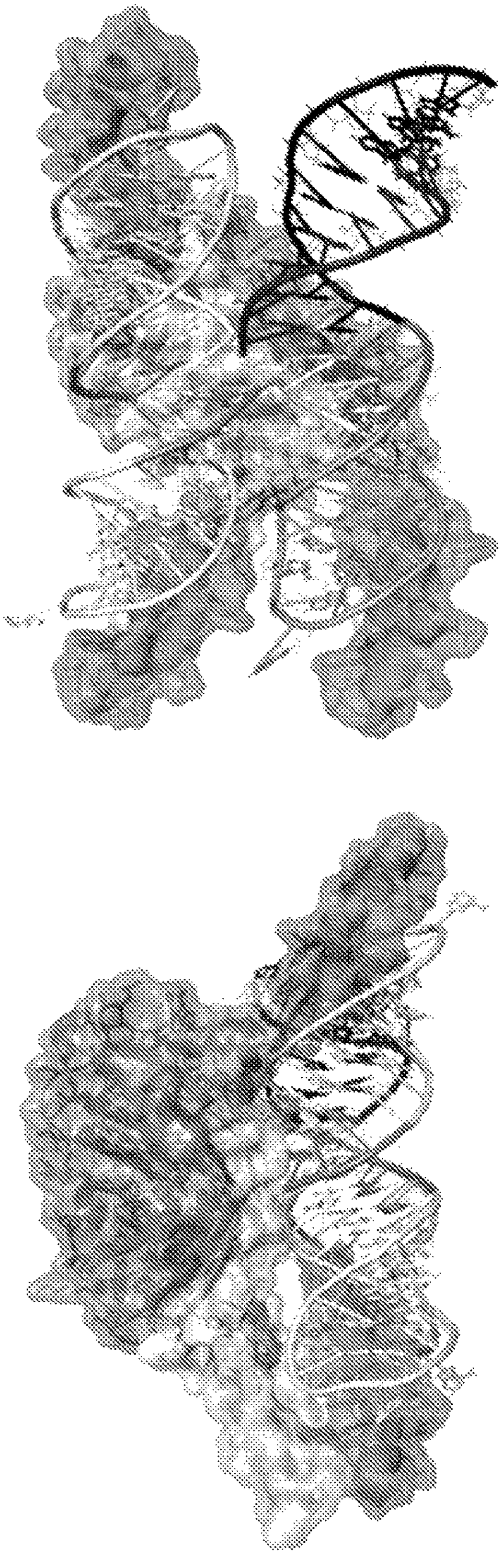

To complement the nearly planar boxB trimer called “Toy”, 3λ peptides was incorporated into a GFP scaffold such that the orientation of the peptides was aligned with the active site of each RNA hairpin. The resulting protein was denoted “CLAW” for its resemblance to the 3-finger claw of arcade machines (FIG. 12B, FIG. 12C, and FIG. 12D). Its 10 loops between 11 beta sheets were systematically evaluated for the successful insertion of extra residues. Loop #9 and loop #10 were used to insert two A peptides, while the 3$^{rd}$ peptide was placed adjacent to the C-terminus of GFP (FIG. 12A). The number of flexible Glycine residues as linkers was varied between the λ and the protein and introduced 1 to 3-loop helixes adjacent to each λ to close loops 9 and 10. In addition, the truncation of the last five GFP residues (209-213) adjacent to the beginning of loop 10 was explored.

Evaluating Genotype-Phenotype Linkage Stability and Fidelity of GRIP.2

To create and assess the effectiveness of GRIP.2 Display (CLAW-Toy design), the covalent capture reaction that occurs between the HaloTag protein (HTP) and its chemical ligand (HTL) was used. The ligand with biotin were labeled and utilized streptavidin magnetic beads to extract the captured proteins. The linkage stability and fidelity between the hairpin $boxB_{Toy}$ and its peptide partner $\lambda_{CLAW}$ were evaluated by mixing the DNA encoding for two variants of HTP: its active form that binds the ligand efficiently and irreversibly, and its inactive form, where the binding pocket was modified to stop the reaction from occurring. The DNA mix was expressed in vitro via the PUREfrex protein expression kit and panned against the HTL-beads. The amount of the isolated DNA was quantified via qPCR measurements and compared to the GRIP. 1 Display (4boxB-λ design). The DNA was digested with a restriction enzyme that has a unique digestion sequence encoded in the inactive HTP form. In this manner, the active HTP band was separated from the inactive HTP in 1% agarose gel. The intensity of each band was measured via gel image processing in Matlab, and the live:total ratio was calculated. The data was normalized for the length of the band.

Figure 13A:
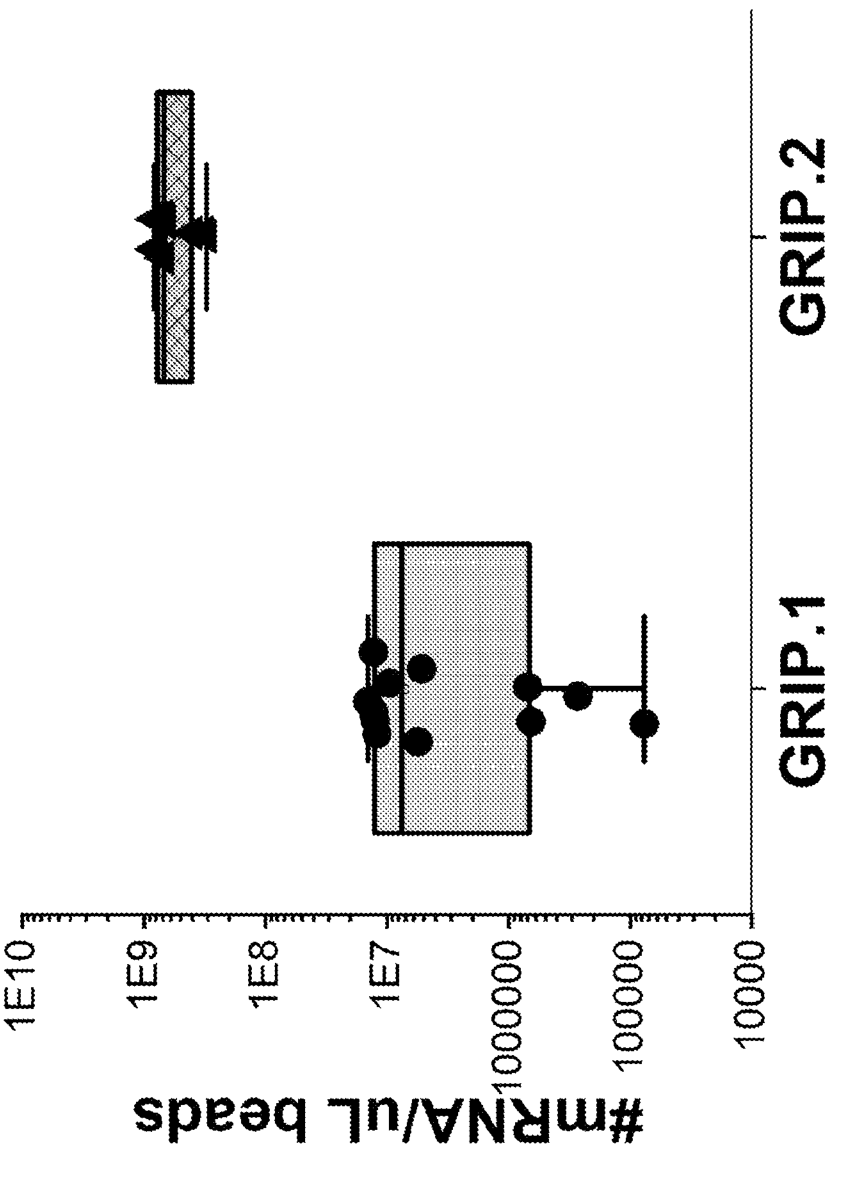
FIG. 13A-FIG. 13D show GRIP.2 retains more total genetic material compared to GRIP.1.
Figure 13B:
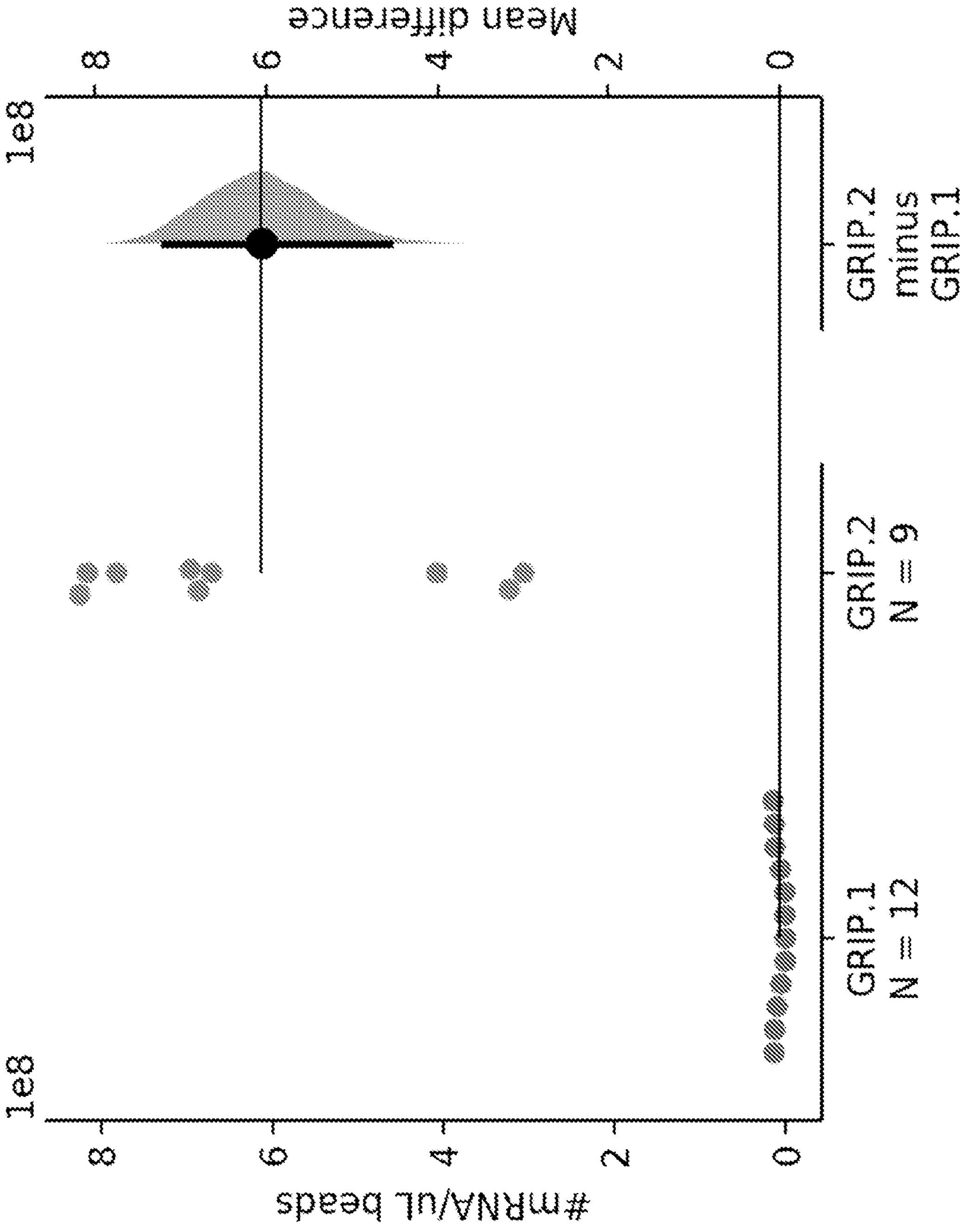
Figure 13C:
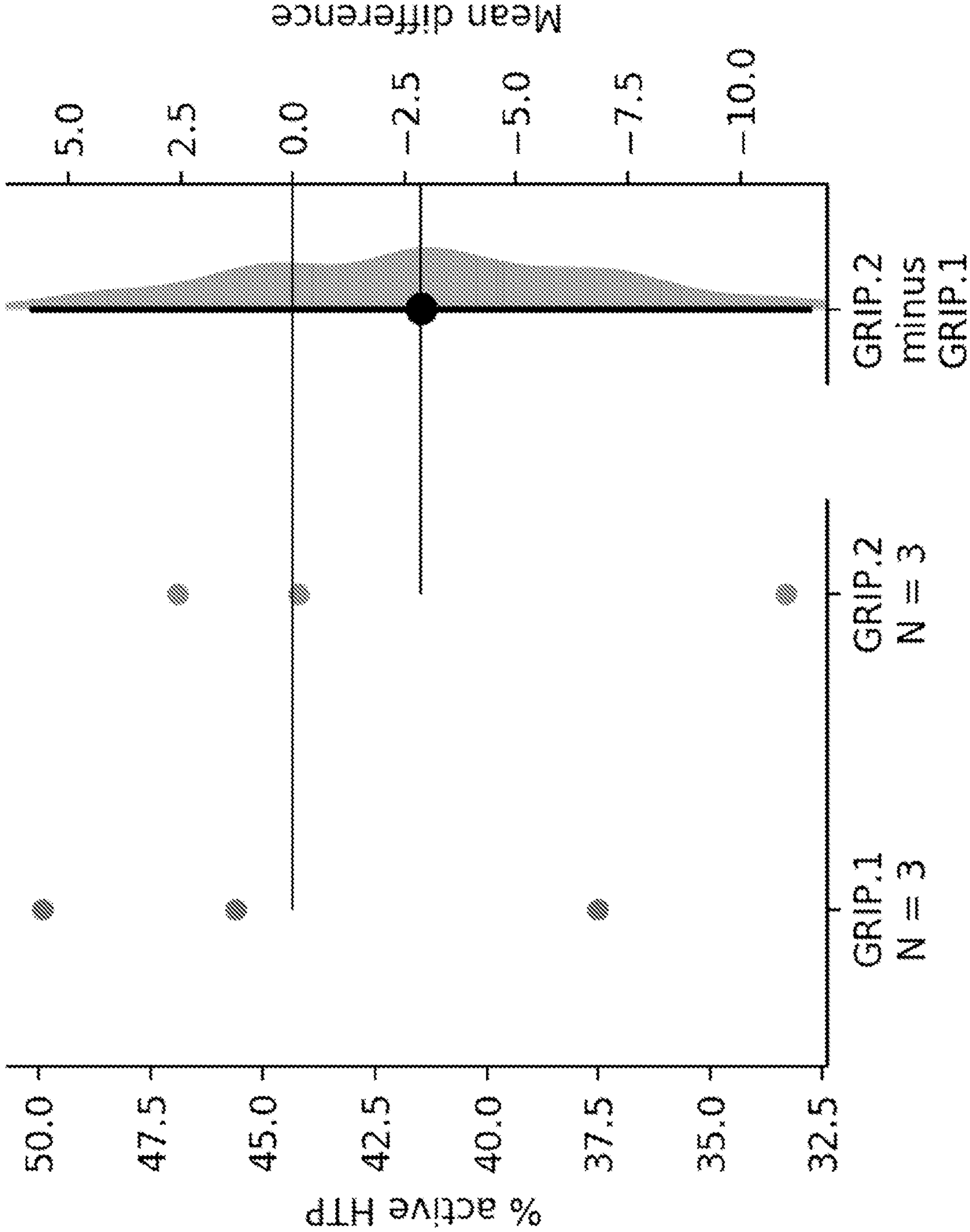
Figure 13D:
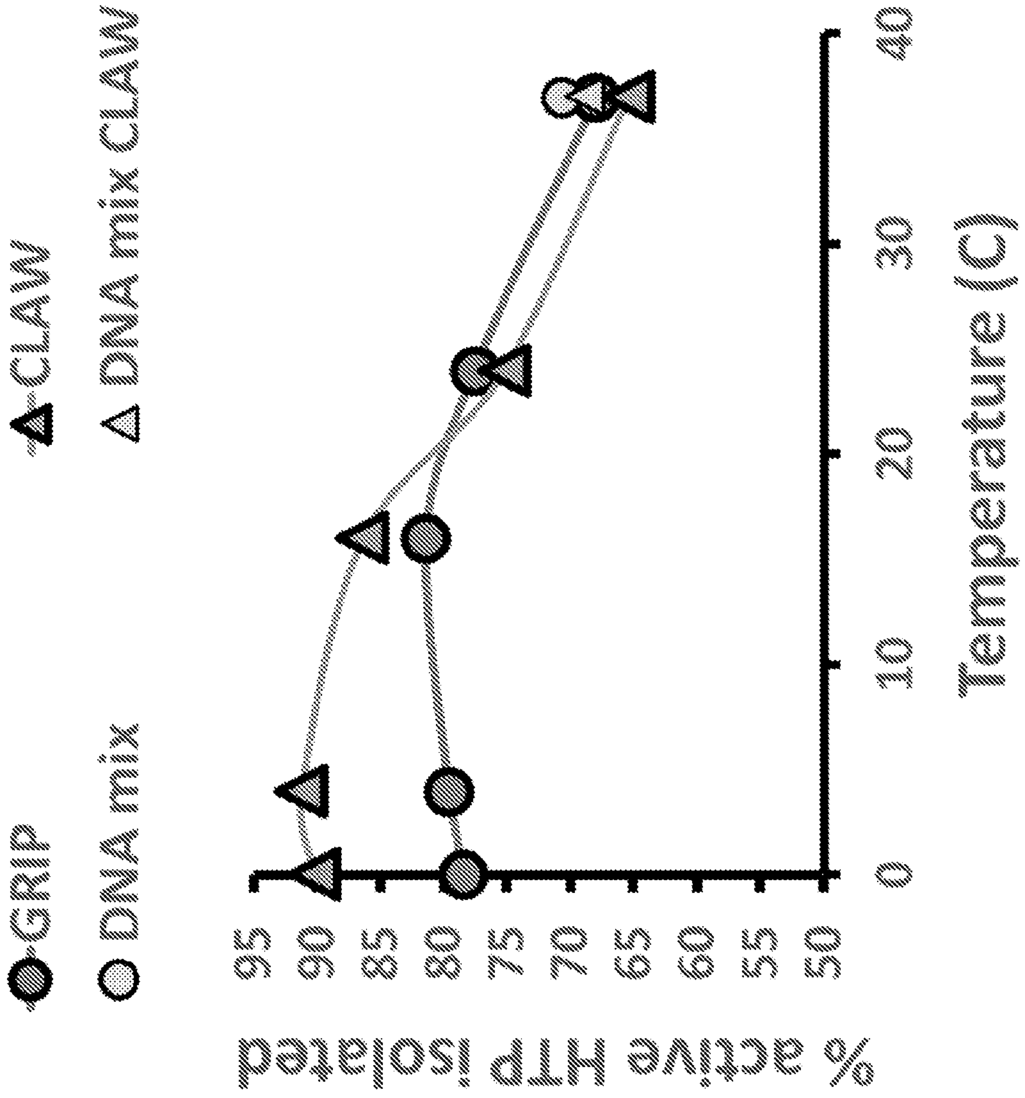

GRIP.2 exhibits the ability to robustly retain more overall genetic material compared to GRIP.1 (FIG. 13A and FIG. 13B). The difference in quantified mRNA after panning varies anywhere from 10 to 100-fold, depending on the experimental protocol. Interestingly, the fidelity of the Claw-Toy system (having a trimeric boxB and three λs) is comparable to the fidelity of the tetrameric GRIP.1 Display (FIG. 13C and FIG. 13D).

Figure 16:
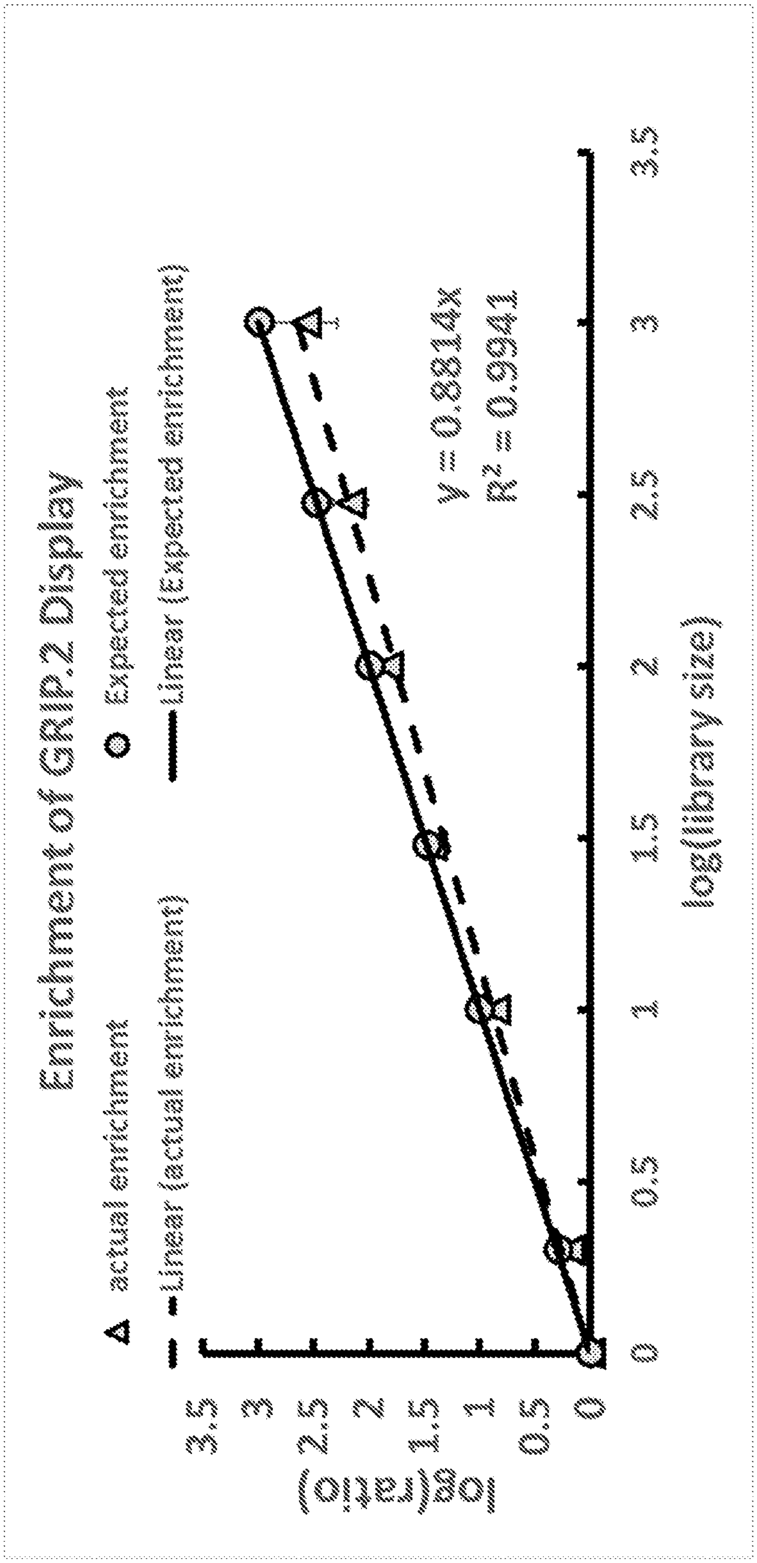
FIG. 16 shows the enrichment of the pseudo-library after 1 pan using GRIP.2 Display. The size of the library is inversely proportional to the starting activity and is plotted against the enrichment of the library as a log scale. Black line represents maximum possible enrichment for each corresponding library. N=3.

To evaluate the enrichment capability of GRIP.2 Display in the context of large protein libraries a similar experiment was performed with enrichment of pseudo-libraries with different levels of active members. To do so, the DNA encoding the wild type HT protein and its inactive version (where the active site was mutated such that activity of the protein was lost) were mixed at different proportions, creating pseudo-libraries with known initial activity levels. The initial activity levels ranged from 0.1% to 100%. The mix was expressed in vitro, and one round of bio-panning was performed and active and inactive HT protein fractions of the recovered genetic material was determined. GRIP.1 Display was able to isolate and enrich the active form of HTP from large and mostly inactive protein libraries with a single round of selection (FIG. 16).

Figure 14A:
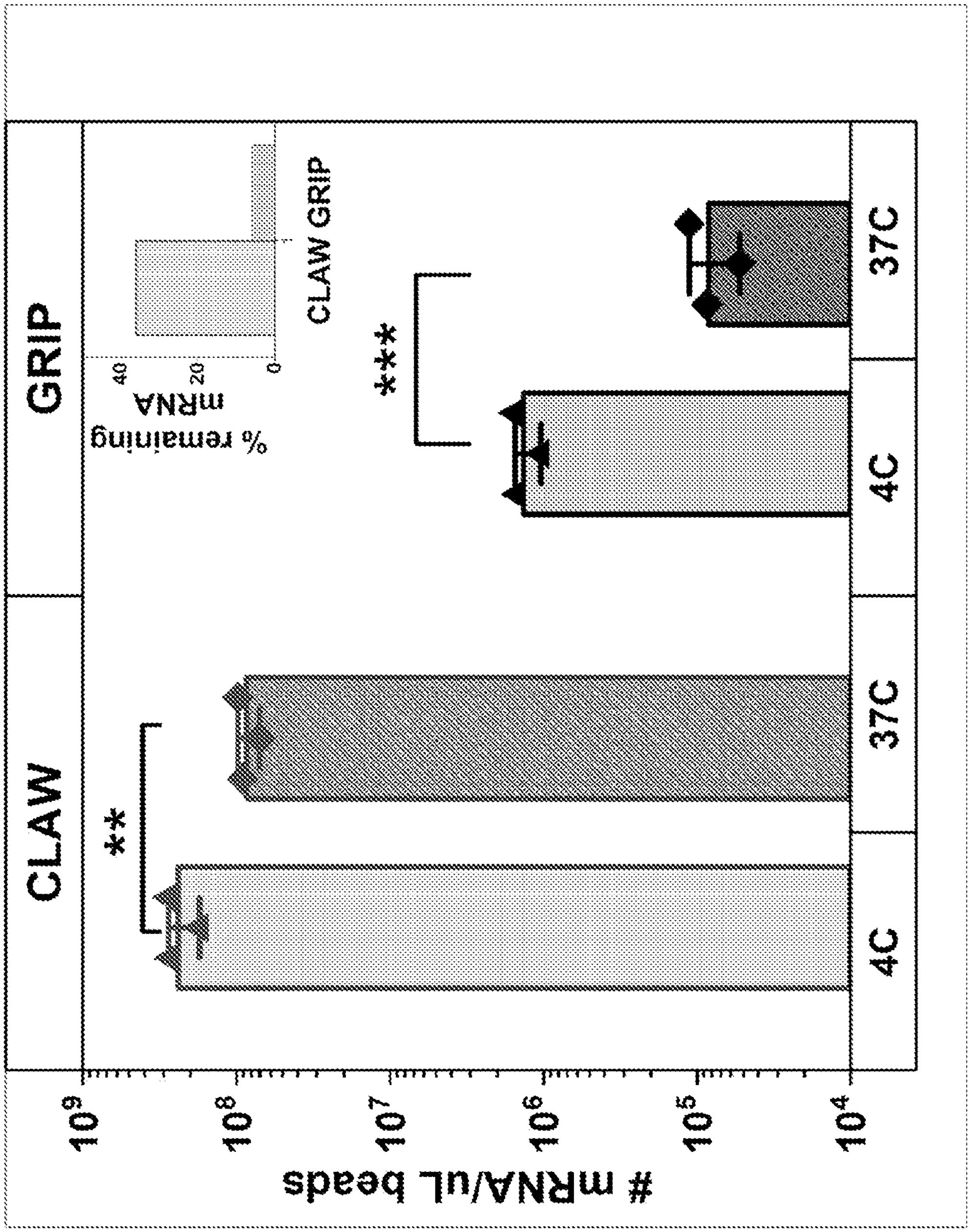
FIG. 14A-FIG. 14C show GRIP.2 retains more genetic material at harsh washing conditions.
Figure 14B:
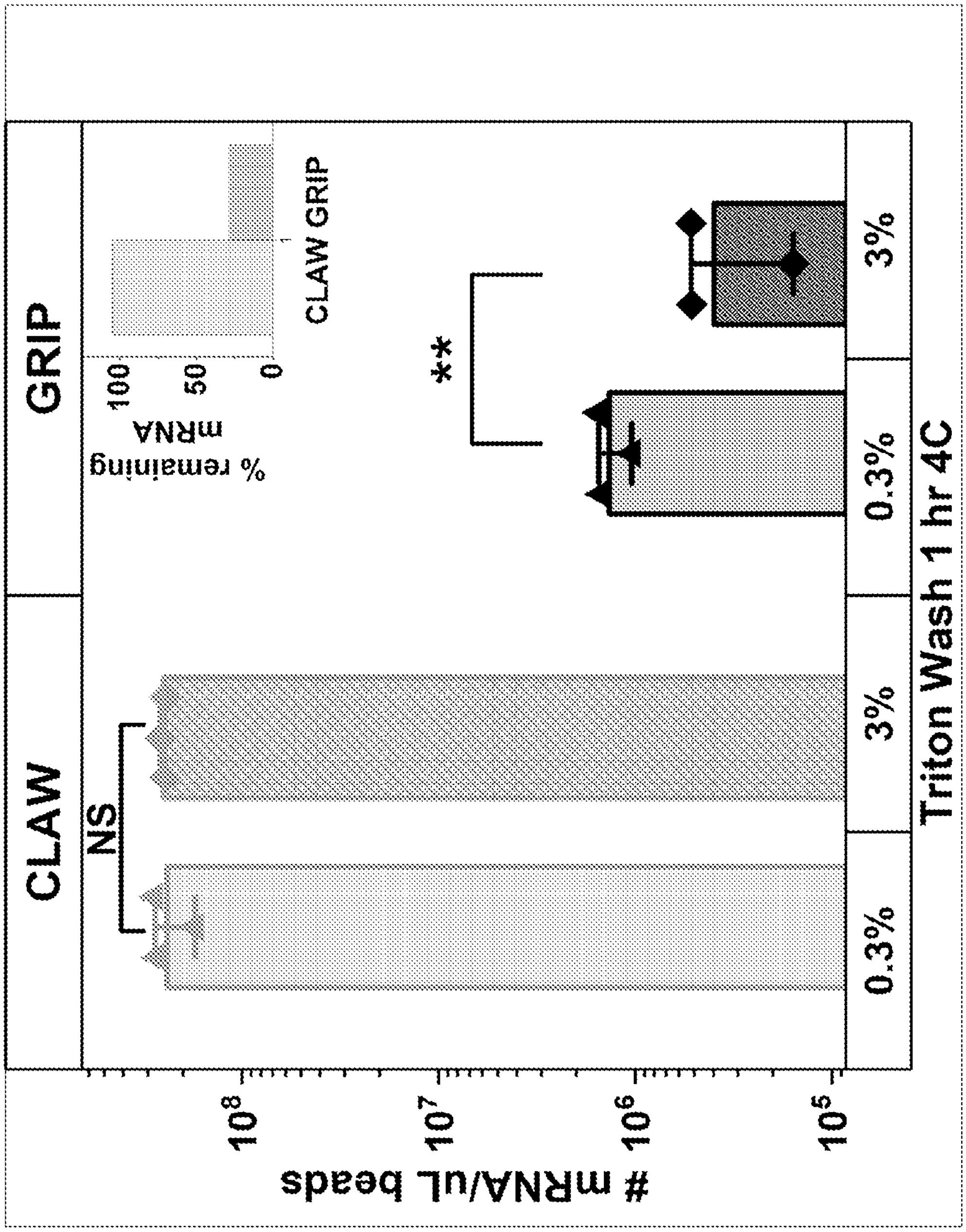
Figure 14C:
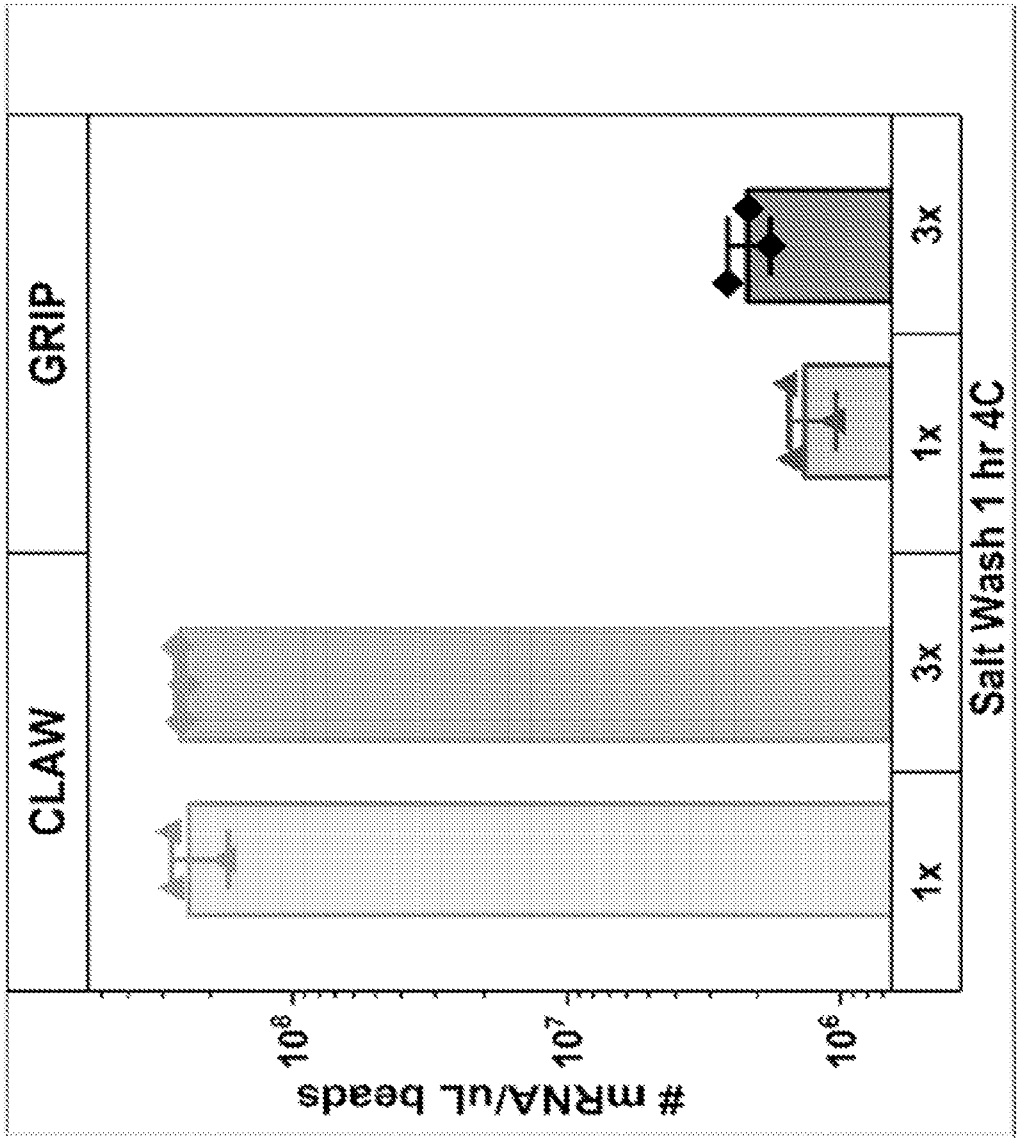

To evaluate the effect of the increased temperature, detergent or salt on the RNA-peptide complex stability, the active versions of HTP in the GRIP.1 and GRIP.2 plasmid was expressed and exposed to a long wash under various stressors and quantified the amount of the surviving RNA for both platforms. The experimental data indicates that CLAW-Toy linkage is more resistant to higher temperatures during the washing step compared to the 4boxB-4λ linkage in the GRIP.1 design. After washing for 1 hr at 37° C., GRIP.2 maintains 40% of the genetic material compared to a 1 hr wash at 4° C. GRIP. 1, on the other hand, loses 90% of the mRNA in the same experiment (FIG. 14A). Moreover, CLAW-Toy complex is 100% resistant to a high-concentration detergent during wash (which is useful to eliminate the non-specific binding to the beads). In contrast, a 10-fold increase in the detergent concentration contributes to a 75% loss of mRNA in GRIP.1 (FIG. 14B). Varying the concentration of salts during the washing step did not have a significant effect on both GRIP.1 or GRIP.2 (FIG. 14C).

“Single Read” Design

Figure 15A:
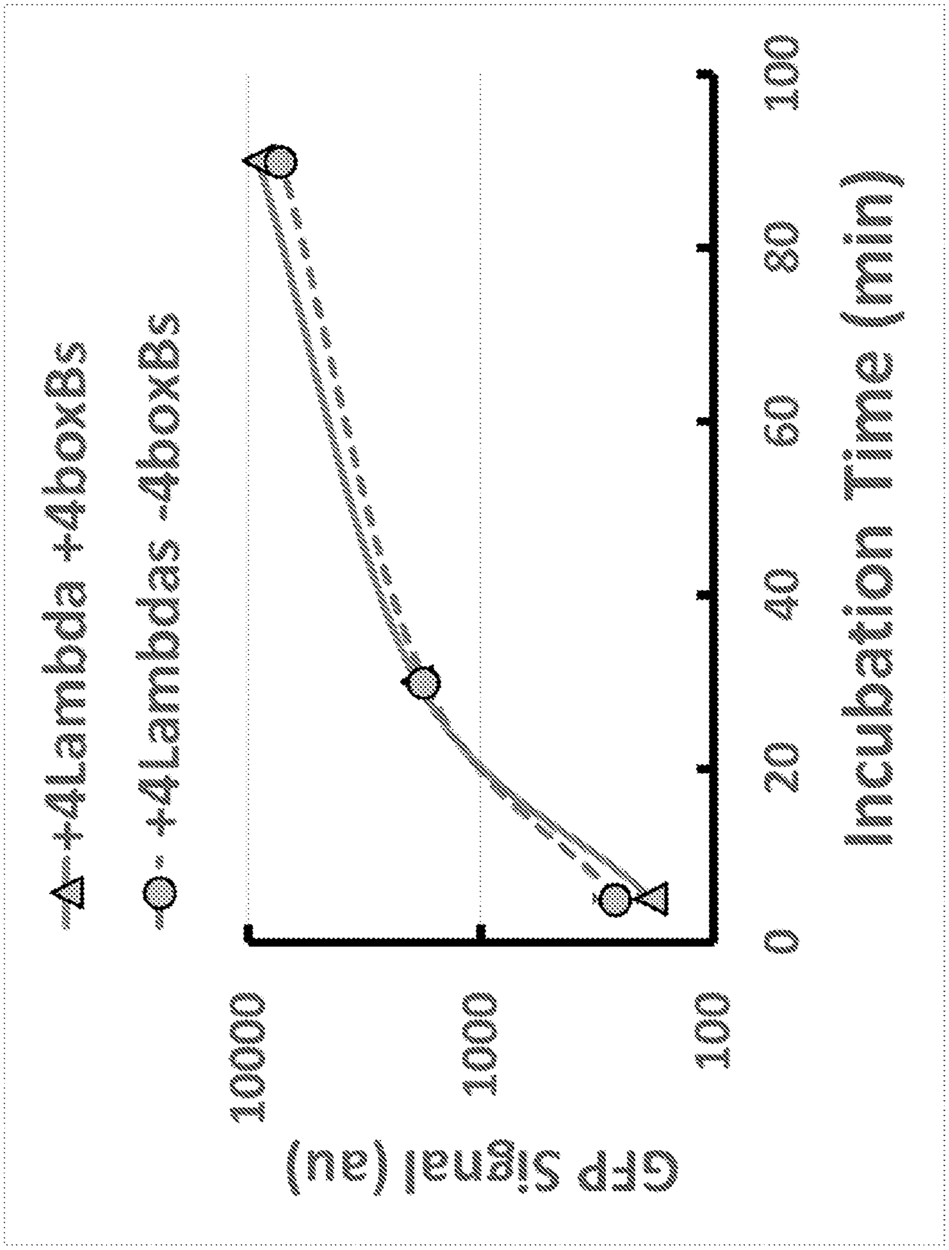
FIG. 15A-FIG. 15C show CLAW-Toy interaction promotes translational self-inhibition aka "single read technology".
Figure 15B:
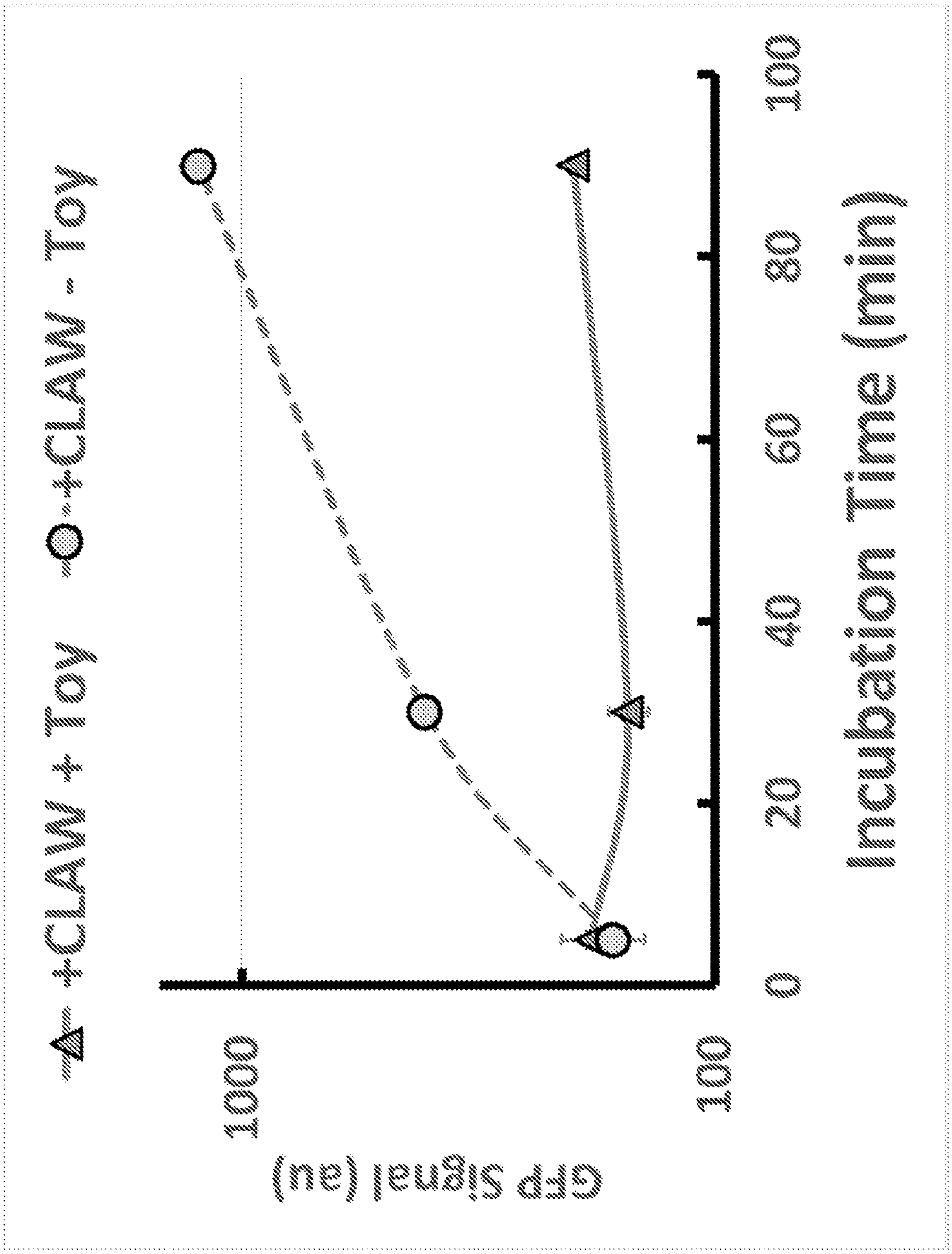

One of the desired attributes of in vitro protein display system such as GRIP is a 1:1 stoichiometry between mRNA and protein, which eliminates the off-side competition of otherwise overexpressed A peptides towards boxB hairpins as well as the competition of the overexpressed protein variants without RNA towards the target on the beads. GRIP.1 (both tetramer and trimer versions) and GRIP.2 (CLAW-Toy) were expressed with or without their RNA hairpin partners via in vitro protein expression kit for up to two hours. Samples were taken at specific time intervals and imaged via Ix83 microscope for green signal evaluation. The data indicated that GRIP.2 exhibits a “single-read” design in which CLAW-Toy binding functions as an “off switch” to promote translational self-inhibition that prevents more than one protein from being generated from a given mRNA molecule (FIG. 15B). In comparison, the tetrameric GRIP. 1 did not show this property. Its green fluorescent signal was not affected by removing the 4boxB mRNA hairpins, meaning that the 4boxB-λ complex most probably had no translational self-inhibitory effect (FIG. 15A).

Figure 15C:
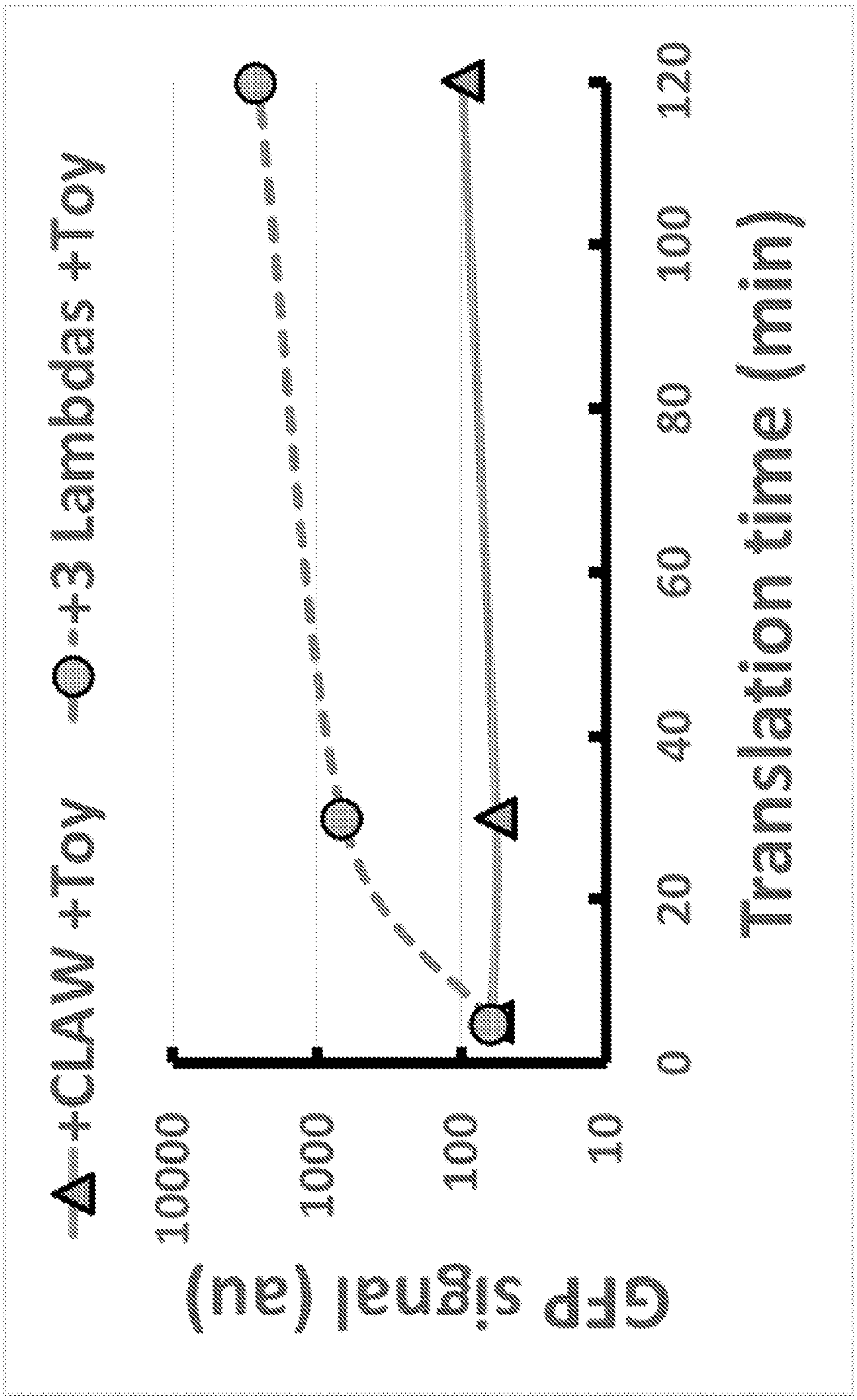

Another interesting point was established: the translational self-inhibition function is benefited by both the CLAW and the Toy component. When CLAW was substituted with another RNA hairpin trimer (3boxB), this function was lost (FIG. 15C). Therefore, GRIP.2 platform is uniquely structured with CLAW and Toy complementing the formation of the stable RNA-peptide complex. Once the complex is formed, it does not allow for another ribosome to bind and translate most probably due to the occlusion of the RBS by the bulky GFP-3λ scaffold.

In conclusion, GRIP.2 utilizes a unique set of reagents termed Toy (a trimeric boxB RNA hairpin structure) and CLAW (3λ peptides that interact with the boxB hairpin and are displayed on the surface of the GFP scaffold). These two reagents were designed to interact to form a stable RNA-peptide complex. The complex formation, in turn, is the basis of the protein display technology that allows simultaneous screening and identification of large ($10^{14}$-member) libraries of protein and peptide variants against a target of interest. GRIP.2 is an improved version of GRIP.1 Display. In particular, it retains 10-100× more genetic material during iterative panning without compromising the fidelity of the RNA-peptide link. Another improvement is the inherent translational self-inhibition property, where once the RNA-peptide complex is formed, it prevents additional ribosomes to bind and translate the same mRNA strand, thus creating a "single read" phenomenon (FIG. 15A, FIG. 15B, and FIG. 15C). This property allows an unbiased library representation, as well as redirects the reagents in the PUREfrex mix towards more mRNA-peptide complex formation rather than overexpression of extra proteins free of mRNA.

It is understood that the foregoing detailed description and accompanying examples are merely illustrative and are not to be taken as limitations upon the scope of the invention.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A nucleic acid comprising, in an upstream to downstream direction: a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop; a second portion comprising a nucleotide sequence encoding a protein including at least 2 lambda bacteriophage anti-terminator protein N domains (λ domain), wherein each individual λ domain is orientated to specifically bind to a separate and individual boxB domain; and a third portion comprising a nucleotide sequence encoding a protein of interest, wherein the third portion is operably coupled to the first portion and the second portion.

Clause 2. The nucleic acid of clause 1, wherein the protein comprises a linker between each λ domain.

Clause 3. The nucleic acid of clause 1 or 2, wherein the nucleic acid further comprises a nucleotide sequence encoding a linker between the second portion and the third portion.

Clause 4. The nucleic acid of any one of clauses 1-3, wherein the nucleic acid comprises a nucleotide sequence encoding a ribosome binding site in between the first portion and the second portion.

Clause 5. The nucleic acid of any one of clauses 1-4, wherein the nucleotide sequence of the first portion is positioned 1 nucleotide to 100 nucleotides upstream from the nucleotide sequence of the second portion.

Clause 6. The nucleic acid of any one of clauses 1-5, wherein the nucleotide sequence of the second portion comprises 30 nucleotides to 3,000 nucleotides.

Clause 7. The nucleic acid of any one of clauses 1-6, wherein the nucleotide sequence of the third portion comprises 1 nucleotide to 10,000 nucleotides.

Clause 8. The nucleic acid of any one of clauses 1-7, wherein the RNA includes 2 to 16 boxB domains.

Clause 9. The nucleic acid of any one of clauses 1-8, wherein the protein includes 2 to 16λ domains.

Clause 10. The nucleic acid of any one of clauses 1-9, wherein the RNA includes 2 to 4 boxB domains; and the protein includes 2 to 4λ domains.

Clause 11. The nucleic acid of any one of clauses 1-10, further comprising a nucleotide sequence encoding a reporter construct.

Clause 12. The nucleic acid of any one of clauses 1-11, wherein the nucleotide sequence of the first portion comprises a nucleotide sequence having at least 80% identity to SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37.

Clause 13. The nucleic acid of any one of clauses 1-12, wherein the nucleotide sequence of the second portion comprises a nucleotide sequence having at least 80% identity to SEQ ID NO:1, SEQ ID NO:3, SEQ ID NO:5, SEQ ID NO:7, SEQ ID NO:9, SEQ ID NO:11, SEQ ID NO:24, SEQ ID NO:25, SEQ ID NO:26, SEQ ID NO:27, or SEQ ID NO:28.

Clause 14. The nucleic acid of any one of clauses 1-13, wherein the nucleotide sequence of the first portion comprises a nucleotide sequence selected from the group consisting of SEQ ID NO:14, SEQ ID NO:15, SEQ ID NO:16, SEQ ID NO:17, and a combination thereof, and the RNA includes 4 boxB domains; and the protein includes 4λ domains.

Clause 15. The nucleic acid of any one of clauses 1-13, wherein the nucleotide sequence of the first portion comprises a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof, and the RNA includes 3 boxB domains; and the protein includes a scaffold protein and 3λ domains extending from the scaffold protein.

Clause 16. A protein-RNA display construct comprising: a first nucleotide portion comprising an RNA including at least 2 boxB domains, the RNA forming hairpin structures that correspond in number to the boxB domains, wherein each hairpin structure includes a stem and a loop, and wherein each individual boxB domain is located in a separate and individual loop; a second nucleotide portion comprising an mRNA encoding a protein of interest, wherein the second nucleotide portion is coupled to the first nucleotide portion; a first protein portion comprising a protein including at least 2 lambda bacteriophage anti-terminator protein N domains (λ domain), wherein each individual λ domain is orientated to specifically bind to a separate and individual boxB domain; and a second protein portion comprising the protein of interest, wherein the second protein portion is coupled to the first protein portion.

Clause 17. The protein-RNA display construct of clause 16, wherein the protein comprises a linker between each λ domain.

Clause 18. The protein-RNA display construct of clause 16 or 17, wherein the second protein portion is coupled to the first protein portion through a linker.

Clause 19. The protein-RNA display construct of clause 17 or 18, wherein the linker is 1 amino acid to 100 amino acids in length.

Clause 20. The protein-RNA display construct of any one of clauses 17-19, wherein the linker comprises an amino acid sequence selected from the group consisting of SEQ ID NO:38, SEQ ID NO:39, and SEQ ID NO:40.

Clause 21. The protein-RNA display construct of any one of clauses 16-20, wherein the RNA includes 2 to 16 boxB domains.

Clause 22. The protein-RNA display construct of any one of clauses 16-21, wherein the protein includes 2 to 16λ domains.

Clause 23. The protein-RNA display construct of any one of clauses 16-22, wherein the RNA includes 2 to 4 boxB domains; and the protein includes 2 to 4λ domains.

Clause 24. The protein-RNA display construct of any one of clauses 16-23, further comprising a reporter construct.

Clause 25. The protein-RNA display construct of clause 24, wherein the reporter construct comprises a fluorescent protein.

Clause 26. The protein-RNA display construct of any one of clauses 16-25, wherein the RNA comprises a nucleotide sequence having at least 80% identity to SEQ ID NO:14, SEQ ID NO:15, SEQ ID NO:16, SEQ ID NO:17, SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, or SEQ ID NO:37.

Clause 27. The protein-RNA display construct of any one of clauses 16-26, wherein the protein comprises an amino acid sequence having at least 80% identity to SEQ ID NO:2, SEQ ID NO:4, SEQ ID NO:6, SEQ ID NO:8, SEQ ID NO:10, SEQ ID NO:12, SEQ ID NO:13, or SEQ ID NO:22.

Clause 28. The protein-RNA display construct of any one of clauses 16-27, wherein the RNA comprises a nucleotide sequence selected from the group consisting of SEQ ID NO:14, SEQ ID NO:15, SEQ ID NO:16, SEQ ID NO:17, and a combination thereof, and the RNA includes 4 boxB domains; and the protein includes 4λ domains.

Clause 29. The protein-RNA display construct of any one of clauses 16-28, wherein the protein comprises an amino acid sequence selected from the group consisting of SEQ ID NO:2, SEQ ID NO:4, SEQ ID NO:6, SEQ ID NO:8, SEQ ID NO:10, SEQ ID NO:12, and a combination thereof.

Clause 30. The protein-RNA display construct of any one of clauses 16-27, wherein the RNA comprises a nucleotide sequence selected from the group consisting of SEQ ID NO:18, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, and a combination thereof, and the RNA includes 3 boxB domains; and the protein includes a scaffold protein and 3λ domains extending from the scaffold protein.

Clause 31. The protein-RNA display construct of any one of clauses 16-27 or 30, wherein the protein comprises an amino acid sequence of SEQ ID NO:13, SEQ ID NO:22, or a combination thereof.

Clause 32. A nucleic acid comprising, in an upstream to downstream direction: a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop; a second portion comprising a nucleotide sequence encoding a protein including at least 2 lambda bacteriophage anti-terminator protein N domains (λ domain), wherein each individual λ domain is orientated to specifically bind to a separate and individual boxB domain; and a cloning site for insertion of a nucleotide sequence encoding a protein of interest, the cloning site operably coupled to the first portion and the second portion.

Clause 33. A library of protein-RNA display constructs comprising a plurality of the protein-RNA display construct according to any one of clauses 16-31.

Clause 34. The library of clause 33, wherein each protein-RNA display construct comprises a different protein of interest.

Clause 35. A kit comprising: the nucleic acid of any one of clauses 1-15 or 32, a protein-RNA display construct of any one of clauses 16-31, or a combination thereof; and one or more packages, receptacles, labels, or instructions for use.

Clause 36. A method of performing high throughput proteomics, the method comprising: (a) expressing one or more of the nucleic acids according to claim 1, thereby producing a library of protein-RNA display constructs, wherein the protein of interest is coupled to the mRNA encoding the protein of interest; (b) contacting the library of protein-RNA display constructs with a target molecule; (c) identifying at least one protein of interest that specifically binds to the target molecule; and (d) optionally sequencing the mRNA encoding the at least one protein of interest that specifically binds to the target molecule.

Clause 37. The method of clause 36, further comprising: (e) removing at least one protein of interest that specifically binds to the target molecule to provide an enriched library of protein-RNA display constructs; and (f) optionally repeating steps (b)-(e) one or more times.

Clause 38. The method of clause 37, wherein the at least one protein of interest that specifically binds to the target molecule is amplified prior to repeating steps (b)-(e).

Clause 39. The method of any one of clauses 36-38, wherein the target molecule comprises a protein, an oligonucleotide, a small molecule, a carbohydrate, a lipid, or a combination thereof.

Clause 40. The method of any one of clauses 36-39, wherein the target molecule is a protein.

Clause 41. The method of any one of clauses 36-40, wherein the library comprises at least $1\times10^{12}$ different proteins of interest.

Clause 42. The method of any one of clauses 36-41, wherein the one or more of the nucleic acids are expressed in vitro.

SEQUENCES

```
(SEQ ID NO: 1)
atg gac gca caa aca cga cga cgt gag cgt cgc gct gag aaa caa gct caa tgg aaa gct gca aac

(SEQ ID NO: 2)
M D A Q T R R R E R R A E K Q A Q W K A A N
```

-continued (SEQ ID NO: 3)
ggt aat gca cgt aca cga cga cgt gag cgt cgc gct gag aaa caa gct caa tgg aaa gct gca aac (SEQ ID NO: 4)
G N A R T R R R E R R A E K Q A Q W K A A N (SEQ ID NO: 5)
gga aat gcc cga aca cgg cgg cgc gag cgt cga gct gaa aaa caa gca cag tgg aag gca gca aat (SEQ ID NO: 6)
G N A R T R R R E R R A E K Q A Q W K A A N (SEQ ID NO: 7)
ggt aac gca cgg acc cga cga cga gaa cgc cgg gog gag aag caa gct cag tgg aaa gcg gct aat (SEQ ID NO: 8)
G N A R T R R R E R R A E K Q A Q W K A A N (SEQ ID NO: 9)
gga aac gct cgt acg cgt cgc cgt gag cga cgt gca gaa aag cag gcg caa tgg aaa gct gcc aac (SEQ ID NO: 10)
G N A R T R R R E R R A E K Q A Q W K A A N (SEQ ID NO: 11)
ggc aat gcg cgc act cgc cgt cgg gaa cgg cgc gcc gag aaa cag gcc caa tgg aag gcc gcg aat (SEQ ID NO: 12)
G N A R T R R R E R R A E K Q A Q W K A A N (SEQ ID NO: 13)
GNARTRRRERRAEKQAQWKAAN (SEQ ID NO: 14)
ttttggggccctgaaaaagggcccctttttttgccctgaaaaagggcaaattttaaagccctgaaaaagggctttttttcccgccctgaaa
aagggcgggtttt (SEQ ID NO: 15)
ttttggggccctgaaaaagggcccctttttttgccctgaaaaagggcaaattttaaagccctgaaaaagggcttttttt (SEQ ID NO: 16)
ttttggggccctgaaaaagggcccctttttttgccctgaaaaagggcaaatttt (SEQ ID NO: 17)
ttttggggccctgaaaaagggccccttttt (SEQ ID NO: 18)
gcccccccgggcccgccctgaaaaagggcgggggggccctgaaaaagggccccggggccctgaaaaagggcccccccggggg
gc (SEQ ID NO: 19)
gcccccc (SEQ ID NO: 20)
gggccc (SEQ ID NO: 21)
gccctgaaaaagggc (SEQ ID NO: 22)
MSKGEELFTGVVPILVELDGDVNGHKFSVRGEGEGDATIGKLTLKFICTTGKLPVPWPTLVTTLT

YGVQCFSRYPDHMKRHDFFKSAMPEGYVQERTISFKDDGKYKTRAVVKFEGDTLVNRIELKGT

DFKEDGNILGHKLEYNFNSHNVYITADKQKNGIKANFTVRHNVEGGGNARTRRRERRAEKQAQ

WKAANGEAAAKEAAAKEAAAKGDGSVQLADHYQQNTPIGDGPVLLPDNHYLSTQTVLSKGNA

RTRRRERRAEKQAQWKAANGGGEAAAKEAAAKEEAAKGGGGGDHMVLHEYVNAAGITGGN

ARTRRRERRAEKQAQWKAAN (SEQ ID NO: 23)
EAAAKEAAAKEAAAK (SEQ ID NO: 24)
ggaaatgcacgaacacgacgccgggagcgtcgagctgaaaaacaggctcaatggaaagccgcaaat -continued (SEQ ID NO: 25)
ggcaacgcccgcacccgtcgtcgagaacgacgggccgaaaagcaagcacagtggaaagctgcgaac (SEQ ID NO: 26)
ggtaatgctcgtactcgccgacgtgaacggcgtgcagagaaacaagcccaatggaaggcagctaat (SEQ ID NO: 27)
gaggctgctgccaaagaggcagccgcaaaggaagctgctgctaaggaggcggctgcaaaa (SEQ ID NO: 28)
gaagcggcagctaaggaagcagcggcaaaagaggccgcagcgaaagaagcagcagccaaa (SEQ ID NO: 29)
NNNNNNNNNNNNNGCCCUGAAAAAGGGCNNNNNNGCCCUGAAAAAGGGCNNNNNNGCC
CUGAAAAAGGGCNNNNNNNNNNNNN (where N means it can be A, U, G, or C)

(SEQ ID NO: 30)
GCCCCCCGGGCCCGCCCUGAAAAAGGGGGGGGGGGGCCUGAAAAAGGGCCCCGGGGC
CCUGAAAAAGGGCCCCCCCGGGGGGC (SEQ ID NO: 31)
GCGCCCCGGGCCCGCCCUGAAAAAGGGCGGGUGGGCCCUGAAAAAGGGCCCAGGGGC
CCUGAAAAAGGGCCCCCCCGGGGCGC (SEQ ID NO: 32)
GCGCCCCGGGCCCGCCCUGAAAAAGGGGGGGGGGGGCCUGAAAAAGGGCCCCGGGGC
CCUGAAAAAGGGCCCCCCCGGGGCGC (SEQ ID NO: 33)
GCCGCCCGGGCCCGCCCUGAAAAAGGGCGGGGGGGCCCUGAAAAAGGGCCCCGGGGC
CCUGAAAAAGGGCCCCCCCGGGCGGC (SEQ ID NO: 34)
GCCCGCCGGGCCCGCCCUGAAAAAGGGGGGGGGGGGCCUGAAAAAGGGCCCCGGGGC
CCUGAAAAAGGGCCCCCCCGGCGGGC (SEQ ID NO: 35)
GCCCCGCGGGCCCGCCCUGAAAAAGGGGGGGGGGGGCCUGAAAAAGGGCCCCGGGGC
CCUGAAAAAGGGCCCCCCCGCGGGGC (SEQ ID NO: 36)
GCCCCCGGGGCCCGCCCUGAAAAAGGGCGGGGGGGCCCUGAAAAAGGGCCCCGGGGC
CCUGAAAAAGGGCCCCCCCCGGGGGC (SEQ ID NO: 37)
GCCCCCCCCCCCGGCCCUGAAAAAGGGCCGGGGGGCCCUGAAAAAGGGCCCCGGGGCC
CUGAAAAAGGGCCCCGGGGGGGGGC (SEQ ID NO: 38)
$SSGSS_n$ (SEQ ID NO: 39)
$GGSGG_n$ (SEQ ID NO: 40)
$(G)_n$

What is claimed is:

1. A nucleic acid comprising, in an upstream to downstream direction:

a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop;

a second portion comprising a nucleotide sequence encoding a protein including at least 2 lambda bacteriophage anti-terminator protein N domains (λ domain), wherein each individual λ domain is orientated to specifically bind to a separate and individual boxB domain; and a third portion comprising a nucleotide sequence encoding a protein of interest, wherein the third portion is operably coupled to the first portion and the second portion, wherein the nucleotide sequence of the first portion comprises a nucleotide sequence having at least 80% identity to SEQ ID NO:14, SEQ ID NO: 15, SEQ ID NO: 16, SEQ ID NO: 17, SEQ ID NO: 18, SEQ ID NO:29, SEQ ID NO:30, SEQ ID NO:31, SEQ ID NO:32, SEQ ID NO:33, SEQ ID NO:34, SEQ ID NO: 35, SEQ ID NO:36, or SEQ ID NO:37.

2. A nucleic acid comprising, in an upstream to downstream direction:

a first portion comprising a nucleotide sequence encoding an RNA including at least 2 boxB domains, the RNA forming hairpin structures that correspond in number to the boxB domains, wherein each hairpin structure includes a stem and a loop, and wherein each individual boxB domain is located in a separate and individual loop;

a second portion comprising a nucleotide sequence encoding a protein including at least 2 lambda bacteriophage anti-terminator protein N domains (λ domain), wherein each individual λ domain is orientated to specifically bind to a separate and individual boxB domain; and a third portion comprising a nucleotide sequence encoding a protein of interest, wherein the third portion is operably coupled to the first portion and the second portion, wherein the nucleotide sequence of the second portion comprises a nucleotide sequence having at least 80% identity to SEQ ID NO: 1, SEQ ID NO:3, SEQ ID NO:5, SEQ ID NO:7, SEQ ID NO:9, SEQ ID NO: 11, SEQ ID NO:24, SEQ ID NO:25, SEQ ID NO:26, SEQ ID NO:27, or SEQ ID NO:28.

3. The nucleic acid of claim 1, wherein the nucleotide sequence of the first portion comprises a nucleotide sequence selected from the group consisting of SEQ ID NO: 14, SEQ ID NO: 15, SEQ ID NO: 16, SEQ ID NO: 17, and a combination thereof, and the RNA includes 4 boxB domains; and the protein includes 4λ domains.

4. The nucleic acid of claim 1, wherein the nucleotide sequence of the first portion comprises a nucleotide sequence selected from the group consisting of SEQ ID NO: 18, SEQ ID NO:29, SEQ ID NO:30, SEQ ID NO:31, SEQ ID NO:32,SEQ ID NO:33, SEQ ID NO:34, SEQ ID NO:35, SEQ ID NO:36, SEQ ID NO:37, and a combination thereof, and the RNA includes 3 boxB domains; and the protein includes a scaffold protein and 3λ domains extending from the scaffold protein.

5. A protein-RNA display construct comprising:

a first nucleotide portion comprising an RNA including at least 2 boxB domains, the RNA forming hairpin structures that correspond in number to the boxB domains, wherein each hairpin structure includes a stem and a loop, and wherein each individual boxB domain is located in a separate and individual loop;

a second nucleotide portion comprising an mRNA encoding a protein of interest, wherein the second nucleotide portion is coupled to the first nucleotide portion;

a first protein portion comprising a protein including at least 2 lambda bacteriophage anti-terminator protein N domains (λ domain), wherein each individual λ domain is orientated to specifically bind to a separate and individual boxB domain; and a second protein portion comprising the protein of interest, wherein the second protein portion is coupled to the first protein portion wherein the RNA comprises a nucleotide sequence having at least 80% identity to SEQ ID NO: 14, SEQ ID NO: 15, SEQ ID NO: 16, SEQ ID NO: 17, SEQ ID NO: 18, SEQ ID NO:29, SEQ ID NO: 30, SEQ ID NO:31, SEQ ID NO:32, SEQ ID NO:33, SEQ ID NO:34, SEQ ID NO:35, SEQ ID NO: 36, or SEQ ID NO:37.

6. A protein-RNA display construct comprising:

a first nucleotide portion comprising an RNA including at least 2 boxB domains, the RNA forming hairpin structures that correspond in number to the boxB domains, wherein each hairpin structure includes a stem and a loop, and wherein each individual boxB domain is located in a separate and individual loop;

a second nucleotide portion comprising an mRNA encoding a protein of interest, wherein the second nucleotide portion is coupled to the first nucleotide portion;

a first protein portion comprising a protein including at least 2 lambda bacteriophage anti-terminator protein N domains (λ domain), wherein each individual λ domain is orientated to specifically bind to a separate and individual boxB domain; and a second protein portion comprising the protein of interest, wherein the second protein portion is coupled to the first protein portion wherein the protein comprises an amino acid sequence having at least 80% identity to SEQ ID NO: 2, SEQ ID NO:4, SEQ ID NO: 6, SEQ ID NO:8, SEQ ID NO: 10, SEQ ID NO: 12, SEQ ID NO: 13, or SEQ ID NO:22.

7. The protein-RNA display construct of claim 5, wherein the RNA comprises a nucleotide sequence selected from the group consisting of SEQ ID NO: 14, SEQ ID NO: 15, SEQ ID NO: 16, SEQ ID NO: 17, and a combination thereof, and the RNA includes 4 boxB domains; and the protein includes 4λ domains.

8. The protein-RNA display construct of claim 7, wherein the protein comprises an amino acid sequence selected from the group consisting of SEQ ID NO:2, SEQ ID NO:4, SEQ ID NO:6,SEQ ID NO:8, SEQ ID NO: 10, SEQ ID NO: 12, and a combination thereof.

9. The protein-RNA display construct of claim 5, wherein the RNA comprises a nucleotide sequence selected from the group consisting of SEQ ID NO: 18, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, and a combination thereof, and the RNA includes 3 boxB domains; and the protein includes a scaffold protein and 3λ domains extending from the scaffold protein.

10. The protein-RNA display construct of claim 9, wherein the protein comprises an amino acid sequence of SEQ ID NO: 13, SEQ ID NO:22, or a combination thereof.

* * * * *